US007381412B2

(12) United States Patent
Andrew et al.

(10) Patent No.: US 7,381,412 B2
(45) Date of Patent: Jun. 3, 2008

(54) ANTI-TECK ANTIBODIES AND METHODS OF USE THEREFOR

(75) Inventors: David P. Andrew, Waltham, MA (US); Brian A. Zabel, Stanford, CA (US); Paul D. Ponath, San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/109,349

(22) Filed: Apr. 19, 2005

(65) Prior Publication Data

US 2005/0181501 A1 Aug. 18, 2005

Related U.S. Application Data

(63) Continuation of application No. 09/522,752, filed on Mar. 10, 2000, now Pat. No. 6,936,248, which is a continuation-in-part of application No. 09/266,464, filed on Mar. 11, 1999, now Pat. No. 6,329,159.

(51) Int. Cl.
*A61K 39/395* (2006.01)

(52) U.S. Cl. .............................. 424/141.1; 424/130.1; 424/143.1; 435/7.1; 435/326; 435/332; 435/334; 435/70.21; 530/350; 530/387.1; 530/388.1; 530/388.22

(58) Field of Classification Search .................... None
See application file for complete search history.

(56) References Cited

U.S. PATENT DOCUMENTS

| | | | |
|---|---|---|---|
| 5,440,021 A | 8/1995 | Chantharapai et al. |
| 5,652,133 A | 7/1997 | Murphy |
| 6,329,159 B1 | 12/2001 | Andrew et al. |
| 6,503,735 B2 | 1/2003 | Wei et al. |
| 6,689,570 B2 | 2/2004 | Andrew et al. |
| 6,723,520 B2 | 4/2004 | Wang et al. |
| 6,884,574 B2 | 4/2005 | Andrew et al. |
| 6,936,248 B1 | 8/2005 | Andrew et al. |
| 2002/0141991 A1 | 10/2002 | Andrew et al. |
| 2003/0018167 A1 | 1/2003 | Wang et al. |
| 2003/0022238 A1 | 1/2003 | Andrew et al. |

FOREIGN PATENT DOCUMENTS

| | | |
|---|---|---|
| WO | WO 97/48807 | 12/1997 |
| WO | WO 98/01557 | 1/1998 |
| WO | WO 98/32858 | 7/1998 |

OTHER PUBLICATIONS

Ngo et al., 1994, The Protein Folding Problem and Tertiary Structure Prediction, pp. 492-495.*
Attwoo, Science 2000; 290:471-473.*
Skolnick et al. ,Trends in Biotech. 2000; 18(1):34-39.*
Metzler et al., Nature Structural Biol. 1997; 4:527-531.*
Yoshida, R., et al., "Molecular Cloning of a Novel Human CC Chemokine EBI1-ligand Chemokine That is a Specific Functional Ligand for EBI1, CCR7," *The Journal of Biological Chemistry*, 272(21): 13803-13809 (1997).
Baba, M., et al., "Identification of CCR6, the Specific Receptor for a Novel Lymphocyte-Directed CC Chemokine LARC," *The Journal of Biological Chemistry*, 272(23): 14893-14898 (1997).
Imai, T., et al., "The T Cell-Directed CC Chemokine TARC is Highly Specific Biological Ligand for CC Chemokine Receptor 4," *The Journal of Biological Chemistry*, 272(23): 15036-15042 (1997).
Kitaura, M., et al., "Molecular Cloning of Human Eotaxin, an Eosinophil-selective CC Chemokine, and Identification of a Specific Eosinophil Eotaxin Receptor, CC Chemokine Receptor 3," *The Journal of Biological Chemistry*, 271(13): 7725-7730 (1996).
Vicari, A.P., et al., "TECK: A Novel CC Chemokine Specifically Expressed by Thymic Dendritic Cells and Potentially Involved in T Cell Development," *Immunity*, 7:291-301 (1997).
Damon, I., et al., "Broad Spectrum Chemokine Antagonistic Activity of a Human Poxvirus Chemokine Homolog," *Proc. Natl. Acad. Sci. USA*, 95:6403-6407 (1998).
O'Garra, A., et al, "T-cell Subsets: Chemokine Receptors Guide the Way," *Current Biology*, 8:R646-R649 (1998).
Kim, C.H., et al., "Chemokines: Signal Lamps for Trafficking of T and B Cells for Development and Effector Function," *J. Leukoc. Biol.*, 65:6-15 (1999).
Murphy, P.M., "The Molecular Biology of Leukocyte Chemoattractant Receptors," *Annu. Rev. Immunol.*, 12:593-633 (1994).
Zlotnik, A., et al., "Recent Advances in Chemokines and Chemokine Receptors," *Critical Reviews™ in Immunology*, 19:1-47 (1999).
Nomiyama, H., et al., "The Human CC Chemokine TECK (SCYA25) Maps to Chromosome 19p13.2," *Genomics*, 51:311-312 (1998).
Vicari, A.P., et al., "TECK: A Novel CC Chemokine Associated with T-Cell development," *J. Allergy Clin. Immunol.*, 99(1):S246, Abstract No. 1003, (1997).
Combadiere, C., et al., "Cloning and Functional Expression of Two Human CC Chemokine Receptors," *FASEB J. 10(6)*:A1093 Abstract No. 545, (1996).
Gao, J.-L., et al., "Cloning and Expression of the Mouse MIP-1α Receptor Gene and Two Related Genes," *9th International Congress of Immunology*, p. 108, Abstact No. 637 (1995).
GenBank Accession No. U45982, "Human G Protein Coupled Receptor GPR-9-6 Gene, Complete CDS," (1996).

(Continued)

*Primary Examiner*—Eileen B. O'Hara
*Assistant Examiner*—Yunsoo Kim
(74) *Attorney, Agent, or Firm*—Hamilton, Brook, Smith & Reynolds, P.C.

(57) ABSTRACT

The invention relates to antibodies or antigen-binding fragments thereof which binds the chemokine mammalian TECK and inhibit binding of the chemokine to mammalian GPR-9-6. The invention also relates to host cells that produce such antibodies or antigen-binding fragments, kits comprising such antibodies or antigen-binding fragments and methods of use for such antibodies and antigen-binding fragments.

4 Claims, 28 Drawing Sheets

OTHER PUBLICATIONS

Zaballos, A., et al., "Cutting Edge: Identification of the Orphan Chemokine Receptor GPR-9-6 as CCR9, the Receptor for the Chemokine TECK," *J. Immunol.*, 162(10):5671-5675 (1999).

Chuntharapai, A. and Kim, K.J., "Generation of Monoclonal Antibodies to Chemokine Receptors," *Methods in Enzymology*, 288:15-27 (1997).

Locati M. et al., "Chemokines and Chemokine Receptors: Biology and Clinical Relevance in Inflammation and AIDS," *Annu. Rev. Med. 50*:425-440 (1999).

Zabel, B.A. et al., "Human G Protein-coupled Receptor GPR-9-6/ CC Chemokine Receptor 9 is Selectively Expressed on Intestinal Homing T Lymphoctyes, Mucosal Lymphocytes, and Thymocytes and is Required for Thymus-expressed Chemokine-mediated Chemotaxis," *J. Exp. Med 190*(9):1241-1255 (1999).

Swissprot Database, Accession No.: P51686, "Portable G-Protein-Coupled Receptor GPR-9-6" [online], Oct. 1996

Nibbs, R.J.B., et al., "Cloning and Characterization of a Novel Promiscuous Human β-Chemokine Receptor D6," *J. Biol. Chem.*, 272(51):32078-32083 (1997).

Murphy, P.M., et al., "International Union of Pharmacology. XXII. Nomenclature for Chemokine Receptors," *Pharmacol. Rev.*, 52(1):145-176 (2000).

Youn, B-S, et al., "TECK, an Efficacious Chemoattractant for Human Thymocytes, Uses GPR-9-6/CCR9 as a Specific Receptor," *Blood*, 94(7):2533-2536 (1999).

Attwood, T.K., "The Babel of Bioingormatics," *Science*, 290:471-473 (2000).

MOLT-13, ACC 436, [online] Deutsche Sammlung von Mikroorganismen und Zellkulturen GmbH, 2003 [retrieved on Mar. 4, 2003]. Retrieved from the Internet:<URL: www.dsmz.de/ dsmzhome.htm.

Huang, Z., "Structural Chemistry and Therapeutic Intervention of Protein-Protein Interactions in Immune Response, Human Immunodeficiency Virus Entry and Apoptosis," *Pharmacology & Therapeutics*, 86:201-215 (2000).

Zlotnick, et al., "Chemokines: A New Classification System and Their Role in Immunity," *Immunity*, 12:121-127 (2000).

Mackay, C., "Chemokines: Immunology's High Impact Factors," *Nature Immunology*, 2(2):95-101 (2001).

ATCC Accession No.: CRL-1582, ATCC Cell Lines and Hybridomas, p. 149, 7th Edition, 1992 American Type Culture Collection, current address 10801 University Boulevard, Manassas, VA 20110-2209.

Hoffmann, J.C., et al., "Animal Models of Inflammatory Bowel Disease: An Overview," *Pathobiology*, 3(70): 121-130 (2002).

Taneja, V. and David, C.S., "Lessons from Animal Models for Human Autoimmune Diseases," *Nature Immunology 2(9)*: 781-784 (2001).

* cited by examiner of amino acids substitutions between protein pairs

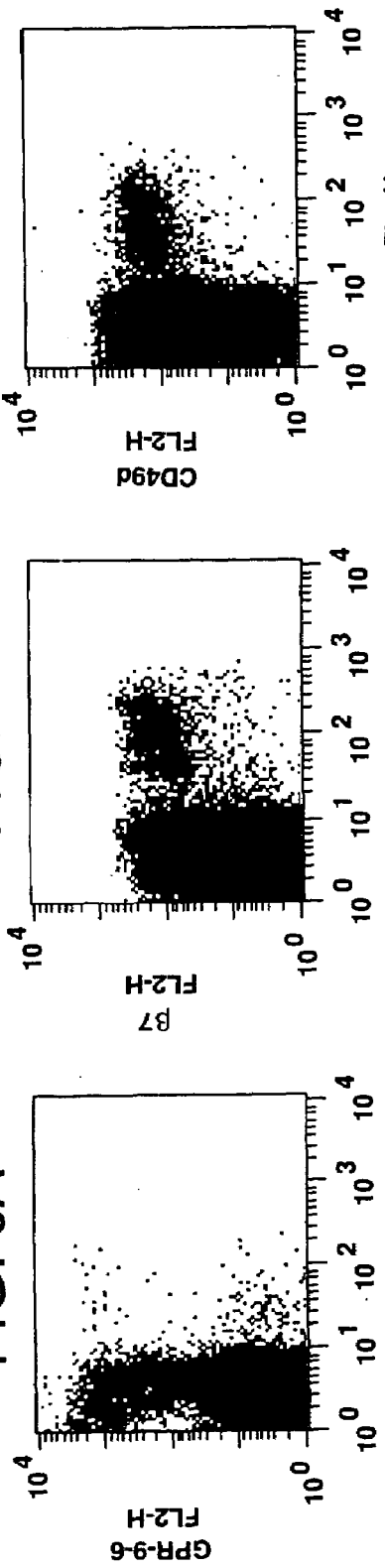
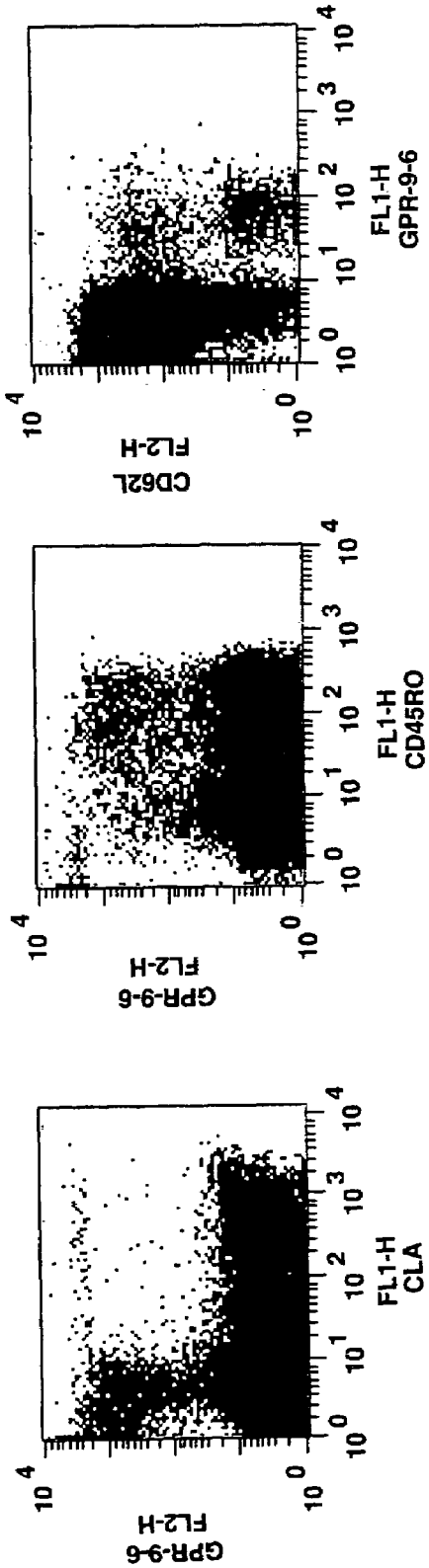

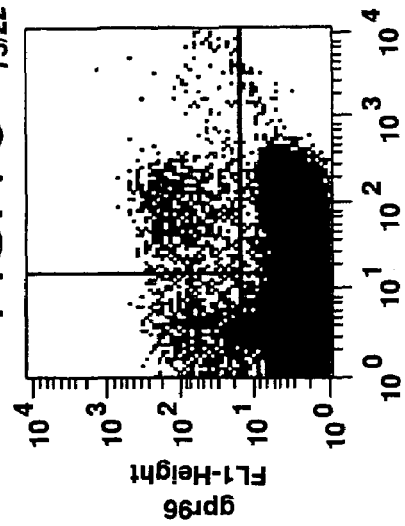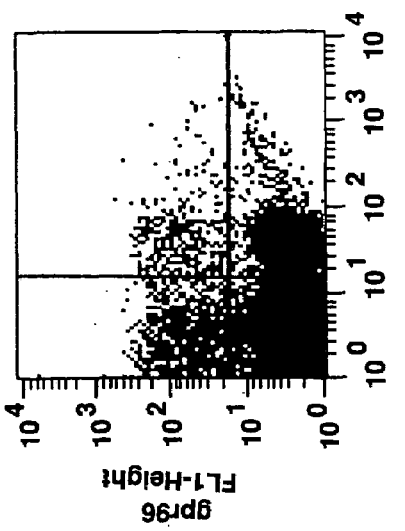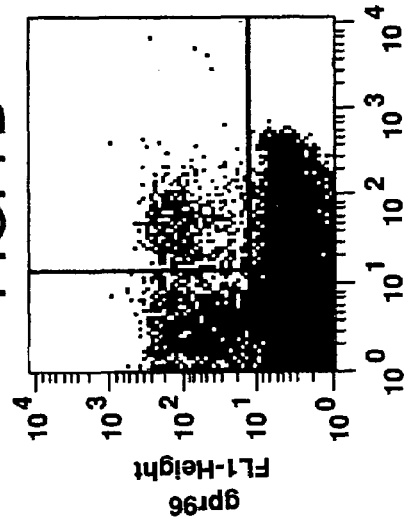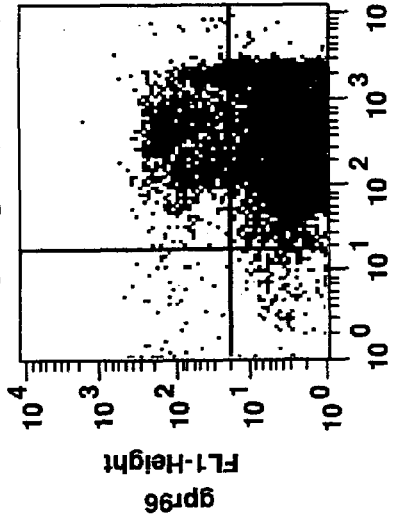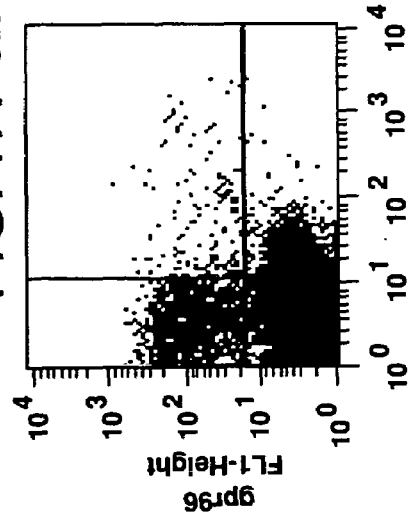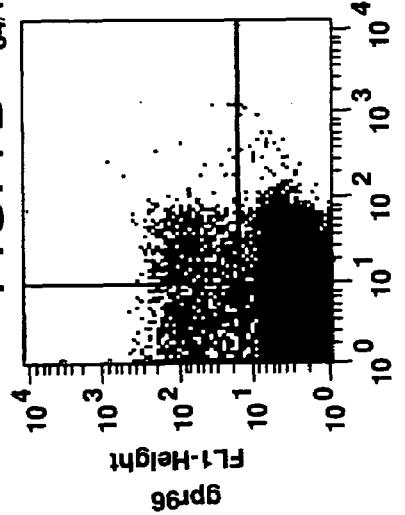

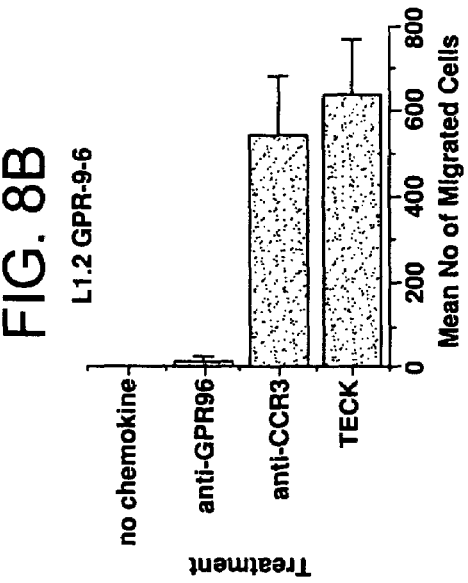
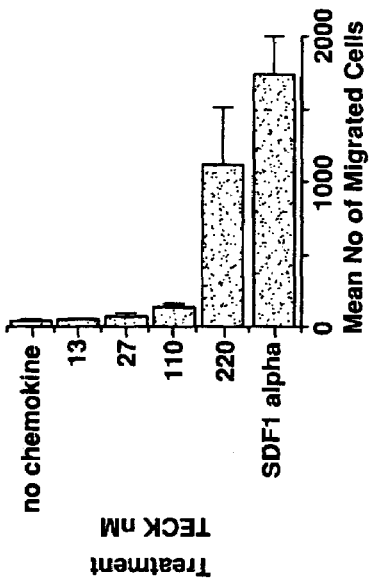
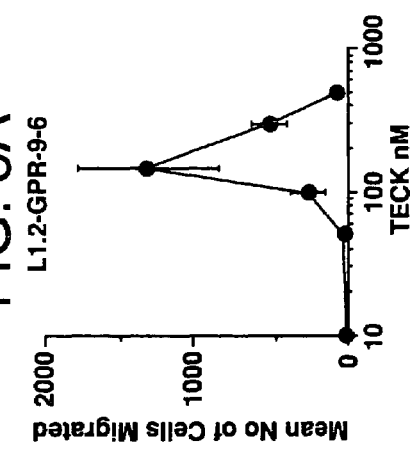
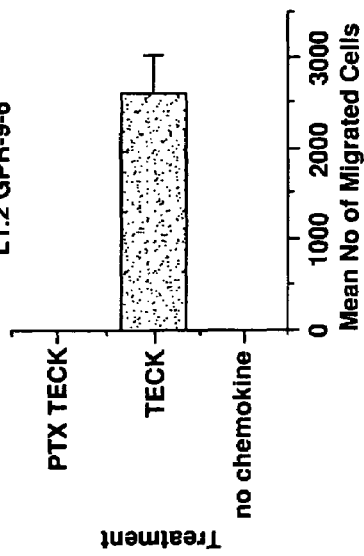

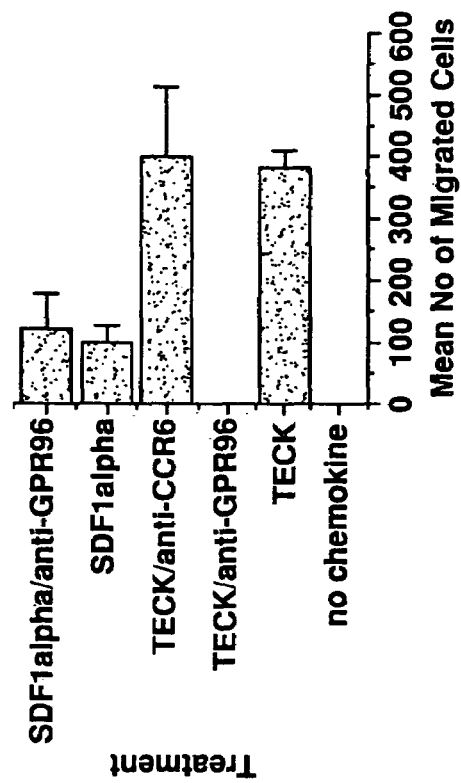
FIG. 8F MOLT13
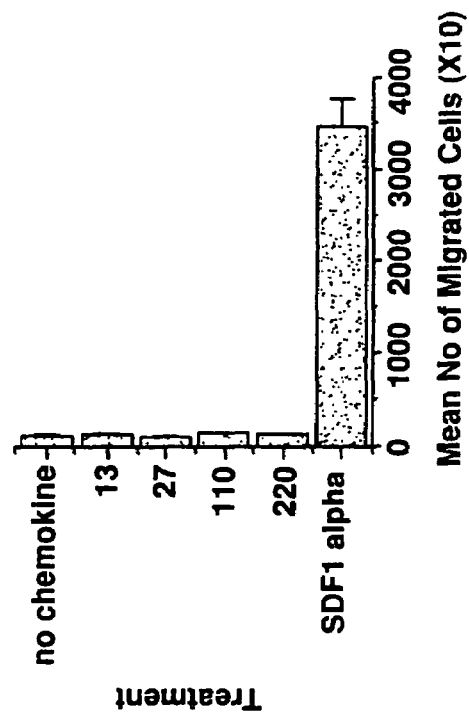
FIG. 8E SKW3

CD8 Lymphocytes

Monocytes

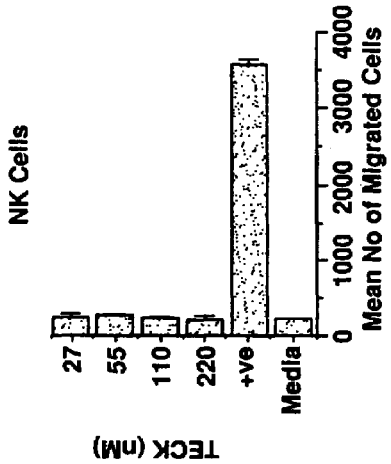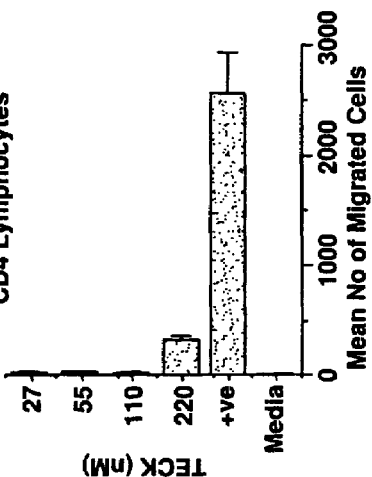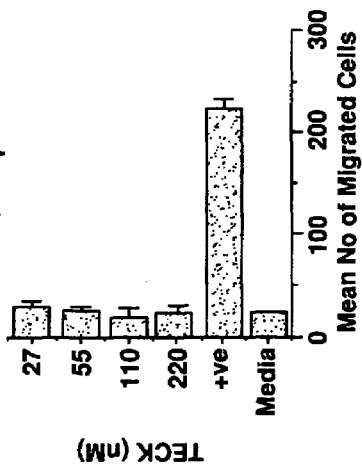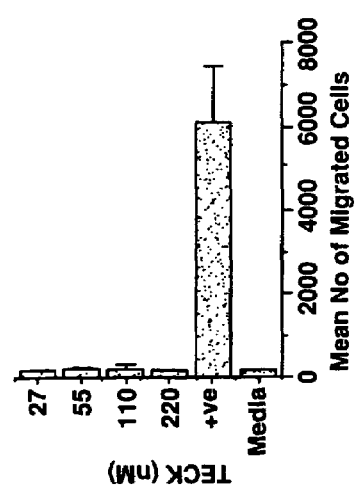

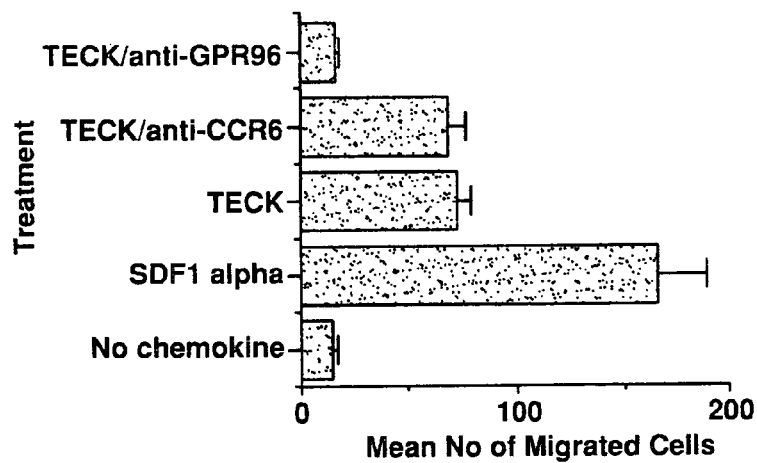
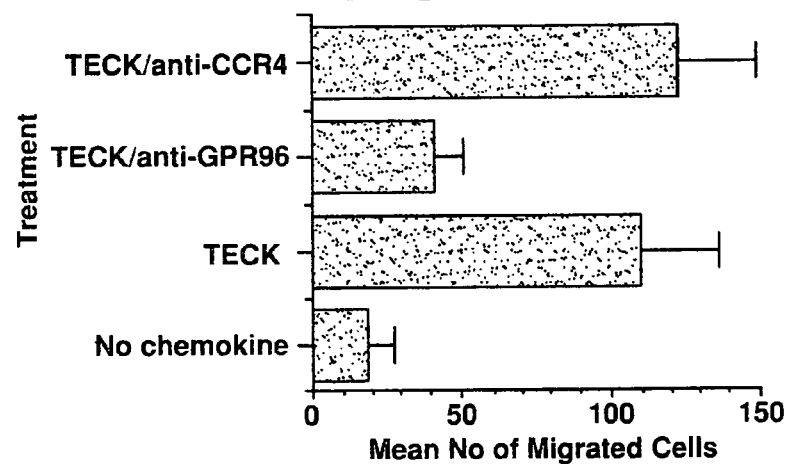
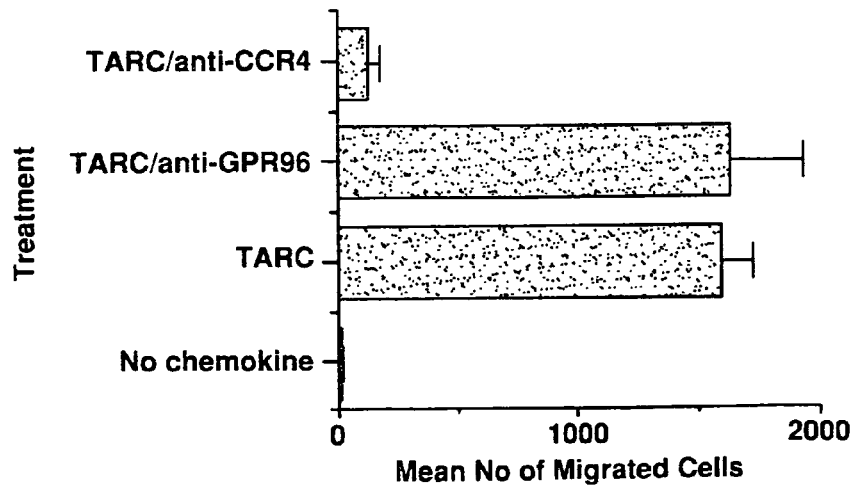

Memory CD4 T cells
CD4 (+) CD45RA (-)

Memory CD8 T cells
CD8 (hi) CD45RA (lo/neg) CD27 (+)

FIG. 14A

```
   1 aatattttcc ttgacctaat gcatcttgt gtcccttgc agagccctat tcctaacatg
  61 gctgatgact atggctctga actgtgagaa atccacatct tccatggaag actacgttaa cttcaacttc
 121 actgacttct actgtgagaa aaacaatgtc aggcagtttg cgagccattt cctcccaccc
 181 ttgtactggc tcgtgttcat cgtgggtgcc ttgggcaaca gtcttgttat ccttgtctac
 241 tgtactgca caagagtgaa gaccatgacc gacatgttcc tttgaattt ggcaattgct
 301 gacctcctct ttccttgtca tcttccccttc tgggccattg ctgctgctga ccagtggaag
 361 ttccagacct tcatgtgcaa ggtggtcaac agcatgtaca agatgaactt ctacagctgt
 421 gtgttgctga tcatgtgcat cagcgtggac agtacattg ccattgccca ggccatgaga
 481 gcacatactt ggagggagaa aagctttg tacagcaaaa tggttgctt taccatctgg
 541 gtattggcag ctgctctctg catcccagaa atcttataca gccaaatcaa ggaggaatcc
 601 ggcattgcta tctgcaccat ggtttaccct agcgatgaga gcaccaaact gaagtcagct
 661 gtcttgaccc tctgggttc tctggggttc ttcctccct tcgtgtcat ggcttgctgc
 721 tataccatca tcattcacac cctgatacaa gccaagaagt cttccaagca caagccta
 781 aaagtgacca tcactgtcct gaccgtcttt gtcttgtctc agttcccta caactgcatt
 841 ttgttggtgc agaccattga cgcctatgcc atgttcatct ccaactgtgc cgtttccacc
 901 aacattgaca tctgcttcca ggtcaccag accatcgcct tcttccacag ttgctgaac
 961 cctgttctct atgttttgt gggtgagaga ttccgccggg atctcgtgaa aaccctgaag
1021 aacttggggtt gcatcagcca ggccccagtgg gtttcattta caaggagaga gggaagcttg
1081 aagctgtcgt ctatgttgct ggagacaacc tcaggagcac tctccctctg aggggtcttc
1141 tctgaggtgc atggttctt tgaagaaat gagaaataca tgaaacagtt tccccactga
1201 tgggaccaga gagagtgaaa gagaaaagaa aactcagaaa gggatgaatc tgaactatat
1261 gattactgt agtcagaatt tgccaaagca aatatttcaa aatcaactga ctagtgcagg
1321 agctgttga ttggctcttg actgtgatgc ccggacactc caaggagga ctaaggaccg
1381 gcactgtgga gcaccctggc tttgccactc gccggagcat caatgccgct gcctctgag
1441 gagcccttg atttctctcca tgcactgtga actctgtgg cttcagttct catgctgcct
1501 cttccaaaag gggacacaga agcactggct gctgctacag accgcaaaag cagaaagttt
1561 cgtgaaaatg tccatctttg ggaaatttc taccctgctc ttgagcctga taacccatgc
1621 caggtcttat agattcctga tctagaacct ttccaggcaa tctcagacct aatttcttc
1681 tgttctcctt gttctgttct gggccagtga aggtccttgt tctgattttg aaacgatctg
1741 caggtcttgc cagtgaaccc ctggacaact gaccacaccc acaaggcatc caaagtctgt
1801 tggcttccaa tccattctg tgtcctgctg gaggttttaa cctagacaag gattccgctt
```

FIG. 14B

```
1861  attccttggt atggtgacag tgtctctcca tggcctgagc agggagatta taacagctgg
1921  gttcgcagga gccagccttg tccctgttgt gcctgttc aggcttgttc tgttgagtgg cactgtctt
1981  gggtccaccg tctgtctgct ccctagaaaa tgggctggtt cttttggccc tcttcttct
2041  gaggcccact ttattctgag aatacagtg agcagatatg gcagcagcc aggtagggca
2101  aaggggtgaa gcgcaggcct tgctggaagg ctatttactt ccatgcttct cctttttctta
2161  ctctatagtg gcaacatttt aaaagctttt aacttagaga ttaggctgaa aaaaataagt
2221  aatggaattc acctttgcat cttttgtgtc tttcttatca tgatttggca aaatgcatca
2281  cctttgaaaa tatttcacat attggaaaag tgcttttaa tgtgtatatg aagcattaat
2341  tacttgtcac ttcttttacc ctgtctcaat attttaagtg tgtgcaatta aagatcaaat
2401  agatacatta agagtgtgaa ggctggtctg aagtagtga gctatctcaa tcggattgtt
2461  cacactcagt tacagattga actccttgtt ctacttccct gcttctctct actgcaattg
2521  actagtcttt aaaaaaaagt gtgaagagta agcaataggg ataaggaaat aagatct
```

FIG. 15

MADDYGSESTSSMEDYVNFNFTDFYCEKNNVRQFASHFLPPLYW
LVFIVGALGNSLVILVYWYCTRVKTMTDMFLLNLAIADLLFLVTLPFWAIAAADQWKF
QTFMCKVVNSMYKMNFYSCVLLIMCISVDRYIAIAQAMRAHTWREKRLLYSKMVCFTI
WVLAAALCIPEILYSQIKEESGIAICTMVYPSDESTKLKSAVLTLKVILGFFLPFVVM
ACCYTIIIHTLIQAKKSSKHKALKVTITVLTVFVLSQFPYNCILLVQTIDAYAMFISN
CAVSTNIDICFQVTQTIAFFHSCLNPVLYVFVGERFRRDLVKTLKNLGCISQAQWVSF
TRREGSLKLSSMLLETTSGALSL

FIG. 20

```
  1 atgaacctgt ggctcctggc ctgcctggtg gccggcttcc tgggagcctg gccccccgct
 61 gtccacaccc aaggtgtctt tgaggactgc tgcctggcct accactaccc cattgggtgg
121 gctgtgctcc ggcgcgcctg gacttaccgg atccaggagg tgagcgggag ctgcaatctg
181 cctgctgcga tattctacct ccccaagaga cacaggaagg tgtgtgggaa ccccaaaagc
241 agggaggtgc agagagccat gaagctcctg gatgctcgaa ataaggtttt tgcaaagctc
301 caccacaaca ygcagacctt ccaagcaggc cctcatgctg taaagaagtt gagttctgga
361 aactccaagt tatcatcatc caagtttagc aatccaatca gcagcagcaa gaggaatgtc
421 tccctcctga tatcagctaa ttcaggactg tgagccggct catttctggg ctccatcgcc
481 acaggagggg ccggatcttt ctccgataaa accgtcgccc tacagaccca gctgtcccca
541 cgcctctgtc ttttgggtca agtcttaatc cctgcacctg agttggtcct ccctctgcac
601 cccaccacc tcctgcccgt ctggcaactg gaaagaagga gttggcctga ttttaacctt
661 ttgccgctcc ggggaacagc acaatcctgg gcagccagtg gctccttgtag agaaaactta
721 ggatacctct ctcactttct gtttcttgcc gtccaccccg ggccatgcca gtgtgtcctc
781 tgggtcccct ccaaaaatct ggtcattcaa ggatcccctc ccaaggctat gctttctat
841 aacttttaaa taaaccttgg ggggtgaatg gaataaaaa
```

FIG. 21

1  mnlwllaclv agflgawapa vhtqgvfedc clayhypigw avlrrawtyr iqevsgscnl
61 paaifylpkr hrkvcgnpks revqramkll darnkvfakl hhnXq

FIG. 22

```
  1  atgaacctgt ggctcctggc ctgcctggtg gccggcttcc tgggagcctg ggccccgct
 61  gtccacaccc aaggtgtctt tgaggactgc tgcctggcct accactaccc cattgggtgg
121  gctgtgctcc ggcgcgcctg gacttaccgg atccaggagg tgagcgggag ctgcaatctg
181  cctgctgcga tattctacct cccaagagag cacaggaagg tgtgtgggaa ccccaaaagc
241  agggaggtgc agagagccat gaagctcctg gatgctcgaa ataaggtttt tgcaagctc
301  caccacaaca ygcagacctt ccaagcccct catgctgtaa agaagttgag ttctggaaac
361  tccaagttat catcatccaa gtttagcaat cccatcagca gcagcaagag gaatgtctcc
421  ctcctgatat cagctaattc aggactgtga gccgctcat ttctgggctc catcggcaca
481  ggaggggccg gatctttctc cgataaaacc gtcgccctac agacccagct gtccccacgc
541  ctctgtctttt tgggtcaagt cttaatccct gcacctgagt tggtcctccc tctgcacccc
601  caccacctcc tgcccgtctg gcaactggaa agaaggagtt ggcctgattt taaccttttg
661  ccgctccggg gaacagcaca atcctgggca gccagtggct cttgtagaga aaacttagga
721  tacctctctc actttctgtt tcttgcgtc cacccggc catgccagtg tgtcctctgg
781  gtcccctcca aaaatctggt cattcaagga tcccctccca aggctatgct tttctataac
841  ttttaaataa accttggggg gtgaatggaa taaaaa
```

FIG. 23

```
  1  mnlwllaclv agflgawapa vhtggvfedc clayhypigw avlrrawtyr iqevsgscnl
 61  paaifylpkr hrkvcgnpks revqramkll darnkvfakl hhnxqtfqgp havkklssgn
121  sklssskfsn pissskrnvs llisansgl
```

ANTI-TECK ANTIBODIES AND METHODS OF USE THEREFOR

RELATED APPLICATIONS

This application is a continuation of patent application Ser. No. 09/522,752, filed on Mar. 10, 2000, now U.S. Pat. No. 6,936,248 B1, which is a continuation-in-part of patent application Ser. No. 09/266,464, filed Mar. 11, 1999, now U.S. Patent No. 6,329,159 B1. The entire teachings of the above applications are incorporated herein by reference.

BACKGROUND OF THE INVENTION

Chemokines are a large and growing family of nearly forty 6-14 kD (non-glycosylated) heparin binding proteins that mediate a wide range of biological functions (Taub, D. D. and Openheim, J. J., *Ther. Immunol.*, 1:229-246 (1994)). The chemokines can be divided into families based on the position of four cysteine residues that form two disulfide bonds (Kelner, G. S., et al., *Science*, 266:12395-1399 (1994); Bazan, J. F., et al., *Nature*, 385:640-644 (1997); Pin, Y., et al., *Nature*, 385:611-617 (1997)). Chemokine receptors can also be divided into families based on the type of chemokine they bind, although, no clear structural differences have been identified that distinguish the receptor sub-families (Mackay, C. R., *J. Exp.Med.*, 184:799-802 (1996)). In addition, there are a number of so called "orphan" chemokine receptors (e.g., GPR-9-6) which share sequence homology with well characterized chemokine receptors. However, the biological functions and specific agonists of orphan receptors remain unknown.

Chemokines play a vital role in leukocyte adhesion and extravasation. For example, in various in vitro assays, chemokines can induce the chemotaxis or transendothelial migration of leukocytes (Taub, D. D. and Openheim, J. J., *Ther. Immunol.*, 1:229-246 (1994)), while in vivo injection (Taub, D. D., et al., *J. Clin. Invest.*, 97:1931-1941 (1996)) or over-expression of chemokines (Fuentes, M. E., et al., *J. Immunol.*, 155:5769-5776 (1995)) can result in leukocyte accumulation at the site of chemokine injection or expression. Antagonists of chemokines can prevent leukocyte trafficking (Bargatze, R. F. and Butcher, E. C., *J. Exp. Med.*, 178:367-372 (1993)) and may have beneficial effects in several models of acute and chronic inflammation (Sekido, N., et al., *Nature*, 365:654-657 (1993); Karpus, W. J., et al., *J. Immunol.*, 155:5003-5010 (1995)). Chemokines have also been reported to modulate angiogenesis (Gupta, S. K., et al., *Proc. Natl. Acad. Sci. USA*, 92:7799-7803 (1995)), hematopoiesis (Taub, D. D. and Openheim, J. J., *Ther. Immunol.*, 1:229-246 (1994)) as well as T lymphocyte activation (Zhou, Z., et al., *J. Immunol.* 151:4333-4341 (1993); Taub, D. D., et al., *J. Immunol.*, 156:2095-2103 (1996)). In addition, several chemokine receptors act as co-receptors, along with CD4, for entry of M tropic and T tropic HIV-1 (Choe, H., et al., *Cell*, 85:1135-1148 (1996); Feng, Y., et al., *Science*, 272:872-877 (1996)).

Several subsets of CD4 lymphocytes can be defined based on their expression of various adhesion molecules that are known to effect trafficking to different physiologic sites (Mackay, C. R., *Curr. Opin. Immunol.*, 5:423-427 (1993)). For example, $CLA^{+ve}$ memory CD4 lymphocytes traffic to the skin (Berg, E. L., et al., *Nature*, 174(6): 1461-1466 (1991)), while $CLA^{-ve}$ $\alpha 4\beta 7^{+ve}$ memory CD4 lymphocytes traffic to mucosal sites (Hamman, A., et al., *J. Immunol.*, 152:3282-3292 (1994)). Leukocyte adhesion to endothelium is thought to involve several overlapping steps including rolling, activation and arrest. Rolling leukocytes are exposed to factors expressed at the adhesion site resulting in activation of the leukocyte and up-regulation of integrin-mediated adhesion. As a consequence of such integrin-mediated interactions, leukocytes arrest on the endothelium (Bargatze, R. F. and Butcher, E. C., *J. Exp. Med.*, 178:367-372 (1993); Bargatze, R. F., et al., *Immunity*, 3:99-108 (1995)). Leukocyte activation and up-regulation of integrin molecules occurs via a pertussis toxin sensitive mechanism that is thought to involve chemokine receptors (Bargatze, R. F. and Butcher, E. C., *J. Exp. Med.*, 178:367-372 (1993); Campbell, J. J., et al., *Science*, 279:381-383 (1998)).

Memory $CD4^+$ lymphocytes can be grouped based upon the expression of certain chemokine receptors. For example, CXCR3, CCR2 and CCR5 (Qin, S., et al., *Eur. J. Immunol.*, 26:640-647 (1996); Qin, S., et al., *J. Clin. Invest.*, 101:746-754 (1998); Liao, F., et al., *J. Immunol.*, 162:186-194 (1999)) are all expressed on subsets of memory CD4 lymphocytes, and certain chemokines act selectively on naive T cells (Adema, G. J., et al., *Nature*, 387:713-717 (1997)). Furthermore, several chemokines which are ligands for such receptors have been shown to be expressed in inflammatory sites (Gonzalo, J. A., et al., *J. Clin. Invest.*, 98:2332-2345 (1996)) and in some cases in lymph nodes draining a challenged site (Tedla, N., et al., *J. Immunol.*, 161:5663-5672 (1998)). In vitro derived $T_H1/T_H2$ lymphocyte lines have also been shown to differentially express chemokine receptors. Specifically, $T_H1$ lymphocytes have been shown to selectively express CXCR3 and CCR5, while $T_H2$ lymphocytes selectively express CCR4, CCR8 and CCR3 (Bonecchi, R. G., et al., *J.Exp. Med.*, 187:129-134 (1998); Sallusto, F. D., et al., *J. Exp. Med.*, 187:875-883 (1998); Sallusto, F., *Science*, 277:2005-2007 (1997); Andrew, D. P., et al., *J. Immunol* 161:5027-5038 (1998); Zingoni, A., et al., *J. Immunol.*, 161:547-555 (1998)). Interestingly, in some cases the chemokines for these respective chemokine receptors, such as MDC for CCR4 and IP-10 for CXCR3, are induced by cytokines associated with a $T_H1/T_H2$ environment (Andrew, D. P., et al., *J. Immunol* 161:5027-5038 (1998); Luster, A. D., et al., *Nature*, 315:672-676 (1985)).

SUMMARY OF THE INVENTION

The invention relates to an antibody (immunoglobulin) or functional fragment thereof (e.g., an antigen-binding fragment) which binds to a mammalian GPR-9-6 (GPR-9-6 is also referred to as CC chemokine receptor 9 (CCR9)) or portion of the receptor. In one embodiment, the antibody or antigen-binding fragment thereof binds to human GPR-9-6. In another embodiment, the antibody or antigen-binding fragment thereof can inhibit the binding of a ligand to a mammalian GPR-9-6. In a preferred embodiment, the antibody or antibody-binding fragment can bind to human GPR-9-6 and inhibit the binding of TECK to the receptor.

In particular embodiments, the antibody or antigen-binding fragment of the invention binds to an epitope which is the same as or is similar to the epitope recognized by mAb 3C3, mAb GPR96-1 or an antigen-binding fragment of either of the foregoing. For example, the binding of the antibody or antigen-binding fragment of the invention to human GPR-9-6 can be inhibited by a peptide that consists of the amino acid sequence of SEQ ID NO:3. In another embodiment, the binding of the antibody or antigen-binding fragment of the invention to human GPR-9-6 can be inhibited by mAb 3C3. In a preferred embodiment, the antibody is mAb 3C3 or antigen-binding fragment thereof. In a more preferred embodiment the antibody is mAb GPR-9-6 or antigen-binding fragment thereof.

The invention also relates to an isolated cell that produces an antibody or antigen-binding fragment of the present invention, including those which bind to mammalian GPR-9-6 and inhibit the binding of a ligand to the receptor. In a particular embodiment, the isolated cell is murine hybridoma 3C3 (also referred to as murine hybridoma LS129-3C3-E3-1) deposited under ATCC Accession No. HB-12653. In another particular embodiment, the isolated cell is murine hybridoma GPR96-1 (also referred to as murine hybridoma LS272 GPR96 1-5) deposited under ATCC Accession No. PTA-1470.

The invention also relates to a method of detecting or identifying an agent (i.e., molecule or compound) which binds to a mammalian GPR-9-6. In one embodiment, an agent which can bind to mammalian GPR-9-6 and inhibit (reduce or prevent) the binding of a ligand (e.g., TECK) to GPR-9-6 is identified in a competitive binding assay. In other embodiments, agents for use in therapy are identified in a direct binding assay. Thus, the invention encompasses methods of identifying agents which modulate GPR-9-6 function, such as, ligands or other substances which bind a mammalian GPR-9-6, including inhibitors (e.g., antagonists) or promoters (e.g., agonists) of receptor function. A suitable source of a mammalian GPR-9-6 or a ligand-binding variant thereof can be used to identify a GPR-9-6 binding agent in accordance with the method of the invention. In one embodiment, a cell (e.g., cell line, recombinant cell) that expresses a mammalian GPR-9-6 or a ligand binding variant thereof is used. In another embodiment, a membrane preparation of a cell that expresses a mammalian GPR-9-6 or a ligand binding variant thereof is used.

The invention also relates to an antibody (immunoglobulin) or functional fragment thereof (e.g., an antigen-binding fragment) which binds a mammalian TECK or portion of the chemokine. In one embodiment, the antibody or antigen-binding fragment thereof binds to human TECK. In another embodiment, the antibody or antigen-binding fragment thereof can inhibit the binding of a mammalian TECK to a receptor. In a preferred embodiment, the antibody or antibody-binding fragment can bind to human TECK and inhibit the binding of TECK to GPR-9-6.

In another embodiment, the antibody or antigen-binding fragment of the invention binds to an epitope which is the same as or is similar to the epitope recognized by mAb 11.3.1, mAb 16.3.1 or an antigen-binding fragment of either of the foregoing. In another embodiment, the binding of the antibody or antigen-binding fragment of the invention to human GPR-9-6 can be inhibited by mAb 11.3.1 and/or mAb 16.3.1. In a particular embodiment, the antibody is mAb 11.3.1 or an antigen-binding fragment thereof. In another particular embodiment, the antibody is mAb 16.3.1 or an antigen-binding fragment thereof.

The invention also relates to an isolated cell that produces an antibody or antigen-binding fragment of the present invention, including those which bind to mammalian TECK and inhibit the binding of TECK to a receptor. In a particular embodiment, the isolated cell is murine hybridoma 11.3.1 (also referred to as murine hybridoma LS250 11.3.1) deposited under ATCC Accession No. PTA-1469. In another particular embodiment, the isolated cell is murine hybridoma 16.3.1 (also referred to as murine hybridoma LS250 16.3.1) deposited under ATCC Accession No. PTA-1468.

The invention also relates to a method of detecting or identifying an agent (i.e., molecule or compound) which binds to a mammalian GPR-9-6. In one embodiment, an agent which can bind to mammalian GPR-9-6 and inhibit (reduce or prevent) the binding of a ligand (e.g., TECK) to GPR-9-6 is identified in a competitive binding assay. In other embodiments, agents for use in therapy are identified in a direct binding assay.

The invention also relates to therapeutic methods in which agents which can bind to a mammalian GPR-9-6 and modulate (inhibit or promote) a GPR-9-6 function or bind to mammalian TECK and modulate a GPR-9-6 function, are administered to a subject in need of such therapy. In one embodiment, the therapeutic method is a method of treating a subject having an inflammatory disease. In a preferred embodiment, the subject has an inflammatory diseases associated with mucosal tissues, such as an inflammatory bowel disease. In a particular embodiment, the inflammatory bowel disease is Crohn's disease or colitis. In another embodiment, the therapeutic method is a method of inhibiting GPR-9-6-mediated homing of leukocytes. In another embodiment, the method is a method of modulating a GPR-9-6 function.

The invention further relates to a method for detecting or quantifying a mammalian GPR-9-6 or a portion thereof in a biological sample. The method comprises contacting a biological sample and an anti-GPR-9-6 antibody or antigen-binding fragment of the invention under conditions suitable for binding, and detecting a complex formed between GPR-9-6 and the antibody or antigen-binding fragment. In one embodiment the biological sample comprises human cells or a fraction of said cells (e.g., membrane preparation).

The invention also relates to a test kit for identifying or quantifying a mammalian GPR-9-6 or a portion thereof in a biological sample. In one embodiment, the kit comprises an antibody of the invention and suitable ancillary reagents.

The invention further relates to a method for detecting or quantifying a mammalian TECK or a portion thereof in a biological sample. The method comprises contacting a biological sample and an anti-TECK antibody or antigen-binding fragment of the invention under conditions suitable for binding, and detecting a complex formed between TECK and the antibody or antigen-binding fragment. The invention also relates to a test kit for identifying or quantifying a mammalian TECK or a portion thereof in a biological sample. In one embodiment, the kit comprises an antibody of the invention and suitable ancillary reagents.

The invention also relates to a method of treating a subject having cancer. In one embodiment, the method comprises administering an antagonist of GPR-9-6 function to a subject having cancer. In other embodiments, an antibody, antigen-binding fusion protein or immunoconjugate which binds GPR-9-6 is administered. The invention also relates to immunoconjugates and antigen-binding fusion proteins that comprise at least an antigen-binding portion of an antibody which binds GPR-9-6 that is bonded directly or indirectly to another therapeutic agent.

The present invention further relates to an antibody, antigen-binding fragment or agent (e.g., immunoconjugate, antigen-binding fusion protein) as described herein for use in therapy (including prophylaxis) or diagnosis, and to the use of such an antibody, antigen-binding fragment or agent for the manufacture of a medicament for the treatment of a particular disease or condition as described herein (e.g., an inflammatory disease associated with mucosal tissues (e.g., inflammatory bowel disease (e.g., Crohn's disease)), cancer (e.g., acute T cell lymphoblastic leukemia)).

BRIEF DESCRIPTION OF THE DRAWINGS

In FIG. 2A, GPR-9-6/L1.2 transfectants were stained with mAb 3C3 (stippled profile), anti-CCR6 antibody ( . . . ) or with a murine IgG2b mAb ( - - - ) (n=2). In FIG. 2B, CCR6/L1.2 transfectants were stained with mAb 3C3 ( . . . ), anti-CCR6 antibody (stippled profile) or with a murine IgG2b mAb ( - - - ) (n=2).

FIG. 4E shows staining of umbilical CD4 lymphocytes with anti-CXCR4 (stippled profile), anti-GPR-9-6 (—) and IgG2b ( . . . ). FIGS. 4F-4H show staining of $T_H1$ (stippled profiles) and $T_H2$ (—) lymphocytes with anti-CXCR3 (FIG. 4F), anti-α4β7 (Act1) (FIG. 4G) or anti-GPR-9-6 (mAb 3C3) (FIG. 4H) as indicated, with ( . . . ) representing staining with an IgG2b control on $T_H1$ lymphocytes (n=3).

In FIGS. 5B-5C, mononuclear cells were activated with plate bound anti-TcR mAb OKT3 for 4 days, followed by expansion with IL-2 at 5 ng/ml. Aliquots of cells were stained over time with mAb 3C3 (FIG. 5B) to determine GPR-9-6 expression upon T lymphocyte activation, or with anti-CCR6 mAb and anti-CCR5 mAb (FIG. 5C) to determine expression of CCR-3 and CCR-5 upon T cell activation. (n=2)

FIGS. 6A-6F are a series of fluorescence plots illustrating that GPR-9-6 is expressed on $α4β7^{high}$ $CLA^{-ve}$ $CD4^+$ memory lymphocytes. Mononuclear cells were stained in three color experiments using anti-CD4 cychrome to gate on CD4 lymphocytes. The cells were also stained with anti-GPR-9-6 mAb 3C3 followed by F(ab')$_2$ anti-mouse IgG phycoerythrin to study GPR-9-6 expression on subsets defined with anti-αE (HML1, Beckman Coulter, Inc., Fullerton, Calif.) (FIG. 6A), anti-β7 (Fib504, PharMingen, San Diego, Calif.) (FIG. 6B), anti-CD49d (HP2/1, PharMingen, San Diego, Calif.) (FIG. 6C), anti-CLA (HECA 452, PharMingen, San Diego, Calif.) (FIG. 6D), anti-CD45RO (UCLH1, PharMingen, San Diego, Calif.) (FIG. 6E) and anti-CD62L (CD56)(PharMingen, San Diego, Calif.) (FIG. 6F) (n=5).

FIGS. 7A-7F are a series of fluorescence plots illustrating the expression of GPR-9-6 on CD4 lymphocytes in relation to other chemokine receptors. Mononuclear cells were stained in three-color experiments using anti-CD4 cychrome to gate on CD4 lymphocytes. The cells were also stained with anti-GPR-9-6 mAb 3C3 followed by F(ab')$_2$ anti-mouse IgG coupled to phycoerythrin to study GPR-9-6 expression on subsets defined with anti-CCR2 (R&D Systems, Minneapolis, Minn.) (FIG. 7A), anti-CCR5 (PharMingen, San Diego, Calif.) (FIG. 7B), anti-CCR6 (R&D Systems, Minneapolis, Minn.) (FIG. 7C), anti-CXCR3 (1C6, Leukosite, Inc., Cambridge, Mass. (now Millennium Pharmaceuticals, Inc. Cambridge, Mass.)) (FIG. 7D), anti-CXCR4 (PharMingen, San Diego, Calif.) (FIG. 7E) and anti-CXCR5 (R&D Systems, Minneapolis, Minn.) (FIG. 7F), all of which were coupled to phycoerythrin (n=2).

FIGS. 8A-8F are a graph and series of histograms illustrating that GPR-9-6 is a chemokine receptor for TECK. GPR-9-6/L1.2 transfectants were tested for a chemotactic response to 10 to 1000 nM TECK (FIG. 8A). FIG. 8B shows that anti-GPR-9-6 (mAb 3C3) inhibited 150 nM TECK-induced chemotaxis of GPR-9-6/L1.2 transfectants, while anti-CCR3 does not. FIG. 8C illustrates that pertussis toxin (PTX) pretreatment of the GPR-9-6/L1.2 transfectants inhibited 150 nM TECK-induced chemotaxis of GPR-9-6/L1.2 transfectants. FIG. 8D and FIG. 8E illustrate the ability of MOLT-4 cells and the inability of SKW3 cells, respectively, to chemotax to TECK. FIG. 8F illustrates the ability of MOLT-13 cells to chemotax in response to 150 nM TECK, and the ability of mAb 3C3 to block this migration, using SDF1α at 100 ng/ml as a chemokine known to induce chemotaxis of these cells through CXCR4 (n=2).

FIGS. 10A-10F are a series of histograms illustrating that a subset of CD4 lymphocytes and thymocytes chemotax to TECK. $CD4^+$ lymphocytes (FIG. 10F), $CD8^+$ lymphocytes (FIG. 10B), $CD56^+$ NK cells (FIG. 10D) and $CD14^+$ monocytes (FIG. 10A) were isolated from mononuclear cells using the appropriate Miltenyi Beads. Neutrophils (FIG. 10E) were isolated by dextran precipitation followed by Ficoll and eosinophils (FIG. 10C) separated from neutrophils by depletion with anti-CD16 Miltenyi Beads. Uncoated 3 μm Costar plates were used to assess chemotaxis with these leukocyte subsets, with the exception of eosinophils and neutrophils, for which ECV304 monolayers were grown over the inserts before the assay. In each case, TECK was tested in a dose response fashion between 1 nM and 220 nM. Chemokines known to act on the leukocyte subsets were used as positive controls (n=2).

FIGS. 11A-11C are a series of histograms illustrating that TECK-induced chemotaxis of thymocytes and CD4 lymphocytes is mediated by GPR-9-6. CD4 lymphocytes and thymocytes were pre-treated with anti-GPR-9-6 mAb 3C3 at 50 μg/ml before use in chemotaxis assays. Thymocytes were assayed using 150 nM TECK and 100 nM SDF1α (FIG.

11A), CD4 lymphocytes were assayed using 150 nM TECK (FIG. 11B), and CD4 lymphocytes were assayed using 100 nM TARC (FIG. 11C). In all assays, TECK-induced chemotaxis was inhibited by anti-GPR-9-6 (mAb 3C3). Irrelevant mAb anti-CCR6 mAb 2A9 (FIG. 11A) and anti-CCR4 mAb 2B 10 (FIG. 11B) were also examined for their effect on CD4 or thymocyte chemotaxis to TECK or TARC. For CD4 lymphocyte chemotaxis the effect of mAb 3C3 on TARC induced CD4 lymphocyte chemotaxis was also tested (FIG. 11C) as a further negative control (n=2).

Figure 12A:
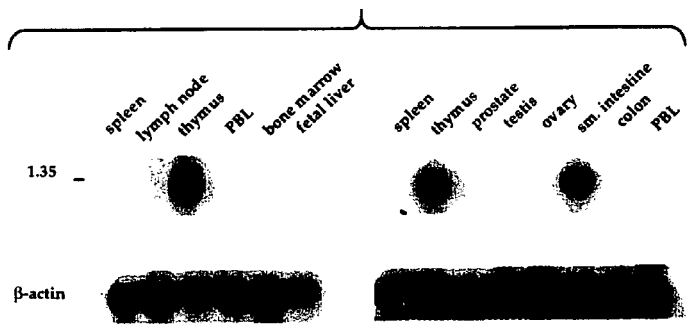
Figure 12B:
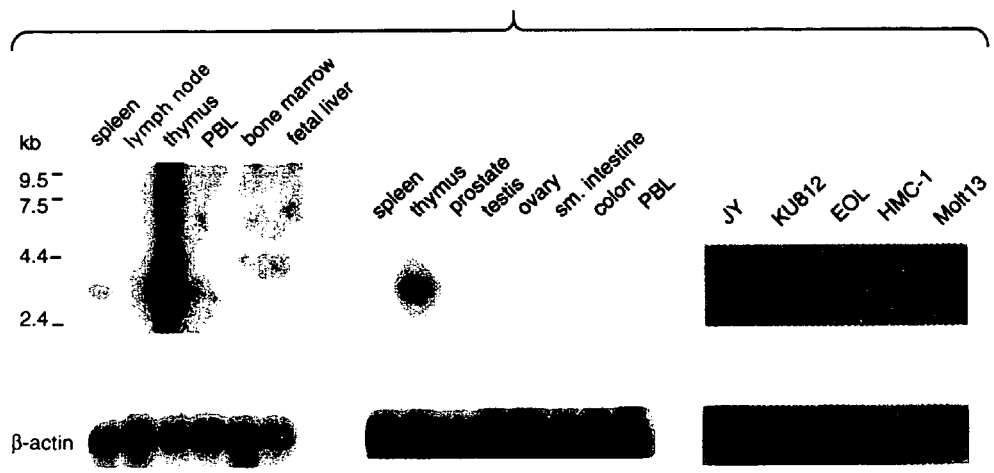
Figure 12C:
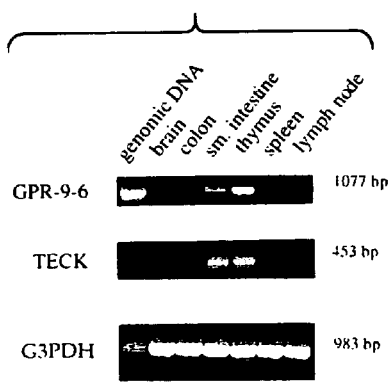

FIGS. 12A-12C illustrate the tissue distribution of TECK and GPR-9-6. Multi-tissue Northern blot analysis filters (2 µg RNA/lane) (ClonTech) and a Northern blot prepared using RNA from various cell lines (20 µg/lane) were probed with $^{32}$P TECK DNA probes (FIG. 12A) or labeled GPR-9-6 (FIG. 12B) to determine their tissue distribution. In FIG. 12C, cDNA (ClonTech) from colon, small intestine, brain, lymph node, spleen, thymus, and genomic DNA were amplified in PCR (30 cycles) using primers designed from the sequence of GPR-9-6.

Figure 13A:
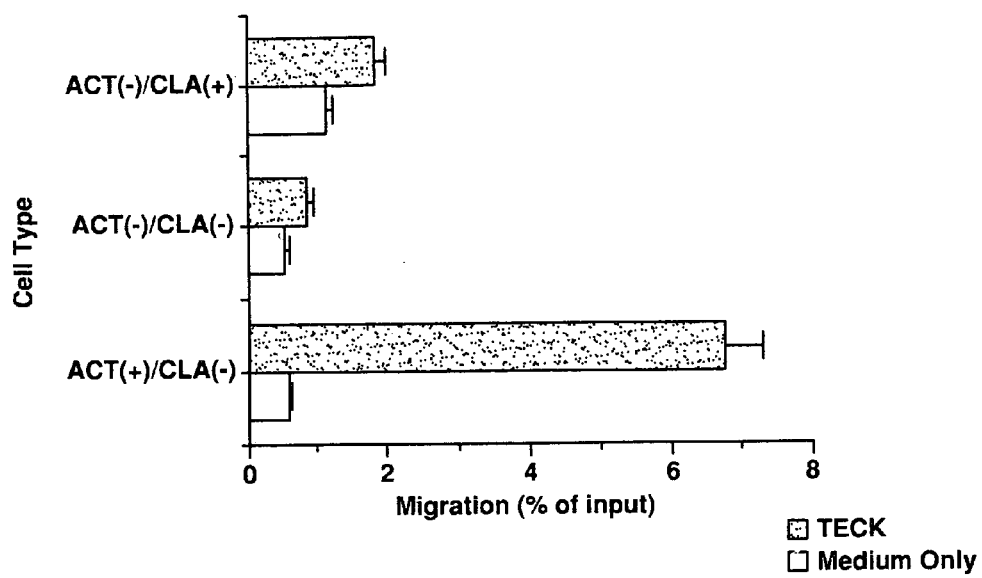
Figure 13B:
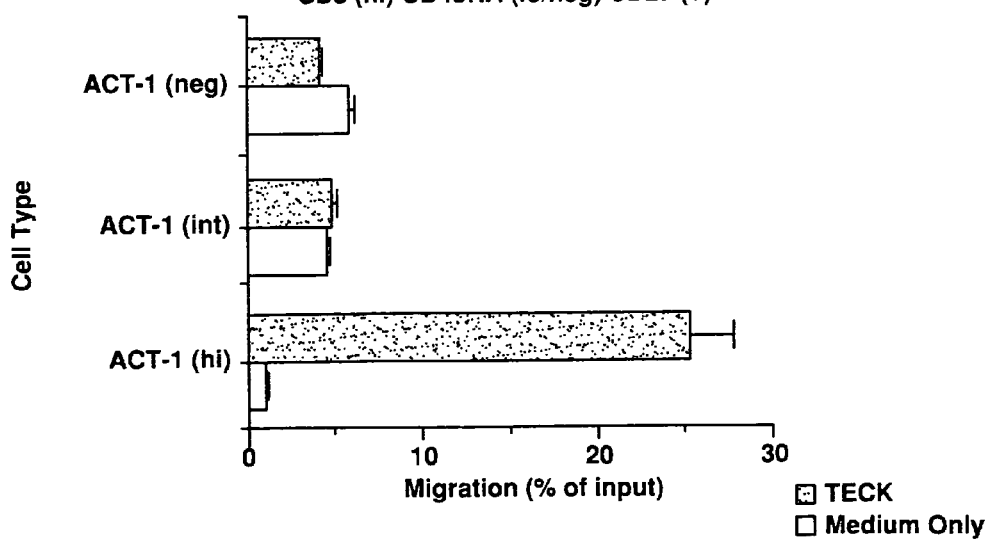

FIGS. 13A-13B are histograms illustrating that only $\alpha 4\beta 7^{high}$ CD4 and CD8 lymphocytes migrate to TECK. In a 4 color sort, memory CD8 lymphocytes defined by intermediate/negative expression of CD45RA and expression of CD27 and CD8 were sorted into $\alpha 4\beta 7$ negative, intermediate and high populations using Act1-phycoerythrin. For CD4 lymphocytes, memory CD4 lymphocytes defined by lack of CD45RA and expression of CD4 were sorted into $\alpha 4\beta 7^{-ve}$ CLA$^{-ve}$, $\alpha 4\beta 7^{-ve}$ CLA$^{+ve}$, and $\alpha 4\beta 7^{+ve}$CLA$^{-ve}$ sub-populations based on CLA and $\alpha 4\beta 7$ expression using the anti-$\alpha 4\beta 7$ antibody Act1-Phyorythrin and the anti-CLA antibody HECA 452-FITC. These sub-populations of memory CD4 (FIG. 13A) and CD8 (FIG. 13B) lymphocytes were then examined for their ability to chemotax to 1 µM TECK (n=2).

FIG. 14A-14B illustrates a nucleotide sequence encoding human (Homo sapiens) GPR-9-6 (SEQ ID NO:1) deposited in Genbank under Accession Number U45982, having an open-reading frame beginning at position 58.

FIG. 15 illustrates the amino acid sequence of a human GPR-9-6 protein (SEQ ID NO:2) encoded by the DNA sequence shown in FIG. 14A-14B (SEQ ID NO:1).

Figure 16A:
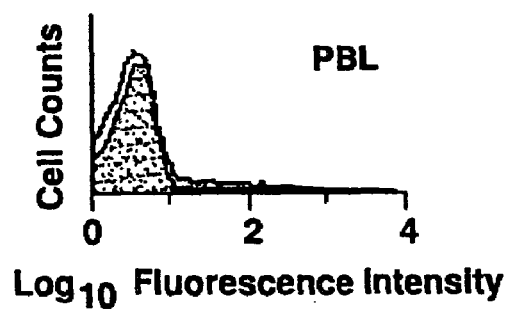
Figure 16B:
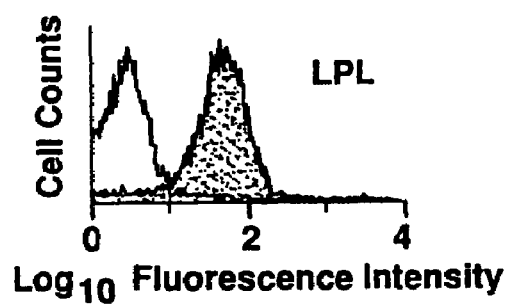
Figure 16C:
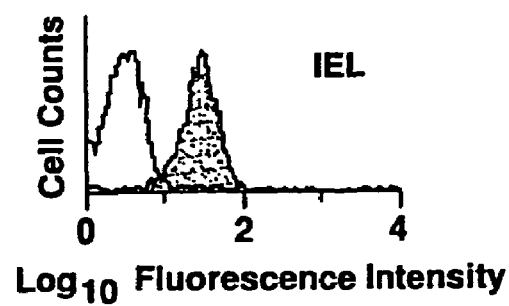

FIGS. 16A-16C are fluorescence histograms illustrating that GPR-9-6 is expressed on lymphocytes isolated from small intestine (lamina propria lymphocytes (LPL, FIG. 16B), intraepithelial lymphocytes (IEL,FIG. 16C)) but that only a small subset of peripheral blood leukocytes (FIG. 16A) express the receptor. GPR-9-6 expression was evaluated in one color studies using isolated populations of these cells and mAb 3C3 (shaded peak) or IgG2b control.

Figure 17A:
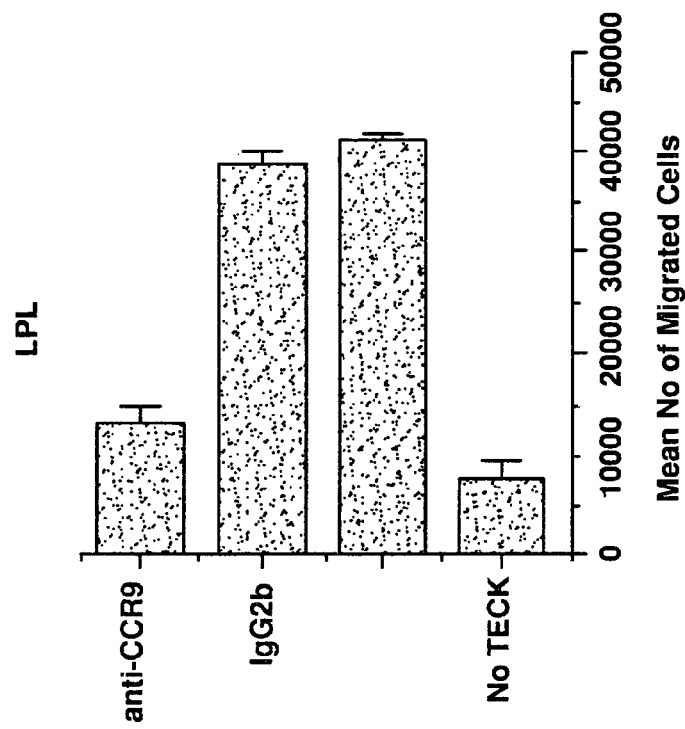
Figure 17B:
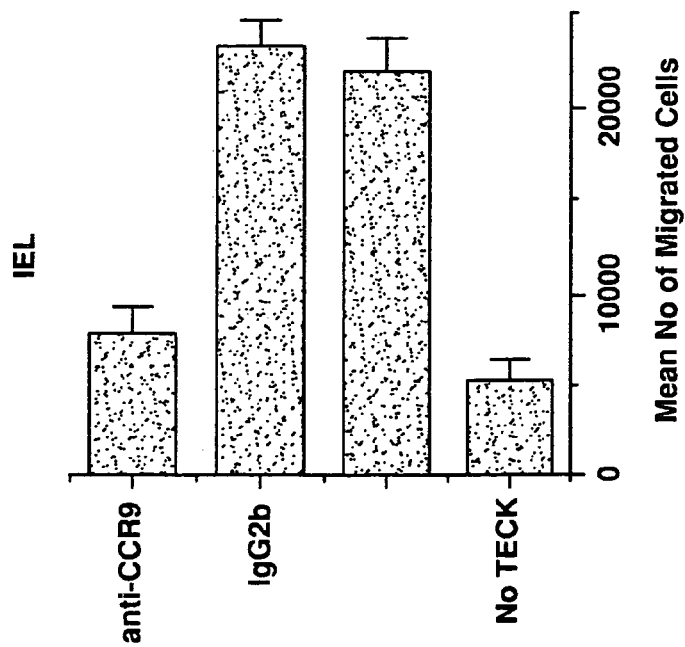

FIGS. 17A and 17B are histograms illustrating that TECK is a chemoattractant for IEL (FIG. 17A) and LPL (FIG. 17B). The histograms also show that TECK-induced chemotaxis was inhibited by mAb 3C3, revealing that GPR-9-6 is the main physiological receptor for TECK expressed on IEL and LPL. Uncoated 5 µm Transwell plates were used to assess TECK-induced chemotaxis with these leukocyte subsets. Leukocytes were incubated with mAb 3C3 (anti-CCR9), control IgG2b (IgG2b) or media alone (-) for ten minutes at 4° C. prior to exposure to TECK.

Figure 18:
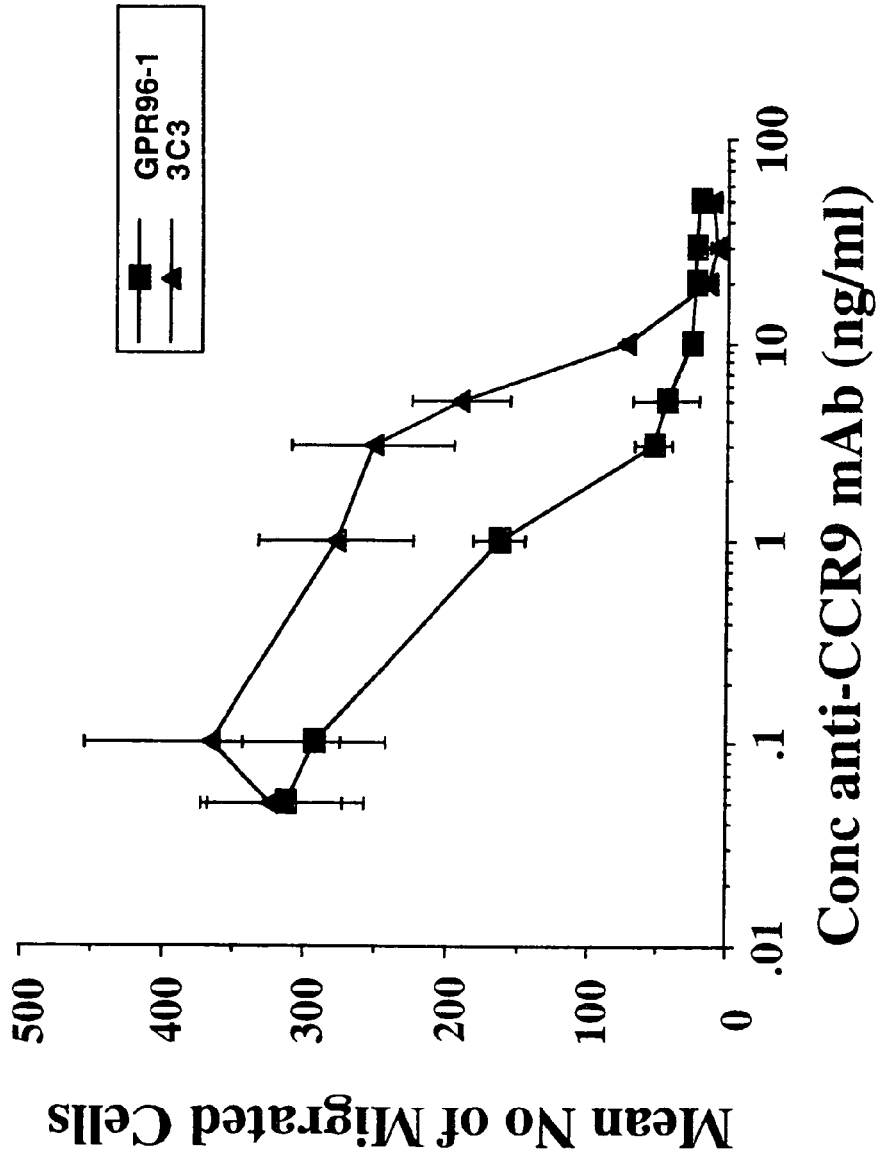

FIG. 18 is a graph illustrating dose-dependent inhibition of TECK-induced (about 150 nM) chemotaxis of GPR-9-6/L1.2 transfectants by mAb 3C3 (-▲-)or mAb GPR96-1 (-■-). GPR-9-6/L1.2 transfectants were incubated with various concentrations of anti-GPR-9-6 antibody (mAb GPR96-1 or mAb 3C3) for 10 minutes on ice prior to exposure to TECK.

Figure 19:
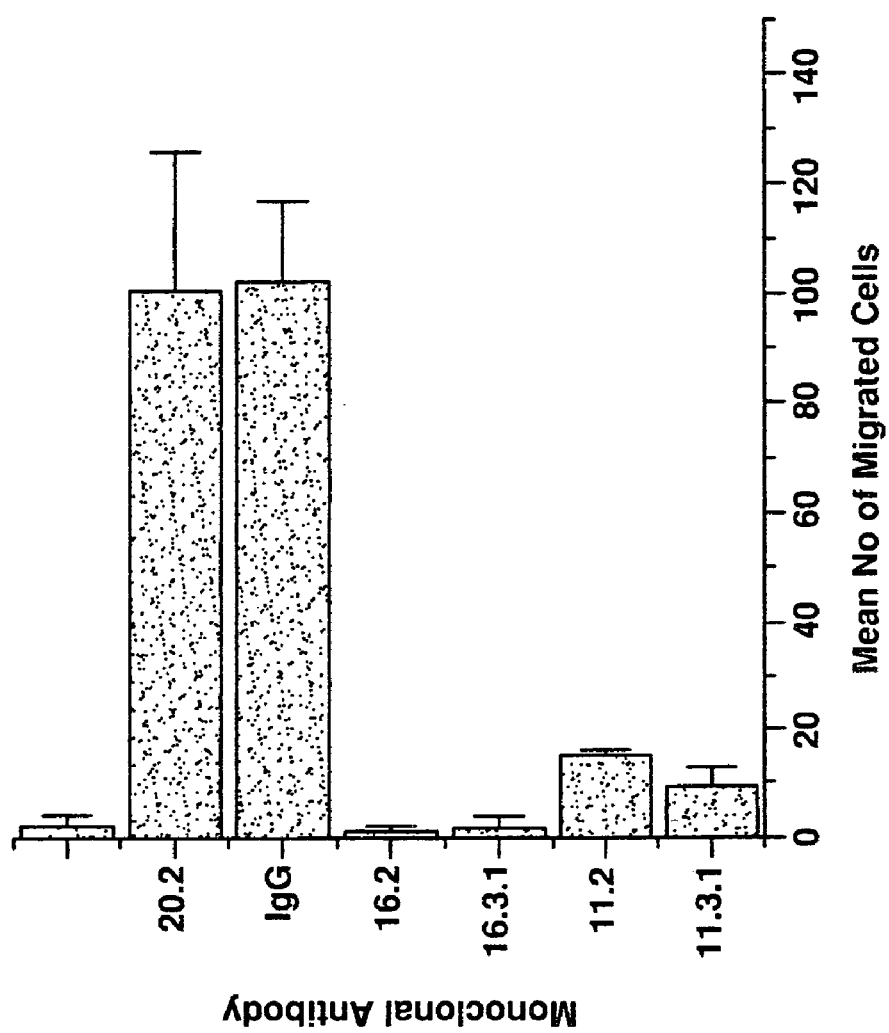

FIG. 19 is a histogram illustrating inhibition of TECK-induced chemotaxis of GPR-9-6/L1.2 transfectants by mAbs that bind to TECK. TECK was diluted (final concentration about 150 nM) in culture media containing a control IgG1 mAb (20 mg/ml) or diluted in conditioned culture media of hybridomas which produce mAbs that bind TECK. The TECK solutions were placed in the bottom of a Transwell plate and incubated at room temperature for 10 minutes. GPR-9-6/L1.2 transfectants were then suspended in culture media and placed in the inserts, which were placed into the wells of the plate. Monoclonal antibodies produced by murine hybridomas 11.2, 11.3.1, 16.2 and 16.3.1 (mAb 11.2, mAb 11.3.1, mAb 16.2 and mAb 16.3.1, respectively) inhibited TECK-induced chemotaxis. The antibody produced by murine hybridoma 20.2, which also binds TECK, and non specific IgG did not inhibit TECK-induced chemotaxis of GPR-9-6/L1.2 transfectants. Background chemotaxis (-) was assessed in assays where no TECK was added.

FIG. 20 illustrates a nucleotide sequence encoding human (Homo sapiens) TECK (SEQ ID NO:8). The sequence has an open-reading frame that begins at position 1, and the y at position 311 can be a pyrimidine (cytosine (c), thymine (t)). The nucleotide sequence deposited in Genbank under Accession Number U86358, that encodes human TECK, has a thymine at position 311 and an open-reading frame beginning at position 1.

FIG. 21 illustrates the amino acid sequence of human TECK protein (SEQ ID NO:9) encoded by the nucleotide sequence shown in FIG. 20 (SEQ ID NO:8). The X at position 104 can be a methionine residue (Met, M) or a threonine residue (Thr, T). The nucleotide sequence deposited in Genbank under Accession Number U86358 encodes a TECK having a methionine residue at position 104.

FIG. 22 illustrates a nucleotide sequence encoding a variant of human (Homo sapiens) TECK (SEQ ID NO:10) in which amino acid residue 109 (alanine 109) is deleted. The sequence has an open-reading frame that begins at position 1, and the y at position 311 can be a pyrimidine (cytosine (c), thymine (t)).

FIG. 23 illustrates the amino acid sequence of human TECK protein (SEQ ID NO:11) encoded by the nucleotide sequence shown in FIG. 22 (SEQ ID NO:10). The X at position 104 can be a methionine residue (Met, M) or a threonine residue (Thr, T).

Figure 24A:
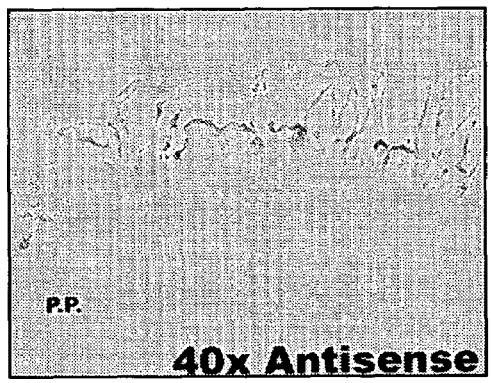
Figure 24C:
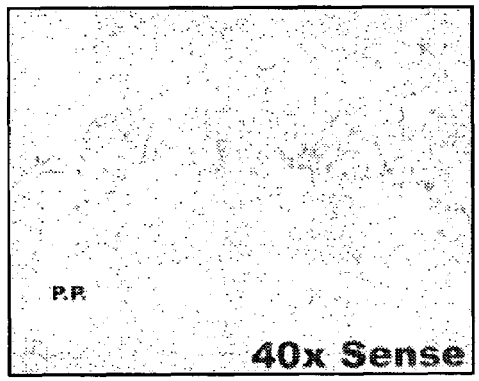
Figure 24B:
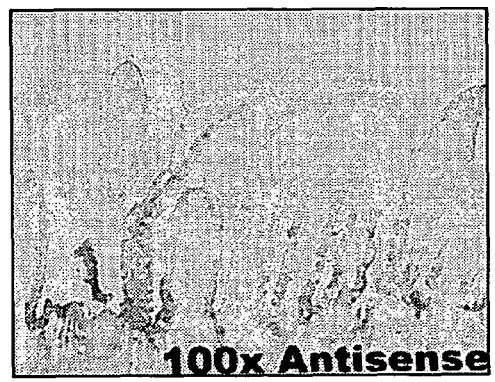

FIGS. 24A-24C are photographs of sections of mouse small intestine hybridized with an antisense TECK probe (FIGS. 24A and 24B) or a sense TECK probe (negative control, FIG. 24C). TECK expression was localized to the epithelium on the villi and crypts of Lieberkuhn. TECK expression was greatest at the base of the villli and lower levels of TECK hybridization was detected at the top of the villi (FIGS. 24A and 24B). No expression of TECK was detected in the Peyer's patches attached to the small intestine.

DETAILED DESCRIPTION OF THE INVENTION

Abbreviations used herein include: ECV304, human umbilical vein endothelial cell line (ATCC Accession No. CRL-1998); ADEC, adenoid expressed chemokine; IP10, IFN-gamma-inducible 10 kDa protein; IMDC, immature dendritic cell; I-TAC, interferon-inducible T cell alpha chemoattractant; MCP-1, monocyte chemoattractant protein; SDF, stromal cell derived factor; MDC, mature dendritic cell chemokine; MIG, monokine induced by interferon-gamma; RANTES, regulated on activation normal T cell expressed; MIP3, macrophage inflammatory protein 3; MIP4, macrophage inflammatory protein 4; TECK, thymus expressed chemokine; SLC, secondary lymphoid-tissue chemokine; DC, dendritic cell.

Chemokines and their receptors constitute an important component in the regulation of directed leukocyte migration. Chemokines are produced at sites of inflammation and attract various leukocytes bearing the corresponding receptors. While the spectrum of chemokines expressed at the inflammatory site can differentially attract certain inflammatory cells, selectivity and variation in chemokine receptor expression on leukocytes provides further regulation to ensure appropriate cell recruitment in response to particular inflammatory stimuli. As the number of identified and characterized chemokine receptors continues to grow, it is becoming increasingly clear that cells selectively express several receptors which may identify, mark, or otherwise characterize functional subsets of leukocytes such as $T_H1$ and $T_H2$, naive and memory, activated and quiescent T cells. Because several characterized and/or orphan chemokine receptors can be co-expressed on individual cells, it has been difficult to validate the role of specific receptors in the initiation and progression of disease or, for that matter, in normal immune function.

As described herein, a study of the orphan chemokine receptor GPR-9-6 was conducted. In the course of the study an antibody which binds human GPR-9-6 (mAb 3C3) was produced and used to analyze the expression and function of the receptor on various types of leukocytes. The receptor was found to be expressed predominantly on thymocytes and $\alpha 4\beta 7^{hi}$ CD4$^+$ memory lymphocytes which home to mucosal sites (e.g., respiratory tract, urogenital tract, alimentary canal and associated tissues (pancreas, gallbladder). As described herein, GPR-9-6 (CCR9) is a functional CC chemokine receptor which binds and is activated by the CC chemokine known as thymus-expressed chemokine (TECK).

The invention relates to the chemokine receptor GPR-9-6 and to agents (e.g., ligands, antibodies, antagonists, agonists) which bind to the receptor. In one aspect, the invention relates to an antibody which binds to mammalian GPR-9-6 or a portion of GPR-9-6.

Antibodies and Antibody Producing Cells

The antibody of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of human, chimeric, humanized, primatized, veneered or single chain antibodies. Functional fragments include antigen-binding fragments which bind to a mammalian GPR-9-6. For example, antibody fragments capable of binding to a mammalian GPR-9-6 or portions thereof, including, but not limited to Fv, Fab, Fab' and F(ab')$_2$ fragments are encompassed by the invention. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, *Gene*, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for mammalian (e.g., human) GPR-9-6 can be raised against an appropriate immunogen, such as isolated and/or recombinant human GPR-9-6 or portions thereof (including synthetic molecules, such as synthetic peptides). Antibodies can also be raised by immunizing a suitable host (e.g., mouse) with cells that express GPR-9-6, such as thymocytes. In addition, cells expressing a recombinant mammalian GPR-9-6 such as transfected cells, can be used as immunogens or in a screen for antibody which binds receptor (See e.g., Chuntharapai et al., *J. Immunol.*, 152: 1783-1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood, or preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies. Transgenic animals capable of producing a repertoire of human antibodies (e.g., XenoMouse (Abgenix, Fremont, Calif.) can be produced using suitable methods (see e.g., Jakobovits et al., *Proc. Natl. Acad. Sci. USA,* 90: 2551-2555 (1993); Jakobovits et al., *Nature,* 362: 255-258 (1993); Lonberg et al., U.S. Pat. No. 5,545,806; Surani et al., U.S. Pat. No. 5,545,807; Lonberg et al., WO97/13852).

In one embodiment, the antibody or antigen-binding fragment thereof has binding specificity for a mammalian GPR-9-6, preferably a naturally occurring or endogenous human GPR-9-6. In another embodiment, the antibody is an IgG or antigen-binding fragment of an IgG. In another embodiment, the antibody or antigen-binding fragment can bind to a mammalian GPR-9-6 and inhibit (reduce or prevent) one or more functions of the receptor. In a preferred embodiment, the antibody or antigen-binding fragment can inhibit binding of a ligand (i.e., one or more ligands) to the receptor, and/or one or more functions mediated by GPR-9-6 in response to ligand binding.

In a particular embodiment, the antibody or antigen-binding fragment can inhibit the binding of a mammalian (e.g., human) TECK to mammalian (e.g., human) GPR-9-6 and/or one or more functions mediated by GPR-9-6 in response to TECK binding. In a particularly preferred embodiment, the antibody or antigen-binding fragment can inhibit the binding of TECK to GPR-9-6 and, thereby inhibit TECK-induced chemotaxis.

Figure 9A:
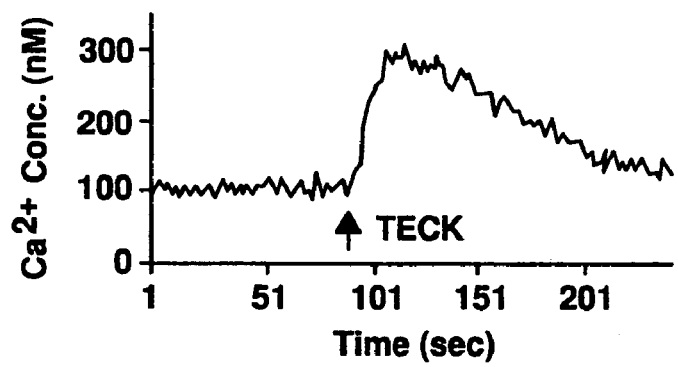
FIGS. 9A-9C illustrate that GPR-9-6 expressing cell lines undergo $Ca^{2+}$ flux in response to TECK. The GPR-9-6 expressing cell line MOLT-4 was loaded with the $Ca^{2+}$ sensitive dye Fura-2 and then tested for their ability to mobilize $Ca^{2+}$ in response to 150 nM TECK (FIG. 9A), 100 nM SDF1α (FIG. 9B) or 100 nM MDC (FIG. 9C) chemokines (n=2).

As shown herein, TECK is a ligand for GPR-9-6 and activates the receptor leading to TECK-induced $Ca^{2+}$ flux in cells that express GPR-9-6 (FIG. 9A). Cells that express mammalian GPR-9-6, including recombinant cells, can also undergo TECK-induced chemotaxis (FIGS. 8A-8D, 8F, 10, 11-11B and 13A-13B). Other functions which can be mediated by GPR-9-6 in response to ligand binding (e.g., TECK) include, for example, signal transduction (e.g., GDP/GTP exchange by GPR-9-6 associated G proteins, transient increase in the concentration of cytosolic free calcium $[Ca^{2+}]_i$) and GPR-9-6-mediated processes and cellular responses (e.g., proliferation, migration, chemotaxis, secretion, degranulation, inflammatory mediator release (such as release of bioactive lipids such as leukotrienes (e.g., leukotriene $C_4$)), respiratory burst).

In another embodiment, the binding of the antibody or antigen-binding fragment thereof to mammalian (e.g., human) GPR-9-6 can be inhibited by a peptide that consists of the amino acid sequence of SEQ ID NO:3.

As described herein, an antibody designated "mAb 3C3" that binds human GPR-9-6 has been produced. mAb 3C3 can be produced by murine hybridoma 3C3, also referred to as murine hybridoma LS129-3C3-E3-1 which was deposited on Mar. 4, 1999, on behalf of LeukoSite, Inc., 215 First Street, Cambridge, Mass. 02142, U.S.A., (now Millennium Pharmaceuticals, Inc., 75 Sidney Street, Cambridge, Mass. 01239), at the American Type Culture Collection, 10801 University Boulevard, Manassas, Va. 20110, U.S.A., under Accession No. HB-12653. In another embodiment, the anti-GPR-9-6 antibody of the invention is mAb 3C3 or an antigen-binding fragment thereof. In another embodiment, the binding of the antibody or antigen-binding fragment to mammalian (e.g., human) GPR-9-6 can be inhibited by mAb 3C3. Such inhibition can be the result of competition for the same or similar epitope, steric interference or due to a change in the conformation of GPR-9-6 that is induced upon antibody binding to the receptor. In still another embodiment, the antibody or antigen-binding fragment of the invention has the same or similar epitopic specificity as mAb 3C3. Antibodies with an epitopic specificity which is the same as or similar to that of mAb 3C3 can be identified by a variety of suitable methods. For example, an antibody with the same or similar epitopic specificity as mAb 3C3 can be identified based upon the ability to compete with mAb 3C3 for binding to mammalian GPR-9-6. In another example, the binding of mAb 3C3 and the binding of an antibody with the same or similar epitopic specificity to mammalian GPR-9-6 can be inhibited by a single peptide (e.g., natural peptide, synthetic peptide). The peptide can comprise nine to about fifty amino acids. Preferably, the peptide comprises nine to about twenty-six amino acids. In still another example, an antibody with the same or similar epitopic specificity as mAb 3C3 can be identified using chimeric receptors (see e.g., Rucker et al., *Cell* 87:437-446 (1996)).

As described herein, an antibody designated "mAb GPR96-1" that binds human GPR-9-6 has been produced. mAb GPR96-1 can be produced by murine hybridoma GPR96-1, also referred to as murine hybridoma LS272 GPR96 1-5, which was deposited on Mar. 9, 2000, on behalf of LeukoSite, Inc., 215 First Street, Cambridge, Mass. 02142, U.S.A., (now Millennium Pharmaceuticals, Inc., 75 Sidney Street, Cambridge, Mass. 01239), at the American Type Culture Collection, 10801 University Boulevard, Manassas, Va. 20110, U.S.A., under Accession No. PTA-1470. In another embodiment, the anti-GPR-9-6 antibody of the invention is mAb GPR96-1 or an antigen-binding fragment thereof. In another embodiment, the binding of the antibody or antigen-binding fragment to mammalian (e.g., human) GPR-9-6 can be inhibited by mAb GPR96-1. Such inhibition can be the result of competition for the same or similar epitope, steric interference or due to a change in the conformation of GPR-9-6 that is induced upon antibody binding to the receptor. In still another embodiment, the antibody or antigen-binding fragment of the invention has the same or similar epitopic specificity as mAb GPR96-1. Antibodies with an epitopic specificity which is the same as or similar to that of mAb GPR96-1 can be identified by a variety of suitable methods, such as those described herein.

The invention also relates to a bispecific antibody, or functional fragment thereof (e.g., $F(ab')_2$), which binds to a mammalian GPR-9-6 and at least one other antigen. In a particular embodiment, the bispecific antibody, or functional fragment thereof has the same or similar epitopic specificity as mAb 3C3 or mAb GPR96-1 and at least one other antibody (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In a preferred embodiment, the antibody or antigen-binding fragment of the invention specifically binds to a mammalian GPR-9-6. As used herein the term "specific antibody" or "specific" when referring to an antibody-antigen interaction is used to indicate that the antibody can selectively bind to a mammalian GPR-9-6, rather than to indicate that the antibody can bind to only one antigen. For example, an antibody may bind to one or several antigens with low affinity and bind to human GPR-9-6 with a high affinity. Such an antibody is considered to be specific for human GPR-9-6 because when used (e.g., in therapeutic or diagnostic application) at a suitable concentration, the antibody can selectively bind to human GPR-9-6. The concentration of antibody required to provide selectivity for a mammalian GPR-9-6 (e.g., a concentration which reduces or eliminates low affinity binding) can be readily determined by suitable methods, for example, titration.

In another aspect, the invention relates to an isolated cell which produces an antibody or an antigen-binding fragment of an antibody that binds to a mammalian GPR-9-6. In a preferred embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-GPR-9-6 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a sequence encoding a rearranged anti-GPR-9-6 light and/or heavy chain can be isolated (e.g., by PCR) or cDNA libraries can be prepared from mRNA isolated from the cell lines, and cDNA clones encoding an anti-GPR-9-6 immunoglobulin chain(s) can be isolated. Thus, nucleic acids encoding the heavy and/or light chains of the antibodies or portions thereof can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell.

The antibody of the invention can be produced by any suitable method, for example, by collecting serum from an animal (e.g., mouse, human, transgenic mouse) which has been immunized with a mammalian GPR-9-6. In another example, a suitable antibody producing cell (e.g., hybridoma, heterohybridoma, lymphoblastoid cell, recombinant cell) can be maintained, either in vitro or in vivo, under conditions suitable for expression (e.g., in the presence of inducer, suitable media supplemented with appropriate salts, growth factors, antibiotic, nutritional supplements), whereby the antibody or antigen-binding fragment is produced. If desired, the antibody or antigen-binding fragment can be recovered and/or isolated (e.g., from the host cells, culture medium) and purified to the desired degree. Recovery and purification of the antibody can be achieved using suitable methods, such as, centrifugation, filtration, column chromatography (e.g., ion-exchange, gel filtration, hydrophobic-interaction, affinity), preparative native electrophoresis, precipitation and ultrafiltration. It will be appreciated that the method of production encompasses expression in a host cell of a transgenic animal (see e.g., WO 92/03918, GenPharm International, published Mar. 19, 1992).

As described herein, antibodies and functional fragments thereof of the present invention can inhibit (reduce or prevent) binding of a ligand to a mammalian GPR-9-6 and/or inhibit one or more functions associated with binding of the ligand to GPR-9-6. As discussed below various methods can be used to assess inhibition of binding of a ligand to GPR-9-6 and/or function associated with binding of the ligand to the receptor.

Anti-TECK Antibodies

In another aspect, the antibody or antigen-binding fragment thereof has binding specificity for a mammalian TECK, preferably a naturally occurring or endogenous human TECK. In one embodiment, the antibody is an IgG or antigen-binding fragment of an IgG. In another embodiment, the antibody or antigen-binding fragment can bind to a mammalian TECK and inhibit (reduce or prevent) binding of TECK to receptor (e.g., GPR-9-6 (CCR9)), and/or one or more functions mediated by receptor in response to TECK binding.

In a particular embodiment, the antibody or antigen-binding fragment can inhibit the binding of a mammalian (e.g., human) TECK to mammalian (e.g., human) GPR-9-6 (CCR9) and/or one or more functions mediated by GPR-9-6 (CCR9) in response to TECK binding. In a particularly preferred embodiment, the antibody or antigen-binding fragment can inhibit the binding of TECK to GPR-9-6 (CCR9) and, thereby inhibit TECK-induced chemotaxis.

As described herein, an antibody designated "mAb 11.3.1" that binds human TECK has been produced. mAb 11.3.1 can be produced by murine hybridoma 11.3.1, also referred to as murine hybridoma LS250 11.3.1, which was deposited on Mar. 9, 2000, on behalf of LeukoSite, Inc., 215 First Street, Cambridge, Mass. 02142, U.S.A., (now Millennium Pharmaceuticals, Inc., 75 Sidney Street, Cambridge, Mass. 01239), at the American Type Culture Collection, 10801 University Boulevard, Manassas, Va. 20110, U.S.A., under Accession No. PTA-1469. In another embodiment, the anti-TECK antibody of the invention is mAb 11.3.1 or an antigen-binding fragment thereof. In another embodiment, the binding of the antibody or antigen-binding fragment to mammalian (e.g., human) TECK can be inhibited by mAb 11.3.1. Such inhibition can be the result of competition for the same or similar epitope, steric interference or due to a change in the conformation of TECK that is induced upon antibody binding to the receptor. In still another embodiment, the antibody or antigen-binding fragment of the invention has the same or similar epitopic specificity as mAb 11.3.1. Antibodies with an epitopic specificity which is the same as or similar to that of mAb 11.3.1 can be identified by a variety of suitable methods. For example, an antibody with the same or similar epitopic specificity as mAb 11.3.1 can be identified based upon the ability to compete with mAb 11.3.1 for binding to mammalian TECK. In another example, the binding of mAb 11.3.1 and the binding of an antibody with the same or similar epitopic specificity to mammalian TECK can be inhibited by a single peptide (e.g., natural peptide, synthetic peptide). The peptide can comprise nine to about fifty amino acids. Preferably, the peptide comprises nine to about twenty-six amino acids. In still another example, an antibody with the same or similar epitopic specificity as mAb 11.3.1 can be identified using chimeric receptors (see e.g., Rucker et al., Cell 87:437-446 (1996)).

As described herein, an antibody designated "mAb 16.3.1" that binds human TECK has been produced. mAb 16.3.1 can be produced by murine hybridoma 16.3.1, also referred to as murine hybridoma LS250 16.3.1, which was deposited on Mar. 9, 2000, on behalf of LeukoSite, Inc., 215 First Street, Cambridge, Mass. 02142, U.S.A., (now Millennium Pharmaceuticals, Inc., 75 Sidney Street, Cambridge, Mass. 01239), at the American Type Culture Collection, 10801 University Boulevard, Manassas, Va. 20110, U.S.A., under Accession No. PTA-1468. In another embodiment, the anti-TECK antibody of the invention is mAb 16.3.1 or an antigen-binding fragment thereof. In another embodiment, the binding of the antibody or antigen-binding fragment to mammalian (e.g., human) TECK can be inhibited by mAb 16.3.1. Such inhibition can be the result of competition for the same or similar epitope, steric interference or due to a change in the conformation of TECK that is induced upon antibody binding. In still another embodiment, the antibody or antigen-binding fragment of the invention has the same or similar epitopic specificity as mAb 16.3.1. Antibodies with an epitopic specificity which is the same as or similar to that of mAb 16.3.1 can be identified by a variety of suitable methods, such as those described herein.

The invention also relates to a bispecific antibody, or functional fragment thereof (e.g., F(ab')$_2$), which binds to a mammalian TECK and at least one other antigen. In a particular embodiment, the bispecific antibody, or functional fragment thereof has the same or similar epitopic specificity as mAb 11.3.1 or mAb 16.3.1 and at least one other antibody (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)). Preferably, the antibody or antigen-binding fragment specifically binds to a mammalian TECK.

In another aspect, the invention relates to an isolated cell which produces an antibody or an antigen-binding fragment of an antibody that binds to a mammalian TECK. In a preferred embodiment, the isolated antibody-producing cell of the invention is an immortalized cell, such as a hybridoma, heterohybridoma, lymphoblastoid cell or a recombinant cell.

The anti-TECK antibody of the invention can be produced by any suitable method, for example, by collecting serum from an animal (e.g., mouse, human, transgenic mouse) which has been immunized with a mammalian TECK. In another example, a suitable antibody producing cell (e.g., hybridoma, heterohybridoma, lymphoblastoid cell, recombinant cell) can be maintained, either in vitro or in vivo, under conditions suitable for expression (e.g., in the presence of inducer, suitable media supplemented with appropriate salts, growth factors, antibiotic, nutritional supplements), whereby the antibody or antigen-binding fragment is produced. If desired, the antibody or antigen-binding fragment can be recovered and/or isolated (e.g., from the host cells, culture medium) and purified to the desired degree. Recovery and purification of the antibody can be achieved using suitable methods, such as, centrifugation, filtration, column chromatography (e.g., ion-exchange, gel filtration, hydrophobic-interaction, affinity), preparative native electrophoresis, precipitation and ultrafiltration. It will be appreciated that the method of production encompasses expression in a host cell of a transgenic animal (see e.g., WO 92/03918, GenPharm International, published Mar. 19, 1992).

As described herein, antibodies and functional fragments thereof of the present invention can inhibit (reduce or prevent) binding of mammalian TECK to a receptor and/or inhibit one or more functions associated with binding of TECK to receptor. As discussed below various methods can be used to assess inhibition of binding of TECK to a receptor and/or function associated with binding of the ligand to the receptor.

The antibodies and antigen-binding fragments of the invention can be directly or indirectly bonded to another diagnostic or therapeutic agent (e.g., drug (e.g., cytotoxic agent), therapeutic proteins (e.g., cytokines, growth factors), radionuclide) through a variety of suitable linkages. Thus, the invention provides antigen-binding fusion proteins and immunoconjugates. For example, when the additional diagnostic or therapeutic agent is a protein or peptide, the antibody or antigen-binding fragment and the additional agent can be part of a contiguous polypeptide (i.e., a fusion protein). In such a fusion protein, the antibody or antigen-binding fragment and additional agent can be arranged on the polypeptide in any suitable configuration. The antibody or antigen-binding fragment and additional agent can be indirectly bonded through a (i.e., one or more) peptide linker, or bonded directly to each other through a peptide bond. For example, the amino acid sequence of a therapeutic protein or peptide (e.g., a cytokine or chemokine) can be fused to the amino-terminus or the carboxyl terminus of an Fv. The sequence of the therapeutic protein or peptide can also serve as a spacer or be inserted into a spacer which connects the variable regions (heavy chain variable region, light chain variable region) of the Fv.

Where the antibody or antigen-binding fragment and additional agent are not part of a contiguous polypeptide (e.g., an immunoconjugate) they can be directly bonded by a chemical bond (e.g., covalent bond) formed by reaction of a functional group (or activated derivative thereof) on the antibody or antigen-binding fragment with a second functional group (or activated derivative thereof) on the additional agent. For example, two thiols can react to form a disulfide bond and an amine can react with a carboxylic acid or acyl halide to form an amide. A variety of other suitable reactions which can be used are known in the art (see, for example, Hermanson, G. T., *Bioconjugate Techniques*, Academic Press: San Diego, Calif. (1996)). The antibody or antigen-binding fragment and additional agent can be indirectly bonded through a suitable linker (e.g., a peptide linker). Generally, a linker contains two reactive groups which can react to form a bond with the antibody and a bond with the additional agent. Linkers which contain two different reactive groups (e.g., a heterobifunctional linker) can be used to selectively conjugate the antibody or antigen-binding fragment to the additional agent. Many linkers which are suitable for forming conjugates between proteins, nucleic acids, peptides, vitamins, sugars, lipids, small organic molecules and other suitable agents are known (see, for example, U.S. Pat. Nos. 5,856,571, 5,880,270; Hermanson, G. T., *Bioconjugate Techniques*, Academic Press: San Diego, Calif. (1996)).

Preferably, the independent activities of the components of the antigen-binding fusion proteins and immunoconjugates (e.g., antibody, cytotoxic agent) are not significantly different from the activities of the components as separate molecular entities. For example, where the antibody or antigen-binding fragment binds GPR-9-6, the immunoconjugate can bind to GPR-9-6 with an affinity which is within a factor of about 1000, preferably within a factor of 100, more preferably within a factor of 10 or substantially the same as the affinity of the free antibody or antigen-binding fragment.

In one embodiment, the immunoconjugate comprises a suitable cytotoxic agent which is bonded to an antibody which binds mammalian GPR-9-6 (e.g., human GPR-9-6) or antigen-binding fragment thereof through a linker. The linker can form a bond with specific sites on the antibody and/or cytotoxic agent. For example, the linker can be bonded to the side chain of cysteinyl residues, the side chain of lysine residues or the side chains of aspartyl or glutamyl residues of the antibody or antigen-binding fragment. Suitable cytotoxic agents which can be conjugated to antibodies include, for example, chemotherapeutic agents (e.g., mitomycin C, methotrexate, 5-fluorouracil, cyclohexamine), and toxins such as ricin, gelonin and the like.

In another embodiment, the invention provides an antigen-binding fusion protein comprising an antibody or antigen-binding fragment thereof (e.g., Fab, Fab', F(ab)'$_2$, Fv) which binds to a mammalian GPR-9-6 and a protein or peptide that can activate and/or attract cytotoxic cells (e.g., cytotoxic T cells, NK cells). A number of proteins and peptides that can activate and/or attract cytotoxic cells, such as interleukin-12 and the chemokines 6Ckine (also referred to as SLC, Exodus2, TCA) and Ckbeta-11 (also referred to as M3beta, ELC) are known in the art (see, for example, Kim C. H. et al., *Cell. Immunol.*, 193:226-235 (1999); Pham-Nguyen K. B. et al., *Int. J. Cancer*, 81:813-819 (1999)). Several suitable methods for preparing fusion proteins are known in the art, for example, the fusion protein can be prepared using the methods described in U.S. Pat. Nos. 5,767,260, 5,824,782 and 5,889,157, or other suitable methods. The entire teachings of U.S. Pat. Nos. 5,767,260, 5,824,782 and 5,889,157 are incorporated herein by reference.

Binding Assays

The invention also relates to methods for detecting or identifying an agent (i.e., molecule or compound) which can bind to a mammalian GPR-9-6 or a ligand-binding variant thereof.

As used herein "mammalian GPR-9-6" refers to naturally occurring or endogenous mammalian GPR-9-6 proteins and to proteins having an amino acid sequence which is the same as that of a naturally occurring or endogenous corresponding mammalian GPR-9-6 protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian GPR-9-6 (e.g., produced by alternative splicing or other cellular processes), and modified or unmodified forms of the foregoing (e.g., lipidated, glycosylated, unglycosylated). Naturally occurring or endogenous mammalian GPR-9-6 proteins include wild type proteins such as mature GPR-9-6, polymorphic or allelic variants and other isoforms which occur naturally in mammals (e.g., humans, non-human primates). Such proteins can be recovered or isolated from a source which naturally produces mammalian GPR-9-6, for example. Polymorphic, allelic, splice and other naturally occurring variants of mammalian GPR-9-6 can be expressed in particular organs, tissues or cells and have altered properties (e.g., altered affinity for ligand (e.g. TECK)) and specialized biological function (e.g., T cell development, T cell recruitment). Naturally occurring or endogenous mammalian GPR-9-6 proteins and proteins having the same amino acid sequence as a naturally occurring or endogenous corresponding mammalian GPR-9-6, are referred to by the name of the corresponding mammal. For example, where the corresponding mammal is a human, the protein is designated as a human GPR-9-6 protein (e.g., a recombinant human GPR-9-6 produced in a suitable host cell).

"Functional variants" of mammalian GPR-9-6 proteins include functional fragments, functional mutant proteins, and/or functional fusion proteins which can be produced using suitable methods (e.g., mutagenesis (e.g., chemical mutagenesis, radiation mutagenesis), recombinant DNA techniques). A "functional variant" is a protein or polypeptide which has at least one function characteristic of a mammalian GPR-9-6 protein as described herein, such as a binding activity, a signaling activity and/or ability to stimulate a cellular response. Preferred functional variants can bind a ligand (i.e., one or more ligands, such as TECK).

Generally, fragments or portions of mammalian GPR-9-6 proteins include those having a deletion (i.e., one or more deletions) of an amino acid (i.e., one or more amino acids) relative to the mature mammalian GPR-9-6 protein (such as N-terminal, C-terminal or internal deletions). Fragments or portions in which only contiguous amino acids have been deleted or in which non-contiguous amino acids have been deleted relative to mature mammalian GPR-9-6 protein are also envisioned.

Mutant mammalian GPR-9-6 proteins include natural or artificial variants of a mammalian GPR-9-6 protein differing by the addition, deletion and/or substitution of one or more contiguous or non-contiguous amino acid residues (e.g., receptor chimeras). Such mutations can occur at one or more sites on a protein, for example a conserved region or nonconserved region (compared to other chemokine receptors or G-protein coupled receptors), extracellular region, cytoplasmic region, or transmembrane region.

Fusion proteins encompass polypeptides comprising a mammalian GPR-9-6 (e.g., human GPR-9-6) or a variant thereof as a first moiety, linked via a covalent bond (e.g., a peptide bond) to a second moiety not occurring in the mammalian GPR-9-6 as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human GPR-9-6 or a portion thereof. Additional (e.g., third, fourth) moieties can be present as appropriate.

In one embodiment, a functional variant of mammalian GPR-9-6 (e.g., a ligand binding variant) shares at least about 80% amino acid sequence similarity with said mammalian GPR-9-6, preferably at least about 90% amino acid sequence similarity, and more preferably at least about 95% amino acid sequence similarity with said mammalian GPR-9-6. In another embodiment, a functional fusion protein comprises a first moiety which shares at least about 85% sequence similarity with a mammalian GPR-9-6, preferably at least about 90% sequence similarity, and more preferably at least about 95% sequence similarity with a mammalian GPR-9-6 (e.g., a human GPR9-6 (e.g., SEQ ID NO:2)). In another embodiment, a functional mammalian GPR-9-6 protein or functional variant of a mammalian GPR-9-6 protein shares at least about 80% amino acid sequence similarity, preferably at least about 90% amino acid sequence similarity, and more preferably at least about 95% amino acid sequence similarity with a naturally occurring human GPR-9-6 (e.g., SEQ ID NO:2). Amino acid sequence similarity can be determined using a suitable sequence alignment algorithm, such as the LASERGENE® system (sequence assembly and alignment software; DNASTAR® Inc., Madison, Wis.), using the Clustal method with the PAM 250 residue weight table, a gap penalty of 10, a gap length penalty of 10 and default parameters (pairwise alignment parameters: ktuple=1, gap penalty=3, window=4 and diagonals saved=5). In another embodiment, a functional variant is encoded by a nucleic acid sequence which is different from the naturally-occurring nucleic acid sequence, but which, due to the degeneracy of the genetic code, encodes mammalian GPR-9-6 or a portion thereof.

As used herein "mammalian TECK" refers to naturally occurring or endogenous mammalian TECK proteins and to proteins having an amino acid sequence which is the same as that of a naturally occurring or endogenous corresponding mammalian TECK protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian TECK (e.g., produced by alternative splicing or other cellular processes), and modified or unmodified forms of the foregoing (e.g., lipidated, glycosylated, unglycosylated). Naturally occurring or endogenous mammalian TECK proteins include wild type proteins such as mature TECK, polymorphic or allelic variants and other isoforms which occur naturally in mammals (e.g., humans, non-human primates). Such proteins can be recovered or isolated from a source which naturally produces mammalian TECK, for example.

Polymorphic, allelic, splice and other naturally occurring variants of mammalian TECK can be expressed in particular organs, tissues or cells and have altered properties (e.g., altered affinity for receptor (e.g. GPR-9-6)) and specialized biological function (e.g., T cell development, T cell recruitment). For example, as described herein an alternatively spliced form of human TECK, in which the amino acid at position 110 (Ala 110) is deleted, is more prevalent in small intestine than thymus.

Naturally occurring or endogenous mammalian TECK proteins and proteins having the same amino acid sequence as a naturally occurring or endogenous corresponding mammalian TECK, are referred to by the name of the corresponding mammal. For example, where the corresponding mammal is a human, the protein is designated as a human TECK protein (e.g., a recombinant human TECK produced in a suitable host cell).

"Functional variants" of mammalian TECK proteins include functional fragments, functional mutant proteins, and/or functional fusion proteins which can be produce using suitable methods (e.g., mutagenesis (e.g., chemical mutagenesis, radiation mutagenesis), recombinant DNA techniques). A "functional variant" is a protein or polypeptide which has at least one function characteristic of a mammalian TECK protein as described herein, such as a binding activity, a signaling activity and/or ability to stimulate a cellular response. Preferred functional variants can bind a receptor (e.g., GPR-9-6 (CCR9)).

Generally, fragments or portions of mammalian TECK proteins include those having a deletion (i.e., one or more deletions) of an amino acid (i.e., one or more amino acids) relative to the mature mammalian TECK protein (such as N-terminal, C-terminal or internal deletions). Fragments or portions in which only contiguous amino acids have been deleted or in which non-contiguous amino acids have been deleted relative to mature mammalian TECK protein are also envisioned.

Mutant mammalian TECK proteins include natural or artificial variants of a mammalian TECK protein differing by the addition, deletion and/or substitution of one or more contiguous or non-contiguous amino acid residues. Such mutations can occur at one or more sites on a protein, for example a conserved region or nonconserved region (compared to other chemokines).

Fusion proteins encompass polypeptides comprising a mammalian TECK (e.g., human TECK) or a variant thereof as a first moiety, linked via a covalent bond (e.g., a peptide bond) to a second moiety not occurring in the mammalian TECK as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human TECK or a portion thereof. Additional (e.g., third, fourth) moieties can be present as appropriate.

In one embodiment, a functional variant of mammalian TECK (e.g., a ligand binding variant) shares at least about 80% amino acid sequence similarity with said mammalian TECK, preferably at least about 90% amino acid sequence similarity, and more preferably at least about 95% amino acid sequence similarity with said mammalian TECK (e.g., SEQ ID NO:9, SEQ ID NO:11). In another embodiment, a functional fusion protein comprises a first moiety which shares at least about 85% sequence similarity with a mammalian TECK, preferably at least about 90% sequence similarity, and more preferably at least about 95% sequence similarity with a mammalian TECK (e.g., a human TECK (e.g., SEQ ID NO:9, SEQ ID NO:11)). In another embodiment, a functional mammalian TECK protein or functional variant of a mammalian TECK protein shares at least about 80% amino acid sequence similarity, preferably at least about 90% amino acid sequence similarity, and more preferably at least about 95% amino acid sequence similarity with a naturally occurring human TECK (e.g., SEQ ID NO:9, SEQ ID NO:11). Amino acid sequence similarity can be determined using a suitable sequence alignment algorithm, such as the LASERGENE® system (sequence assembly and alignment software; DNASTAR® Inc., Madison, Wis.), using the Clustal method with the PAM 250 residue weight table, a gap penalty of 10, a gap length penalty of 10 and default parameters (pairwise alignment parameters: ktuple=1, gap penalty=3, window=4 and diagonals saved=5). In another embodiment, a functional variant is encoded by a nucleic acid sequence which is different from the naturally-occurring nucleic acid sequence, but which, due to the degeneracy of the genetic code, encodes mammalian TECK or a portion thereof The invention also relates to naturally occurring variants of mammalian GPR-9-6 and mammalian TECK (e.g., splice variants, allelic variants) and to nucleic acids encoding the variants (e.g., SEQ ID NO:10, SEQ ID NO:11).

A composition comprising a mammalian GPR-9-6 or functional variant thereof can be used in a binding assay to detect and/or identify agents that can bind to the receptor or to detect and/or identify agents that can bind to TECK. Compositions suitable for use in a binding assay include, for example, cells which naturally express a mammalian GPR-9-6 or functional variant thereof (e.g., thymocytes, GPR-9-

6+ CLA$^{-ve}$ α4β7$^{hi}$ CD4+ memory lymphocytes, cell lines (e.g., MOLT-4 (ATCC Accession No. CRL-1582), MOLT-13 (M. Brenner, Brigham and Women's Hospital, Boston, Mass.), intraepithelial lymphocytes (IEL), lamina propria lymphocytes (LPL)) and recombinant cells comprising an exogenous nucleic acid sequence which encodes a mammalian GPR-9-6 or functional variant thereof. Compositions suitable for use in a binding assay also include, membrane preparations which comprise a mammalian GPR-9-6 or functional variant thereof. Such membrane preparations can contain natural (e.g., plasma membrane) or synthetic membranes. Preferably, the membrane preparation is a membrane fraction of a cell that expresses a mammalian GPR-9-6 or a functional variant thereof.

In one embodiment, the method of detecting or identifying an agent that binds to a mammalian GPR-9-6 is a competitive binding assay in which the ability of a test agent to inhibit the binding of a reference agent (e.g., a ligand (e.g., TECK), an antibody) is assessed. For example, the reference agent can be labeled with a suitable label as described herein, and the amount of labeled reference agent required to saturate the GPR-9-6 present in the assay can be determined. A saturating amount of labeled reference agent and various amounts of a test agent can be contacted with a composition comprising a mammalian GPR-9-6 or functional variant thereof under conditions suitable for binding and complex formation determined.

The formation of a complex between the reference agent and the GPR-9-6 or functional variant thereof can be detected or measured directly or indirectly using suitable methods. For example, the agent can be labeled with a suitable label and the formation of a complex can be determined by detection of the label. The specificity of the complex can be determined using a suitable control such as unlabeled agent or label alone. Labels suitable for use in detection of a complex between an agent and a mammalian GPR-9-6 or functional variant thereof include, for example, a radioisotope, an epitope, an affinity label (e.g., biotin, avidin), a spin label, an enzyme, a fluorescent group or a chemiluminescent group. Where use of a label is undesirable, complex formation can be detected using other suitable methods, such as surface plasmon resonance.

The capacity of the test agent to inhibit the formation of a complex between the reference agent and a mammalian GPR-9-6 can be reported as the concentration of test agent required for 50% inhibition (IC$_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian GPR-9-6 or a functional variant thereof, for example, a ligand of GPR-9-6 (e.g., TECK) or an antibody. In a preferred embodiment, the reference agent is mAb 3C3 or mAb GPR96-1. In a particularly preferred embodiment, the reference agent is a mammalian (e.g., human) TECK.

The invention also relates to a method for detecting or identifying an agent that binds to a mammalian TECK. In one embodiment, the method for detecting or identifying an agent that binds to a mammalian TECK is a competitive binding assay in which the ability of a test agent to inhibit the binding of TECK or a functional variant thereof to a TECK-binding reference agent (e.g., receptor (e.g. GPR-9-6 (CCR9), antibody) is assessed. For example, TECK (e.g., human TECK) can be labeled with a suitable label as described herein, and the amount of labeled TECK required to saturate the GPR-9-6 present in an assay can be determined. A saturating amount of labeled TECK and various amounts of a test agent can be contacted with a composition comprising a mammalian GPR-9-6 or functional variant thereof under conditions suitable for binding and complex formation determined. The formation of a complex between TECK and the GPR-9-6 or functional variant thereof can be detected or measured directly or indirectly using suitable methods. For example, TECK can be labeled with a suitable label and the formation of a complex can be determined by detection of the label. The specificity of the complex can be determined using a suitable control such as unlabeled TECK or label alone. Labels suitable for use in detection of a complex between TECK and a mammalian GPR-9-6 or functional variant thereof include, for example, a radioisotope, an epitope, an affinity label (e.g., biotin, avidin), a spin label, an enzyme, a fluorescent group or a chemiluminescent group. Where use of a label is undesirable, complex formation can be detected using other suitable methods, such as surface plasmon resonance.

The capacity of the test agent to inhibit the formation of a complex between TECK and a reference reagent (e.g., mammalian GPR-9-6 (CCR9)) can be reported as the concentration of test agent required for 50% inhibition (IC$_{50}$ values) of specific binding of labeled reference agent, as described above.

The invention also relates to a method of identifying or isolating an agent (i.e., molecule or compound) which can be used in therapy, as described herein. In one embodiment, the agent is identified or isolated in a competitive binding assay as described above. In another embodiment, cells which express a mammalian GPR-9-6 or a functional variant thereof are maintained under conditions appropriate for expression of receptor. The cells are contacted with an agent (e.g., ligand, antagonist, agonist) under conditions suitable for binding (e.g., in a suitable binding buffer), and the formation of a complex between the agent and a mammalian GPR-9-6 is detected or measured using suitable techniques. For example, the agent can be labeled as described herein and the amount of label present in an agent-GPR-9-6 complex can be determined. The extent of complex formation can be determined relative to a suitable control (e.g., compared with background determined in the absence of agent, compared with binding of a second agent (i.e., a standard, an isotype control), compared with binding of agent to cells that do not express GPR-9-6).

Thus, the invention relates to a method of identifying or isolating an agent for use in treating a subject having an inflammatory disease. In particular embodiments, the method is a method of identifying or isolating an agent for use in treating a subject having an inflammatory disease associated with mucosal tissue, such as Crohn's disease or colitis. In another embodiment, the method is a method of identifying or isolating an agent for use in inhibiting GPR-9-6-mediated homing of leukocytes in a subject. In another embodiment, the method is a method of identifying or isolating an agent for use in modulating a GPR-9-6 function in a subject.

The invention also relates to a method of identifying or isolating an agent for use in treating a subject having cancer (e.g., acute or chronic leukemia (e.g., acute T-cell lymphoblastic leukemia, acute B-cell lymphoblastic leukemia, chronic T-cell lymphoblastic leukemia, chronic B-cell lymphoblastic leukemia), lymphoma (e.g., Hodgkin's disease, T cell lymphoma), carcinoma (e.g., breast (e.g., ductal carcinoma, lobular carcinoma), ovarian, testicular, prostatic, squamous cell, basal cell), melanoma, myeloma, adenoma). In particular embodiments, the method is a method of identifying or isolating an agent for use in treating a subject having leukemia (e.g., acute lymphoblastic leukemia (e.g., acute T-cell lymphoblastic leukemia, acute B-cell lymphoblastic leukemia), chronic lymphoblastic leukemia e.g., chronic T-cell lymphoblastic leukemia, chronic B-cell lymphoblastic leukemia)).

Agents can be individually screened or one or more agents can be tested simultaneously according to the methods described herein. Where a mixture of compounds is tested, the compounds selected by the processes described can be separated (as appropriate) and identified by suitable methods (e.g., sequencing, chromatography). The presence of one or more compounds (e.g., a ligand, inhibitor, promoter) in a test sample can also be determined according to these methods.

Agents which bind to a mammalian GPR-9-6 or mammalian TECK and which are useful in the therapeutic methods described herein can be identified, for example, by screening libraries or collections of molecules, such as, the Chemical Repository of the National Cancer Institute, in assays described herein or using other suitable methods. Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678-2685 (1994) and references cited therein; see also, Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods can be accomplished. In one embodiment, the collection of agents tested according to the method of the invention does not comprise chemokines or mutants or analogues thereof.

Functional Assays

An agent which binds a mammalian GPR-9-6 or a functional variant thereof can be further studied in one or more suitable assays to determine if said agent can modulate (inhibit (reduce or prevent) or promote) one or more functions of GPR-9-6 as described herein. For example, an agent can be tested in an extracellular acidification assay, calcium flux assay, ligand binding assay, chemotaxis assay or assay which monitors degranulation or inflammatory mediator release (see, for example, Hesselgesser et al., *J. Biol. Chem.* 273(25):15687-15692 (1998) and WO 98/02151).

For example, an agent which binds to a mammalian GPR-9-6 can be tested in a leukocyte chemotaxis assay using suitable cells. Suitable cells include, for example, cell lines, recombinant cells or isolated cells which express a mammalian GPR-9-6 and undergo GPR-9-6 ligand-induced (e.g., TECK-induced) chemotaxis. In one example, GPR-9-6-expressing recombinant L1.2 cells (see Campbell, et al. *J. Cell Biol*, 134:255-266 (1996) regarding L1.2 cells), can be used in a modification of a transendothelial migration assay (Carr, M. W., et al. T. A., *Proc. Natl Acad Sci, USA*, (91):3652 (1994)). The endothelial cells used in this assay are preferably the endothelial cell line, ECV 304, which can be obtained from the American Type Culture Collection (Manassas, Va.). Endothelial cells can be cultured on 6.5 mm diameter Transwell culture inserts (Costar Corp., Cambridge, Mass.) with 3.0 µm pore size. Culture media for the ECV 304 cells can consist of M199+10% FCS, L-glutamine, and antibiotics. The assay media can consist of equal parts RPMI 1640 and M199 with 0.5% BSA. Two hours before the assay, $2\times10^5$ ECV 304 cells can be plated onto each insert of the 24 well Transwell chemotaxis plate and incubated at 37° C. Chemotactic factor such as TECK (Peprotech, Rocky Hill, N.J.) (diluted in assay medium) can be added to the 24-well tissue culture plates in a final volume of 600 µL. Endothelial-coated Transwells can be inserted into each well and $10^6$ cells of the leukocyte type being studied are added to the top chamber in a final volume of 100 µL of assay medium. The plate can then be incubated at 37° C. in 5% $CO_2$/95% air for 1-2 hours. The cells that migrate to the bottom chamber during incubation can be counted, for example using flow cytometry. To count cells by flow cytometry, 500 µL of the cell suspension from the lower chamber can be placed in a tube and relative counts can be obtained for a set period of time, for example, 30 seconds. This counting method is highly reproducible and allows gating on the leukocytes and the exclusion of debris or other cell types from the analysis. Alternatively, cells can be counted with a microscope. Assays to evaluate agents that can inhibit or promote chemotaxis can be performed in the same way as control experiment described above, except that agent solutions, in assay media containing up to 1% of DMSO co-solvent, can be added to both the top and bottom chambers prior to addition of the cells. The capacity of an agent to inhibit or promote chemotaxis can be determined by comparing the number of cell that migrate to the bottom chamber in wells which contain the agent, to the number of cells which migrate to the bottom chamber in control wells. Control wells can contain equivalent amounts of DMSO, but no agent.

An agent which binds to a mammalian GPR-9-6 can also be assessed by monitoring cellular responses induced by active receptor, using suitable cells which express a mammalian GPR-9-6 or a functional variant thereof. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.*, 155: 3877-3888 (1995), regarding assays for release of granule-derived serine esterases; Loetscher et al., *J. Immunol.*, 156: 322-327 (1996), regarding assays for enzyme and granzyme release; Rot, A. et al., *J. Exp. Med.*, 176: 1489-1495 (1992) regarding respiratory burst; Bischoff, S. C. et al., *Eur. J. Immunol.*, 23: 761-767 (1993) and Baggiolini, M. and C. A. Dahinden, *Immunology Today*, 15: 127-133 (1994)).

In one embodiment, an agent that can inhibit or promote a function of GPR-9-6 is identified by monitoring the release of an enzyme upon degranulation or exocytosis by a cell capable of this function. Cells expressing a mammalian GPR-9-6 or a functional variant thereof can be maintained in a suitable medium under suitable conditions, and degranulation can be induced. The cells are contacted with an agent to be tested, and enzyme release can be assessed. The release of an enzyme into the medium can be detected or measured using a suitable assay, such as an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.*, 155: 3877-3888 (1995) regarding release of granule-derived serine esterases).

In another embodiment, cells expressing a mammalian GPR-9-6 or a functional variant thereof are combined with a ligand of GPR-9-6 (e.g., TECK), an agent to be tested is added before, after or simultaneously therewith, and $Ca^{2+}$ flux is assessed. Inhibition of ligand-induced $Ca^{2+}$ flux is indicative that the agent is an inhibitor or antagonist of mammalian GPR-9-6 function.

Cellular adherence can be monitored by methods known in the art or other suitable methods. Engagement of the chemokine receptors of a lymphocyte can cause integrin activation, and induction of adherence to adhesion molecules expressed in vasculature or the perivascular space. In one embodiment, a ligand, inhibitor and/or promoter of GPR-9-6 function is identified by monitoring cellular adherence by a cell capable of adhesion. For example, an agent to be tested can be combined with (a) cells expressing a mammalian GPR-9-6 or a functional variant thereof (preferably non-adherent cells which when transfected with receptor acquire adhesive ability), (b) a composition comprising a suitable adhesion molecule (e.g., a substrate such as a culture well coated with an adhesion molecule, such as fibronectin), and (c) a ligand or promoter (e.g., agonist), and maintained under conditions suitable for ligand- or promoter-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signaling, and/or cellular responses. In another embodiment, an agent to be tested can be combined with cells expressing a mammalian GPR-9-6 and a composition comprising a suitable adhesion molecule under conditions suitable for ligand- or promoter-induced adhesion, and adhesion is monitored. Increased adhesion relative to a suitable control is indicative of the presence of a ligand and/or promoter.

An agent which binds a mammalian TECK or a functional variant thereof can be further studied in one or more suitable assays to determine if said agent can modulate (inhibit (reduce or prevent) or promote) one or more functions mediated by receptor (e.g., GPR-9-6 (CCR9)) upon TECK binding. Suitable assays for assessing whether a TECK-binding agent can modulate function of the chemokine include assays, such as those described herein where a cell that expresses a TECK receptor (e.g., human GPR-9-6 (human CCR9)) and TECK (e.g. human TECK) are used.

The binding assays and functional assays described above can be used, alone or in combination with each other or other suitable methods, to detect or identify agents which bind a mammalian GPR-9-6 protein (CCR9), agents which bind a mammalian TECK protein and/or modulators (inhibitors, promoters) of a GPR-9-6 protein or TECK protein function. The in vitro methods of the present invention can be adapted for high-throughput screening in which large numbers of samples are processed (e.g., a 96-well format). Cells expressing a mammalian GPR-9-6 (e.g., human GPR-9-6 (CCR9)) or a functional variant thereof at levels suitable for high-throughput screening can be used, and thus, are particularly valuable in the identification and/or isolation of agents which bind GPR-9-6, bind TECK and modulators of GPR-9-6 or TECK function. Expression of GPR-9-6 can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the GPR-9-6 at the desired level can be selected (e.g., by flow cytometry).

Models of Inflammation

In vivo models of inflammation are available which can be used to assess the efficacy of antibodies and antigen-binding fragments of the invention as well as agents identified by the methods described herein as in vivo therapeutics. For example, leukocyte infiltration upon intradermal injection of a chemokine and an antibody or antigen-binding fragment thereof reactive with mammalian GPR-9-6 into a suitable animal, such as rabbit, mouse, rat, guinea pig or primate (e.g., rhesus macaque) can be monitored (see e.g., Van Damme, J. et al., *J. Exp. Med.*, 176: 59-65 (1992); Zachariae, C. O. C. et al., *J. Exp. Med.* 171: 2177-2182 (1990); Jose, P. J. et al., *J. Exp. Med.* 179: 881-887 (1994)). In one embodiment, skin biopsies are assessed histologically for infiltration of leukocytes (e.g., GPR-9-6$^+$ T cells). In another embodiment, labeled cells (e.g., stably transfected cells expressing a mammalian GPR-9-6, labeled with $^{111}$In for example) capable of chemotaxis and extravasation are administered to the animal. For example, an antibody or agent to be assessed which binds a mammalian GPR-9-6 can be administered, either before, simultaneously with or after a GPR-9-6 ligand or agonist (e.g., TECK) is administered to the test animal. A decrease of the extent of infiltration in the presence of antibody or agent as compared with the extent of infiltration in the absence of said antibody or agent is indicative of inhibition.

As described herein, GPR-9-6 is selectively expressed on memory lymphocytes which home to mucosal sites (e.g., CLA$^{-ve}$ $\alpha 4\beta 7^{hi}$ CD4$^+$ lymphocytes). Thus, animal models of inflammatory diseases of the mucosa (e.g., respiratory tract, urogenital tract, alimentary canal and associated organs and tissues (e.g., pancreas, liver, gall bladder)) can be used to assess the therapeutic efficacy of GPR-9-6 modulating agents. For example, the antibodies and antigen binding fragments of the invention as well as agents identified by the methods described herein can be studied in the cotton-top tamarin model of inflammatory bowel disease (Podolsky, D. K., et al., *J. Clin. Invest.* 92:372-380 (1993)). The CD45RB$^{Hi}$/SCID model provides a mouse model with similarity to both Crohn's disease and ulcerative colitis (Powrie, F. et al., *Immunity*, 1: 553-562 (1994)). Therapeutic efficacy in this model can be assessed, for example, by using parameters such as inhibition of recruitment of $^{111}$In-labeled cells to the colon and reduction in the number of CD4$^+$ T lymphocytes in the lamina propria of the large intestine after administration (e.g., intravenous (i.v.), intraperitoneally (i.p.) and per oral (p.o.)) of an agent. Knockout mice which develop intestinal lesions similar to those of human inflammatory bowel disease have also been described (Strober, W. and Ehrhardt, R. O., *Cell*, 75: 203-205 (1993)), and NOD mice provide an animal model of insulin-dependent diabetes mellitus.

As described herein, GPR-9-6 is also expressed on cancer cells. Thus, animal models of cancers can be used to assess the anti-cancer activity of GPR-9-6 modulating agents in vivo. For example, the efficacy of antibodies and antigen-binding fragments of the invention, as well as agents identified by the methods described herein, as therapeutics for the treatment of leukemia (e.g., acute T cell lymphoblastic leukemia) can be assessed in rabbits (Simpson R. M. et al., *Lab. Invest.*, 74:696-710 (1996)) or SCID or NOD mice (Stelle, J. P. et al., *Blood*, 90:2015-2019(1997)).

Diagnostic Applications

The antibodies of the present invention have application in procedures in which GPR-9-6 can be detected on the surface of cells. The receptor provides a marker of the leukocyte cell types in which it is expressed. For example, antibodies raised against a mammalian GPR-9-6 protein or peptide, such as the antibodies described herein (e.g., mAb 3C3, mAb GPR96-1), can be used to detect and/or quantify cells expressing a mammalian GPR-9-6. In one embodiment, the antibodies can be used to sort cells which express GPR-9-6 from among a mixture of cells (e.g., to isolate leukocytes which home to the mucosa, such as GPR-9-6$^+$ CLA$^{-ve}$ α4β7$^{+ve}$ CD4$^+$ memory T cells). Suitable methods for counting and/or sorting cells can be used for this purpose (e.g., flow cytometry, fluorescence activated cell sorting). Cell counts can be used in the diagnosis of diseases or conditions in which an increase or decrease in leukocyte cell types (e.g., leukocytes which home to the mucosa, IEL, LPL) is observed.

Furthermore, the antibodies can be used to detect or measure expression of GPR-9-6. For example, antibodies of the present invention can be used to detect or measure a mammalian GPR-9-6 in a biological sample (e.g., cells, tissues or body fluids from an individual such as blood, serum, leukocytes (e.g., activated T lymphocytes), bronchoalveolar lavage fluid, saliva, bowel fluid, biopsy specimens). For example, a sample (e.g., tissue and/or fluid) can be obtained from an individual and a suitable assay can be used to assess the presence or amount of GPR-9-6 protein. Suitable assays include immunological and immunochemical methods such as flow cytometry (e.g., FACS analysis) and enzyme-linked immunosorbent assays (ELISA), including chemiluminescence assays, radioimmunoassay, immuno-blot (e.g., western blot) and immunohistology. Generally, a sample and antibody of the present invention are combined under conditions suitable for the formation of an antibody-GPR-9-6 complex, and the formation of antibody-receptor complex is assessed (directly or indirectly).

The presence of an increased level of GPR-9-6 reactivity in a sample (e.g., a tissue sample) obtained from an individual can be indicative of inflammation and/or leukocyte (e.g., activated T cell) infiltration and/or accumulation associated with an inflammatory disease or condition, such as an inflammatory bowel disease, allograft rejection, delayed type hypersensitivity reaction, or an infection such as a viral or bacterial infection. The presence of a decreased level of GPR-9-6 reactivity in the circulation (e.g., on the surface of circulating lymphocytes) can also be indicative of leukocyte infiltration and/or accumulation at inflammatory sites. The level of expression of a mammalian GPR-9-6 protein or variant can also be used to correlate increased or decreased expression of a mammalian GPR-9-6 protein with a particular disease or condition, and in the diagnosis of a disease or condition in which increased or decreased expression of a mammalian GPR-9-6 protein occurs (e.g., increased or decreased relative to a suitable control, such as the level of expression in a normal individual). Similarly, the course of therapy can be monitored by assessing GPR-9-6 immunore-activity in a sample from a subject. For example, antibodies of the present invention can be used to monitor the number of cells expressing GPR-9-6 in a sample (e.g., blood, tissue) from a subject being treated with an anti-inflammatory or immunosuppressive agent.

Antibodies which bind TECK can be used to detect or measure expression of TECK. For example, antibodies of the present invention can be used to detect or measure a mammalian TECK in a biological sample (e.g., cells, or body fluids from an individual such as blood, serum, leukocytes (e.g., activated T lymphocytes), bronchoalveolar lavage fluid, saliva, bowel fluid). For example, a sample (e.g., serum) can be obtained from an individual and a suitable assay can be used to assess the presence or amount of TECK protein. Suitable assays include immunological and immunochemical methods such as flow cytometry (e.g., FACS analysis, including intracellular staining) and enzyme-linked immunosorbent assays (ELISA), including chemiluminescence assays, radioimmunoassay, immuno-blot (e.g., western blot) and immunohistology. (See, for example, Kallas, E. G., et al., *J. Infect. Dis.*, 179:1124-1131 (1999), regarding intracellular staining of cells to detect secreted proteins.) Generally, a sample and antibody of the present invention are combined under conditions suitable for the formation of an antibody-TECK complex, and the formation of antibody-TECK complex is assessed (directly or indirectly).

The presence of an increased level of TECK reactivity in a sample (e.g., a fluid sample) obtained from an individual can be indicative of inflammation and/or leukocyte (e.g., activated T cell) infiltration and/or accumulation associated with an inflammatory disease or condition, such as an inflammatory bowel disease, allograft rejection, delayed type hypersensitivity reaction, or an infection such as a viral or bacterial infection. The level of expression of a mammalian TECK protein or variant can also be used to correlate increased or decreased expression of a mammalian TECK protein with a particular disease or condition, and in the diagnosis of a disease or condition in which increased or decreased expression of a mammalian TECK protein occurs (e.g., increased or decreased relative to a suitable control, such as the level of expression in a normal individual). Similarly, the course of therapy can be monitored by assessing TECK immunoreactivity in a sample from a subject. For example, antibodies of the present invention can be used to monitor the amount of TECK in a sample (e.g., blood) from a subject being treated with an anti-inflammatory or immunosuppressive agent.

Kits for use in detecting the presence of a mammalian GPR-9-6 protein or mammalian TECK protein in a biological sample can also be prepared. Such kits can include an antibody or functional fragment thereof which binds to the target protein (i.e., a mammalian GPR-9-6 receptor or portion of said receptor, a mammalian TECK protein or portion thereof) as well as one or more ancillary reagents suitable for detecting the presence of a complex between the antibody or fragment and target. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody capable of binding to the target protein (e.g., a second anti-GPR-9-6 antibody or anti-TECK antibody) is employed, such antibody can be provided in the kit, for instance in a separate vial or container. The second antibody, if present, is typically labeled, and can be formulated in an analogous manner with the antibody formulations described above. The components (e.g., anti-GPR-9-6 antibody or antigen-binding fragment thereof, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Similarly, the present invention also relates to a method of detecting and/or quantifying expression of a mammalian GPR-9-6 receptor or a portion of the receptor by a cell, in which a composition comprising a cell or fraction thereof (e.g., membrane fraction) is contacted with an antibody or functional fragment thereof (e.g., mAb 3C3, mAb GPR96-1) which binds to a mammalian GPR-9-6 (CCR9) or portion of the receptor under conditions appropriate for binding of the antibody or fragment thereto, and binding is monitored. Detection of the antibody, indicative of the formation of a complex between antibody and a mammalian GPR-9-6 (CCR9) or a portion thereof, indicates the presence of the receptor. Binding of antibody to the cell can be determined using any suitable method. The method can be used to detect expression of GPR-9-6 on cells from a subject (e.g., in a sample, such as a body fluid, such as blood, saliva or other suitable sample). The level of expression of GPR-9-6 on the surface of cells (e.g., leukocytes) can also be determined, for instance, by flow cytometry, and the level of expression (e.g., staining intensity) can be correlated with disease susceptibility, progression or risk.

Methods of Therapy

Modulation of mammalian GPR-9-6 function according to the present invention, through the inhibition or promotion of at least one function characteristic of a mammalian GPR-9-6 protein, provides an effective and selective way of inhibiting or promoting receptor-mediated functions. Once lymphocytes are recruited to a site, other leukocyte types, such as monocytes, may be recruited by secondary signals. Thus, agents which can modulate GPR-9-6 function, including ligands, inhibitors and/or promoters, such as those identified as described herein, can be used to modulate leukocyte function (e.g., leukocyte infiltration including recruitment and/or accumulation).

In one aspect, the present invention provides a method of modulating (inhibiting or promoting) an inflammatory response in a subject, comprising administering an effective amount of an agent which inhibits or promotes mammalian GPR-9-6 function to a subject in need of such therapy. In one embodiment, an effective amount of an agent which inhibits one or more functions of a mammalian GPR-9-6 protein (e.g., a human GPR-9-6) is administered to a subject to inhibit (i.e., reduce or prevent) inflammation. Preferred agents for modulating an inflammatory response in a subject are agents which inhibit (i.e., reduce or prevent) binding of ligand (e.g. TECK) to GPR-9-6 (CCR9). For example, antibodies of the present invention, including mAb 3C3, mAb GPR96-1, mAb 11.3.1 and mAb 16.3.1 can be used in the method. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a inflamed mucus membrane (e.g., colon, small intestine)) can be inhibited according to the present method. In another embodiment, an effective amount of an agent which inhibits one or more functions of a mammalian GPR-9-6 protein (e.g., a human GPR-9-6) is administered to a subject to inhibit (i.e., reduce or prevent) GPR-9-6-mediated homing of leukocytes. In particular embodiments, an effective amount of an agent which binds to human GPR-9-6 (human CCR9) and/or an effective amount of an agent which binds to human TECK is administered to a subject in need thereof.

Thus, the invention relates to a method of treating a subject having an inflammatory disease, comprising administering an effective amount of an antagonist of GPR-9-6 function. In a particular embodiment, the subject has an inflammatory bowel disease, such as Crohn's disease or colitis. Treatment includes therapeutic or prophylactic treatment. Treatment, in accordance with the method, can prevent disease or reduce the severity of disease in whole or in part.

The invention also relates to a method of inhibiting GPR-9-6-mediated homing of leukocytes in a subject, comprising administering an effective amount of an antagonist of GPR-9-6 function, for example, the homing of leukocytes to mucosal sites can be inhibited. Immigration of circulating leukocytes into organs or tissue (e.g., intestine) and/or local recruitment of lymphocytes within an organ or tissue (e.g., IEL, LPL) can be inhibited in accordance with the method.

An agent (e.g., receptor agonist) which promotes one or more functions of a mammalian GPR-9-6 protein (e.g., a human GPR-9-6) can be administered to induce (trigger or enhance) the recruitment of cells to a desired site or to induce an inflammatory response, such as leukocyte emigration, chemotaxis, exocytosis (e.g., of enzymes) or inflammatory mediator release, resulting in the beneficial stimulation of inflammatory processes. For example, T cells can be recruited to combat viral, bacterial or fungal infections. Thus, the invention relates to a method of promoting GPR-9-6 mediated homing of leukocytes in a subject, comprising administering an effective amount of a promoter (e.g., agonist) of GPR-9-6 function.

In another aspect the invention is a method of treating a subject having cancer (e.g., acute or chronic leukemia (e.g., acute T-cell lymphoblastic leukemia, acute B-cell lymphoblastic leukemia, chronic T-cell lymphoblastic leukemia, chronic B-cell lymphoblastic leukemia), lymphoma (e.g., Hodgkin's disease, T cell lymphoma), carcinoma (e.g., breast (e.g., ductal carcinoma, lobular carcinoma), ovarian, testicular, prostatic, squamous cell, basal cell), melanoma, myeloma, adenoma). Treatment includes therapeutic or prophylactic treatment. Treatment, in accordance with the method, can prevent disease or reduce the severity of disease in whole or in part. For example, the method can be employed to inhibit tumor formation, tumor growth and/or metastasis (e.g., leukemic cell infiltration of bowel or thymus).

In one embodiment, the method of treating a subject having cancer comprises administering an effective amount of an (i.e., one or more) antagonist of GPR-9-6 function to a subject in need thereof. In another embodiment, the method of treating a subject having cancer comprises administering an effective amount of an antibody which binds GPR-9-6 to a subject in need thereof. The antibody which binds GPR-9-6 can be a GPR-9-6 antagonist (e.g., inhibit binding of ligand (e.g., TECK) to GPR-9-6 and thereby inhibit GPR-9-6 mediated signal transduction) and/or can induce cell death, directly or indirectly. For example, an IgG or IgM which binds GPR-9-6 can be administered to a subject having acute T cell lymphoblastic leukemia. Upon binding to GPR-9-6 expressed by a leukemia cell, the IgG or IgM can activate complement and induce lysis of the cell. Antibodies which are directly or indirectly linked to cytotoxic agents (antigen-binding fusion proteins, immunoconjugates) can also be administered to selectively deplete cells expressing GPR-9-6.

In a preferred embodiment, the invention is a method of treating a subject having leukemia (e.g., acute lymphoblastic leukemia (e.g., acute T-cell lymphoblastic leukemia, acute B-cell lymphoblastic leukemia), chronic lymphoblastic leukemia e.g., chronic T-cell lymphoblastic leukemia, chronic B-cell lymphoblastic leukemia)) comprising administering an effective amount of an (i.e., one or more) antagonist of GPR-9-6 function and/or an antibody which binds GPR-9-6 to a subject in need thereof.

The term "subject" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with inflammation and/or infection can be treated using the methods described herein. In a preferred embodiment, the disease or condition is one in which the actions of lymphocytes, particularly lymphocytes which home to mucosal tissues, are to be inhibited or promoted for therapeutic (including prophylactic) purposes. In a particularly preferred embodiment, the inflammatory disease or condition is a T cell-mediated disease or condition.

Examples of inflammatory diseases associated with mucosal tissues which can be treated according to the present method include mastitis (mammary gland), vaginitis, cholecystitis, cholangitis or pericholangitis (bile duct and surrounding tissue of the liver), chronic bronchitis, chronic sinusitis, asthma, and graft versus host disease (e.g., in the gastrointestinal tract). As seen in Crohn's disease, inflammation often extends beyond the mucosal surface, accordingly chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases, sarcoidosis, and other idiopathic conditions can be amenable to treatment. Pancreatitis and insulin-dependent diabetes mellitus are other diseases which can be treated using the present method.

In a particularly preferred embodiment, diseases which can be treated accordingly include inflammatory bowel disease (IBD), such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis.

Additional diseases or conditions, including chronic diseases, of humans or other species which can be treated with inhibitors of GPR-9-6 function, include, but are not limited to:

inflammatory or allergic diseases and conditions, including systemic anaphylaxis or hypersensitivity responses, drug allergies (e.g., to penicillin, cephalosporins), insect sting allergies; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis;

autoimmune diseases, such as arthritis (e.g., rheumatoid arthritis, psoriatic arthritis), multiple sclerosis, systemic lupus erythematosus, myasthenia gravis, juvenile onset diabetes, glomerulonephritis and other nephritides, autoimmune thyroiditis, Behcet's disease;

graft rejection (e.g., in transplantation), including allograft rejection or graft-versus-host disease;

other diseases or conditions in which undesirable inflammatory responses are to be inhibited can be treated, including, but not limited to, atherosclerosis, restenosis, myositis (including polymyositis, dermatomyositis);

cancers, particularly those with leukocytic infiltration of the skin or organs such as cutaneous T cell lymphoma (e.g., mycosis fungoides);

Diseases or conditions of humans or other species which can be treated with promoters (e.g., an agonist) of GPR-9-6 function, include, but are not limited to:

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes.

Modes of Administration

According to the method, one or more agents can be administered to the subject by an appropriate route, either alone or in combination with another drug. An effective amount of an agent (e.g., a molecule which inhibits ligand binding, an anti-GPR-9-6 antibody or antigen-binding fragment thereof, an anti-TECK antibody or antigen-binding fragment thereof) is administered. An effective amount is an amount sufficient to achieve the desired therapeutic or prophylactic effect, under the conditions of administration, such as an amount sufficient for inhibition or promotion of GPR-9-6 receptor function, and thereby, inhibition or promotion, respectively, of a GPR-9-6-mediated process (e.g., an inflammatory response). The agents can be administered in a single dose or multiple doses. The dosage can be determined by methods known in the art and is dependent, for example, upon the particular agent chosen, the subject's age, sensitivity and tolerance to drugs, and overall well-being. Suitable dosages for antibodies can be from about 0.01 mg/kg to about 100 mg/kg body weight per treatment.

A variety of routes of administration can be used including, for example, oral, dietary, topical, transdermal, rectal, parenteral (e.g., intravenous, intraarterial, intramuscular, subcutaneous, intrathecal, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (e.g., GPR-9-6 antagonist, anti-TECK antibody) chosen, and the particular condition (e.g., disease) being treated, however, oral or parenteral administration is generally preferred.

The agent can be administered as a neutral compound or as a salt. Salts of compounds containing an amine or other basic group can be obtained, for example, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent (e.g., agent which inhibits the binding of TECK to GPR-9-6 (CCR9)) can be administered to the individual as part of a pharmaceutical or physiological composition. For example, the agent can be administered as part of a pharmaceutical composition for modulation of GPR-9-6 function comprising an inhibitor or promotor of GPR-9-6 function and a pharmaceutically acceptable carrier. Formulation will vary according to the route of administration selected (e.g., solution, emulsion, capsule). Suitable pharmaceutical or physiological carriers can contain inert ingredients which do not interact with the promoter (agonist) or inhibitor (antagonist) of GPR-9-6 function. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The present invention will now be illustrated by the following Examples, which are not intended to be limiting in any way.

EXEMPLIFICATION

Example 1

Purification of Cell Populations

Human peripheral blood was collected in 10% (v/v) 0.1 M EDTA, layered onto 1-Step Polymorphs gradient (1.113±0.01 g/ml, Accurate Chemical Co., Westbury, N.Y.) and centrifuged at 400×g for 30 minutes at room temperature. Neutrophil and mononuclear cell layers were collected, re-suspended in Dulbecco's phosphate buffered saline (DPBS) without calcium and magnesium (Life Technologies, Grand Island, N.Y.) and centrifuged for 15 minutes at ~750×g. Red blood cells were lysed in the neutrophil fraction by re-suspending the pellet in E-Lyse (5 ml/$10^7$ cells)(Cardinal Associates, Santa Fe, N. Mex.) for 5 minutes on ice. Both cell fractions were washed 2 times with ice cold DPBS. The mononuclear cells were allowed to adhere to protein coated plastic for 2-3 hours and then non-adherent cells were gently washed off the plate. After a further 12 hours the non-adherent dendritic cells were washed off the plate and depleted of B lymphocytes and T lymphocytes with anti-CD19 and anti-CD2 coated magnetic beads (Dynabeads; Dynal, Oslo, Norway) (5 beads per cell). The remaining cells were cultured in 50 ng/ml granulocyte macrophage colony stimulating factor (GMCSF, R and D Systems, Minneapolis, Minn.) and 40 ng/ml IL-4® and D Systems) Dulbecco's modified Eagle's medium (DMEM, Gibco BRL, Grand Island, N.Y.) 10% fetal calf serum (FCS, HyClone, Logan, Utah) plus additives: penicillin 50U/ml, streptomycin 50 μg/ml, L-glutamine 2 mM, HEPES 10 mM, MEM sodium pyruvate 10 mM, MEM nonessential amino acids 0.1 mM and 2-mercaptoethanol $5.5 \times 10^{-5}$M (all from Gibco BRL, Grand Island, N.Y.) for 7 days (Sallusto, F. and Lanzabecchia, A., *J. Exp. Med.*, 179:1109-1118 (1994)) to generate immature dendritic cells (IMDC) and in some cases 24 hours further culture in 10 ng/ml LPS was used to mature the dendritic cells. $CD4^+$, $CD8^+$, $CD14^+$, $CD56^+$ and $CD19^+$ populations were purified from mononuclear cells with the relevant Miltenyi Beads (Millenyi Biotek, Bergisch Gladbach, Germany) using 20 μl of beads for $10^7$ mononuclear cells in PBS/1% BSA/5 mM EDTA at $5 \times 10^7$ cells/ml for 30 minutes at 4° C. They were then spun down, re-suspended in PBS/1% BSA/5 mM EDTA and $5 \times 10^7$ cells/ml and passed over a VS column (Miltenyi Biotech, Auburn, Calif. 95603) in a magnetic field to remove non-tagged cells. Cells were removed by forcing 20 ml of PBS/1% BSA/5 mM EDTA over the VS column, outside the magnetic field.

Antibodies and Reagents

Labeled antibodies which bind to: CD4, CD8, CD14, CD19, CD49d, CD56, CD62L, CLA, CD45RA, CD45RO, CXCR5, CD80 and CD86 were obtained from Pharmingen (San Diego, Calif.) and used for immunofluorescence studies, while anti-αE and Anti-CD83 were obtained from Beckman Coulter (Fullerton, Calif.). OKT3, a anti-human CD3 mAb, was obtained from American Type Culture Collection (ATCC, Manassas, Va.) and anti-human CD28 mAb was obtained from Becton Dickinson (Mountain View, Calif.). Some of the anti-chemokine receptor mAbs were produced at LeukoSite, Inc. (Cambridge, Mass.) and have the clone names anti-CCR3 (7B11), anti-CCR4 (2B10), anti-CCR6 (11A9) and anti-CXCR3 (1C6). Several anti-chemokine receptor mAbs used in FACS analysis were obtained from commercial sources. Anti-CCR2, anti-CCR6 and anti-CXCR5 mAbs used for immunofluorescence studies were obtained from R and D Systems (Minneapolis, Minn.), while anti-CCR5 and anti-CXCR4 were obtained from Pharmingen (San Diego, Calif.). Recombinant human chemokines were obtained from Peprotech (Rocky Hill, N.J.) and R&D Systems (Minneapolis, Minn.) and in some cases synthesized using solid phase methods that were optimized and adapted to a fully automated peptide synthesizer (model 430A; Applied Biosystems, Foster City, Calif.) as described (Clark-Lewis, I., et al., *Biochemistry*, 30:3128-3135 (1991)). The human endothelial cell line ECV304 was purchased from ATCC. All cytokines were obtained from R&D Systems (Minneapolis, Minn.).

Generation of Anti-GPR-9-6 mAbs

A peptide consisting of the $NH_2$ terminus of GPR-9-6 was generated having the sequence MADDYGSESTSSM-EDYVNFNFTDFYC (SEQ ID NO:3). BALB/C mice were immunized i.p. with 10 µg of GPR-9-6 peptide/KLH conjugate prepared in Freunds Complete Adjuvant (FCA, Sigma, St. Louis, Mo.) at day 1, 10 µg of GPR-9-6 peptide/KLH conjugate prepared in Incomplete Freunds Adjutant (IFA, Sigma, St. Louis, Mo.) at day 20, and 10 µg of GPR-9-6 peptide/KLH conjugate prepared in PBS at day 40. At day 60, the mice were boosted with 10 µg of GPR-9-6 peptide/KLH in PBS, and after 4 days, the spleens were removed and fused to SP2/0 myeloma cells (ATCC) (Coligan et al, *Current Protocols in Immunology* 2.5.1 (1992)). Fusions were screened by ELISA, using plates coated with GPR-9-6 peptide. Hybridomas producing anti-GPR-9-6 mAbs were checked for reactivity with GPR-9-6 transfectants and subcloned for further characterization. Murine hybridoma 3C3, also referred to as hybridoma LS129-3C3-E3-1, can be cultivated at 37° C. in an 5% CO2 atmosphere in DMEM supplemented with FCS (10%), IL-6 (100 ng/ml), penicillin (50 U/ml), streptomycin (50 µg/ml), L-glutamine (2 mM), HEPES (10 mM), MEM sodium pyruvate (10 mM), MEM nonessential amino acids (0.1 mM) and 2-mercaptoethanol ($5.5 \times 10^{-5}$M).

Preparation of Chronically Activated $T_H1$ and $T_H2$ Lymphocytes

As previously described (Murphy, E., et al., *J. Exp. Med.* 183:901-913 (1997)), six-well Falcon plates were coated overnight with 10 µg/ml anti-CD28 and 2 µg/ml OKT3, and then washed twice with PBS. Umbilical cord blood CD4+ lymphocytes (Poietic Systems, German Town, Md.) were cultured at $10^5$-$10^6$ cells/ml in DMEM with 10% FCS and IL-2 (4 ng/ml). IL-12 (5 ng/ml) and anti-IL-4 (1 µg/ml) were used to direct to $T_H1$, while IL-4 (5 ng/ml) and anti-IFN gamma (1 µg/ml) were used to direct to $T_H2$. After 4-5 days, the activated $T_H1$ and $T_H2$ lymphocytes were washed once in DMEM and cultured for 4-7 days in DMEM with 10% FCS and IL-2 (1 ng/ml). Following this, the activated $T_H1$ and $T_H2$ lymphocytes were re-stimulated for 5 days with anti-CD28/OKT3 and cytokines as described above, but with the addition of anti-CD95L (1 µg/ml) to prevent apoptosis. After 4-5 days the $T_H1$ and $T_H2$ lymphocytes were washed and then cultured again with IL-2 for 4 days. Activated $T_H1$ and $T_H2$ lymphocytes were maintained in this way for a maximum of three cycles.

ECV304 Transmigration and Chemotaxis Assays 3 micrometer pore diameter Transwell tissue culture inserts were either used uncoated or coated with 2% gelatin for 2 hours. Then 0.45 ml of DMEM with 5% FCS was placed in the lower wells of the chambers and $2 \times 10^5$ EVC304 cells were added to each gelatin coated insert in 0.2 ml of DMEM 5% FCS. After two days, the wells and inserts were washed twice with RPMI-1640 (Gibco BRL, Grand Island, N.Y.) containing 0.5% HSA (human serum albumin), 10 mM HEPES and then chemokine was added to the lower well. The cells under study were washed once in RPMI and re-suspended at $4 \times 10^6$ cells/ml for $T_H1/T_H2$ lymphocytes, cell lines and transfectants, or at $10^7$ cells/ml for resting CD4 lymphocytes in RPMI 0.5% HSA and 10 mM HEPES. An aliquot of 200 µl of cell suspension (input of $8 \times 10^5$ cells and $2 \times 10^6$ cells, respectively) was added to each insert. After 2 to 4 hours the inserts were removed and the number of cells which had migrated through the ECV304 monolayer to the lower well counted for 30 seconds on a Becton Dickinson FACScan with the gates set to acquire the cells of interest. Using this technique, 100% migration would be 25,000 cells for $T_H1/T_H2$ cells and 75,000 cells for resting CD4 lymphocytes, where this number represents the cells in the lower well counted on the FACScan over 1 minute. To study the phenotype of migrating cells, identical experiments with CD4 lymphocytes were performed with 6 well plates using 24 mm diameter inserts. Chemotaxis assays were identical to ECV304 migration assays but Fibronectin coated inserts (10 µg/ml) were used. In all cases, the data points were the result of duplicate wells, with the mean value shown and the error bars representing the sample standard deviation.

$Ca^{2+}$ Mobilization ($Ca^{2+}$ Flux) Assay $10^7$ cells/ml in DPBS were labeled for 30 minutes with Fura 2 dye (Molecular Probes, Eugene, Oreg.) at 2 mM, washed three times in DPBS and resuspended at $10^6$ cells/ml in DPBS containing 1 mM $CaCl_2$, 0.5 mM $MgCl_2$, 10 mM HEPES, and 5.5 mM glucose. The cells were then analyzed on a fluorimeter (Hitachi model F2000 fluorescence spectrophotometer, excitation 340 nm, emission 510 nm) using 10% NP-40 and 10 mM EDTA to establish the max and min $Ca^{2+}$ mobilizations.

Recombinant DNA Methods

Plasmid DNA was isolated using QIAGEN®-tips as recommended by manufacturer (QIAGEN® Inc., Chatsworth, Calif.). DNA ligations, restriction endonuclease digestions, and gel electrophoresis were performed as described previously (Sambrook, J., et al., *Molecular Cloning: A Laboratory Manual* 2nd ed., Cold Spring Harbor Laboratory Press, (Cold Spring Harbor, N.Y.) (1989)). DNA purification through agarose gel extraction was performed using the QIAEXII Gel Extraction Kit as recommended by the manufacturer (QIAGEN® Inc., Chatsworth, Calif.). Plasmid DNA was introduced into *E. coli* by chemical transformation (GIBCO, Inc.). Enzymes were purchased from New England Biolabs, Inc. (Beverly, Mass.), GIBCO Bethesda Research Laboratories, Inc. (Gaithersburg, Md.), or from Boehringer Mannheim, Inc. (Germany). RNA was isolated from frozen tissues or cells using either the standard guanidinium isothiocyanate method (Sambrook, J., et al., *Molecular Cloning: A Laboratory Manual* 2nd ed., Cold Spring Harbor Laboratory Press, (Cold Spring Harbor, N.Y.) (1989)) or the RNEASY® kit as recommended (QIAGEN® Inc., Chatsworth, Calif.). DNA sequencing was performed by Sequi-Net (Colorado State University) using the FS DYEDEOXY Terminator cycle sequencing kit and a model 377 DNA sequencer (Perkin Elmer Applied Biosystems, Foster City, Calif.). Sequences were analyzed using SEO-MAN (DNASTAR®, Inc., Madison, Wis.).

PCR

Primers were designed for use in the PCR to amplify the complete coding region of GPR-9-6 based on the nucleotide sequence deposited in GenBank (U45982)(SEQ ID NO:1) which is incorporated herein by reference. BamHI and XbaI sites were incorporated into primer pair BAZ201 5' . . . TCGAAGGGATCCCTAACATGGCTGAT-GACTATGGC . . . 3' (SEQ ID NO:4) and BAZ202 5' . . . AAGAAGTCTAGAACCCCTCAGAGGGAGAGTG-CTCC . . . 3' (SEQ ID NO:5) for directional cloning (bold: coding sequence, italic: enzyme site). 5 µg of total human genomic DNA (Clontech, Palo Alto, Calif.) was used as the template in the Pfu PCR cycles, with 60 mM Tris-HCL, pH 9.5, 1.5 mM $MgCl_2$, 100 pmol primers, 200 µM dNTP, and 5 units PfuI polymerase (Invitrogen, Carlsbad, Calif.) in a 100 μl volume. The cycle parameters were an initial melt 95° C., 2 minutes, then 35 cycles: 95° C., 30s; 55° C., 30s; 72° C., 2 minutes 15 s, followed by a final extension 72° C., 7 minutes in a DNA thermal cycler (Perkin-Elmer Corp., Norwalk, Conn.).

Primers were designed to amplify the complete coding region of TECK based on the published nucleotide sequence (accession U86358), which is incorporated herein by reference. HindIII and XbaI sites were incorporated into primer pair BAZ203 5' . . . TCGAAGAAGCTTATGAACCTGTGGCTCCTG . . . 3' (SEQ ID NO:6) and BAZ204 5' . . . AAGAAGTCTAGATCACAGTCCTGAATTAGC . . . 3' (SEQ ID NO:7) for directional cloning (bold: coding sequence, italic: enzyme site). 5 μg of human thymus RNA was reverse transcribed with oligo dT in a 20 μl volume. The cDNA was mixed with 200 μM dNTP, 100 pmol primers, 60 mM Tris-HCl, pH 9.5, 1.5 mM MgCl$_2$, and 10 units AmpliTaq polymerase (Perkin-Elmer Roche Molecular Systems, Branchburg, N.J.) in a 50 μl volume. The cycle parameters were an initial melt 95° C., 2 minutes, then 35 cycles: 95° C., 30 s; 55° C., 30 s; 72° C., 1 minute, followed by a final extension 72° C., 7 minutes The human thymus was obtained from Children's Hospital (Boston, Mass.).

Semi-quantitative PCR amplification of TECK using primers BAZ203 (SEQ ID NO:6) and BAZ204 (SEQ ID NO:7), and of GPR-9-6 using primers BAZ201 (SEQ ID NO:4) and BAZ202 (SEQ ID NO:5), was performed using equal amounts of cDNA (500 ng) template from thymus, small intestine, colon, brain, lymph node, and spleen, as well as 500 ng genomic DNA (ClonTech, Palo Alto, Calif.). The same conditions and PCR profile were used as the AmpliTaq PCR cycle described above, except that 30 cycles were performed. Amplification with glyceraldehyde-3-phosphate dehydrogenase (G3PDH) primers (ClonTech, Palo Alto, Calif., catalog number 5840-1) was used to demonstrate equivalency of template.

After agarose gel electrophoresis, the PCR products were visualized in the presence of ethidium bromide with a UV light source. DNA fragments of predicted size (~450 bp for TECK and ~1 kb for GPR-9-6) were isolated and cloned into pBluescript II KS+ (Stratagene, Inc., La Jolla, Calif.) and pcDNA3 (Stratagene, Inc.), respectively, for sequence analysis and further manipulation.

Expression Vector Construction and Generation of a GPR-9-6-expressing Stable Cell Line The coding region of GPR-9-6 was amplified by PCR and directionally cloned into the BamHI/XbaI sites of pcDNA3 (Invitrogen, San Diego, Calif.). Transfectants were then generated in the murine pre-B lymphoma cell line L1.2, maintained in RPMI-1640 supplemented with 10% fetal calf serum (HyClone, Logan, Utah), 2 mM L-glutamine, 50 units/ml Pen/Strep, 0.55 mM β-mercaptoethanol, 10 mM HEPES, and 1 mM sodium pyruvate (Gibco BRL). 20 μg of linearized GPR-9-6 in pcDNA3 was used to transfect the cell line as follows. L1.2 cells were washed twice in PBS and re-suspended in 0.8 ml of the same. The plasmid DNA was mixed with the cells and incubated for 10 minutes at room temperature, transferred to a 0.4-cm electroporation cuvette, and a single pulse was then applied at 250 V, 960 μF. The electroporation was followed by a 10-min incubation at room temperature. G418 (Geneticin, Gibco BRL) was added to a final concentration of 0.8 mg/ml 48 hours after transfection and the cells were grown in bulk culture under drug selection 2-3 weeks. The transfectants were then stained by mAbs with reactivity against the GPR-9-6 peptide (see below) and analyzed by FACScan (Becton Dickinson & Co., Mountain View, Calif.) to confirm surface expression of GPR-9-6 and cloned by limiting dilution. Transfected cells were treated with 5 mM n-butyric acid for 24 hours before experimentation (Palmero, D. P., et al., *J. Biotech.*, 19:35-47 (1991)).

Northern Blot Analysis

Northern blots were either purchased from ClonTech or prepared as follows. Total RNA was separated by electrophoresis on 1.2% formaldehyde agarose gels and transferred to a nylon membranes (Hybond-N+; Amersham Corp., Arlington Heights, Ill.) by the capillary method as described previously (Sambrook, J., et al., *Molecular Cloning: A Laboratory Manual* 2nd ed., Cold Spring Harbor Laboratory Press, (Cold Spring Harbor, N.Y.) (1989)) and crosslinked using a Stratalinker (Stratagene, Inc.). Hybridizations with radio-labeled probes was with ExpressHyb Solution (Clonetech) using the manufacture's suggested protocol. Length of autoradiography exposure is described in appropriate figure legends. Full length gel purified TECK and GPR-9-6 DNA fragments were used in hybridizations.

Results

A mAb Raised to GPR-9-6, mAb 3C3, Selectively Reacts with GPR-9-6 Transfectants

Figure 1:
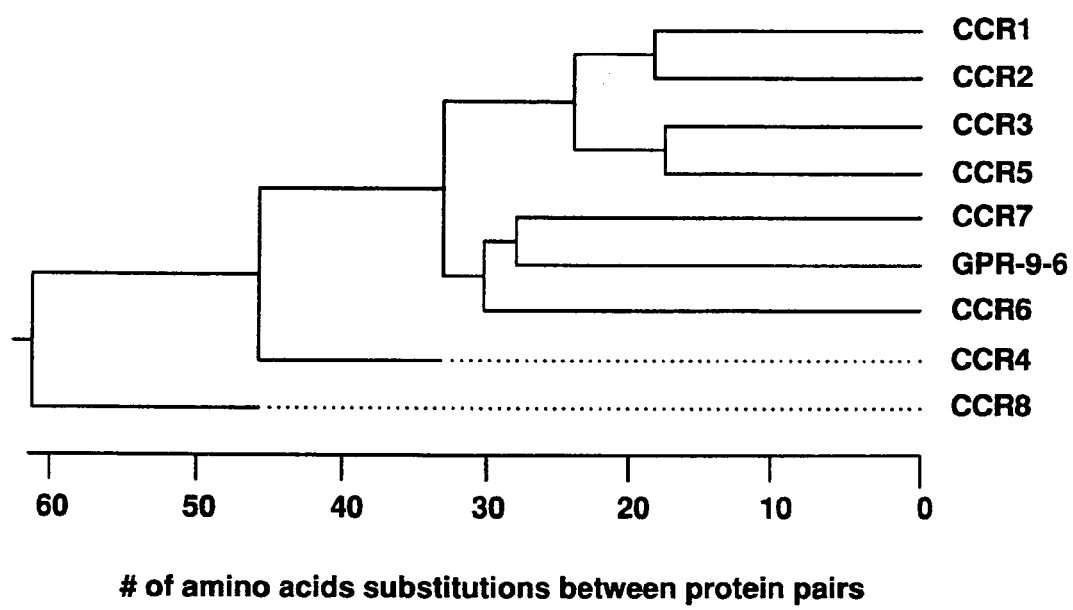
FIG. 1 is a dendrogram illustrating the relationship of GPR-9-6 to other leukocyte chemokine receptors. Using a clustal alignment analysis program (DNASTAR®), the protein sequences of leukocyte chemokine receptors were aligned and used to determine the phylogenetic distances between GPR-9-6 and several chemokine receptors.
Figure 2A:
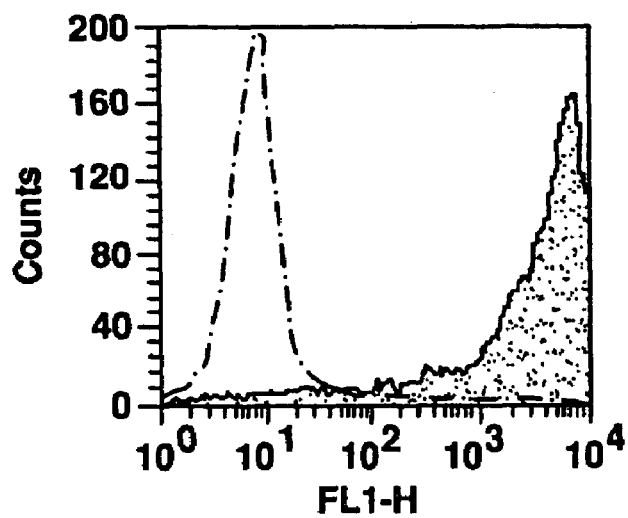
FIGS. 2A-2B illustrate the specific binding of mAb 3C3 to GPR-9-6 transfectants.
Figure 2B:
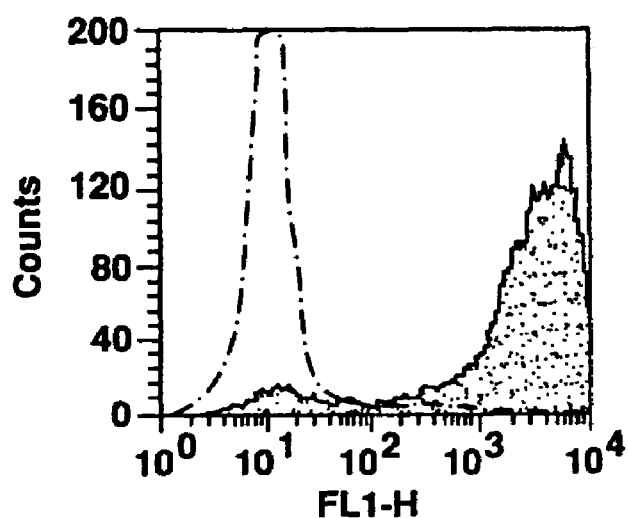

Due to its close phylogenetic association with other known leukocyte chemokine receptors (FIG. 1), we cloned GPR-9-6 by PCR using primers designed from the deposited GenBank sequence. GPR-9-6/L1.2 transfectants were prepared and stained with mAbs raised against GPR-9-6 in fusions in which mice had been immunized with the first 26 amino acids of the NH$_2$ terminus of GPR-9-6 (SEQ ID NO:3) coupled to KLH. The mAb, designated mAb 3C3, reacted with GPR-9-6/L1.2 transfectants but not with parental L1.2 cells. mAb 3C3 was found to have an IgG$_{2b}$ isotype. In cross-reactivity studies, mAb 3C3 did not cross-react with CCR1, CCR2, CCR3, CCR4, CCR5, CCR6, CCR7 or CXCR1, CXCR2, CXCR3 and CXCR4 transfectants. The data for CCR6 are shown herein, as it is one of the more closely related chemokine receptors to GPR-9-6 (FIGS. 2A-2B). Also, the NH$_2$ terminal peptide of GPR-9-6 (SEQ ID NO:3) was found to completely block the binding of mAb 3C3 to GPR-9-6 transfectants (data not shown), further validating the specificity of this mAb.

Figure 3C:
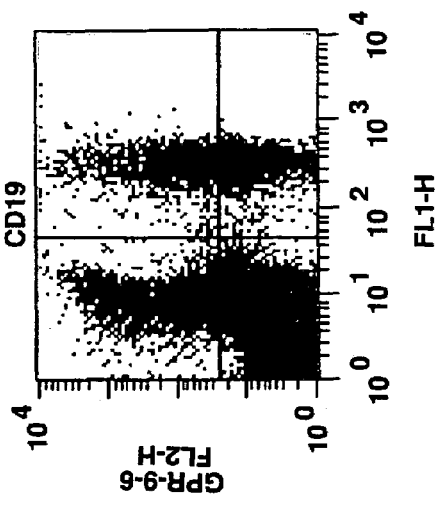
FIGS. 3A-3I are a series of fluorescence plots which illustrate that GPR-9-6 is expressed on B lymphocytes and subsets of CD4 and CD8 lymphocytes. mAb 3C3 was used in two color studies on mononuclear cells along with anti-CD4 FITC (FIG. 3A), anti-CD8 FITC (FIG. 3B), anti-CD19 FITC (FIG. 3C), anti-CD56 Cychrome (FIG. 3D) and anti-CCR3 FITC (FIG. 3E). For thymocytes (FIG. 3F), two color studies were performed with mAb 3C3 and anti-TcR Cychrome. GPR-9-6 expression on monocytes (FIG. 3G), eosinophils (FIG. 3H) and neutrophils (FIG. 3I) was evaluated in one color studies using isolated populations of these cells and mAb 3C3 (—) and IgG2b control ( - - - ). Anti-CCR2, anti-CCR3 and anti-CXCR2 antibodies were used as positive controls for monocytes, eosinophils and neutrophils, respectively (stippled profiles) (n=3).
Figure 3B:
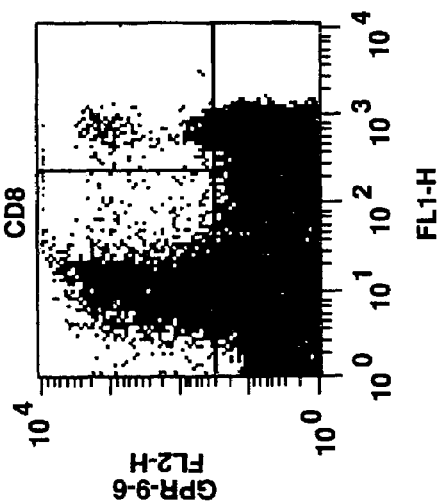
Figure 3A:
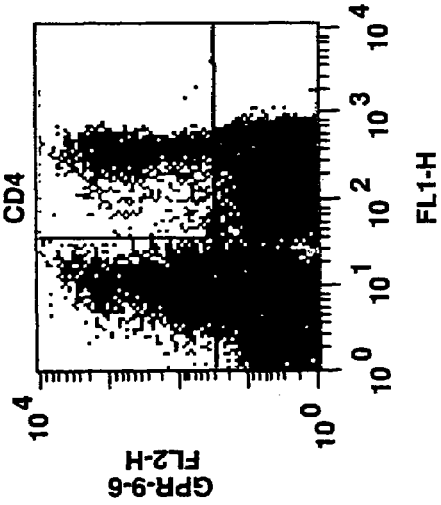
Figure 3F:
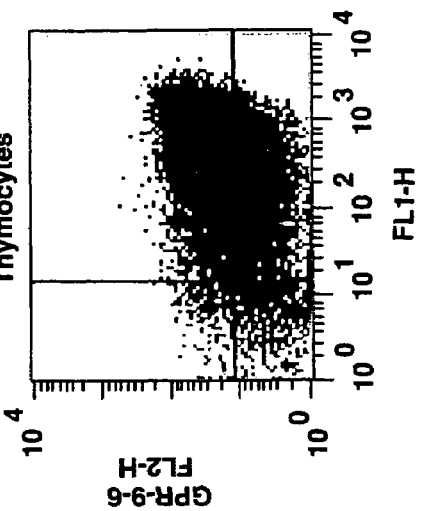
Figure 3E:
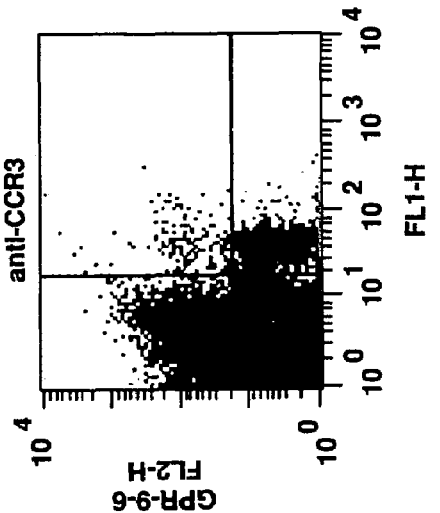
Figure 3D:
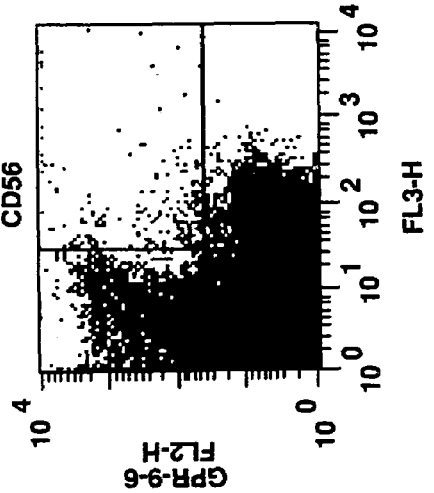
Figure 3G:
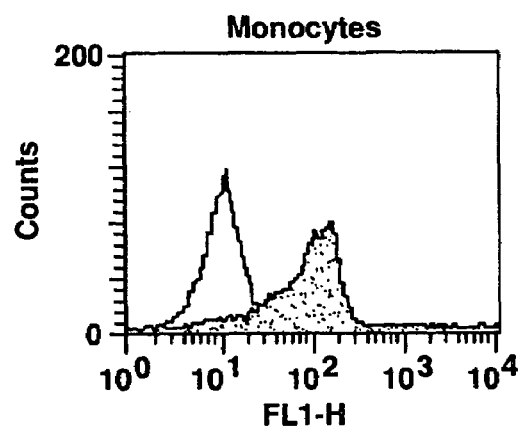
Figure 3H:
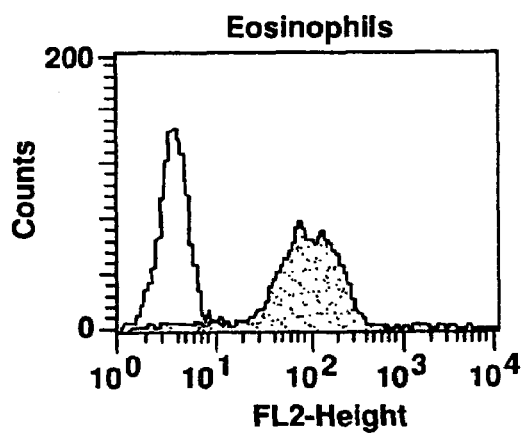
Figure 3I:
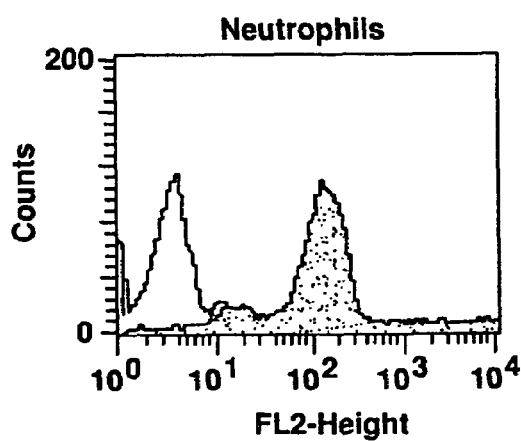
Figure 4A:
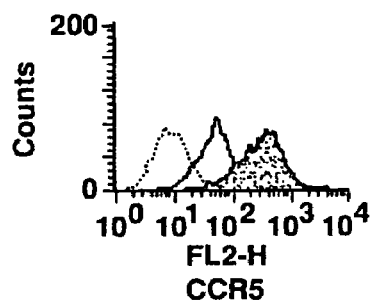
FIGS. 4A-4H are plots illustrating that GPR-9-6 is not expressed on immature dendritic cells (IMDC), mature dendritic cells (MDC) or $T_H1/T_H2$ lymphocytes. Mature (—) and immature dendritic cells (stippled profile) were stained with anti-CCR5 (FIG. 4A), anti-CD83 (FIG. 4B), anti-CD86 (FIG. 4C) or anti-GPR-9-6 (FIG. 4D). Staining with IgG2b control on IMDCs ( . . . ) is also shown.
Figure 4E:
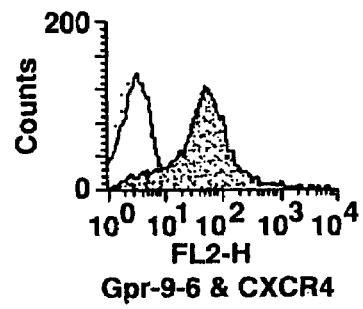
Figure 4B:
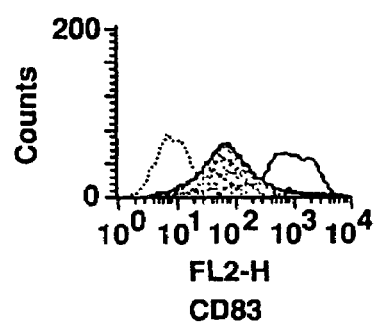
Figure 4F:
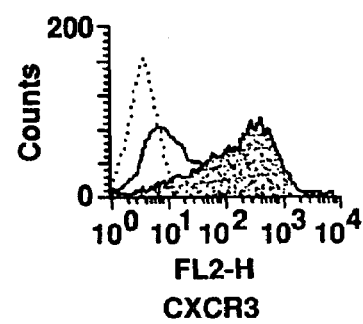
Figure 4C:
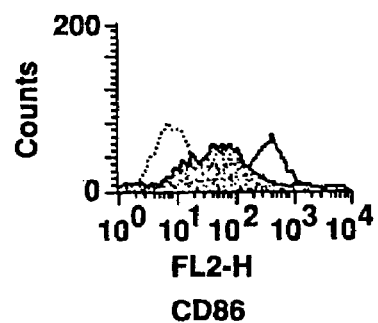
Figure 4G:
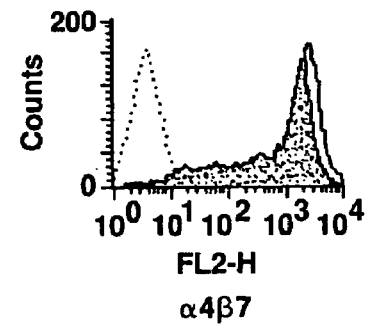
Figure 4D:
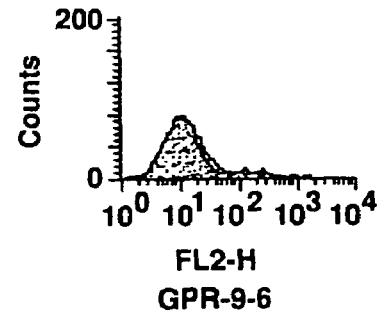
Figure 4H:
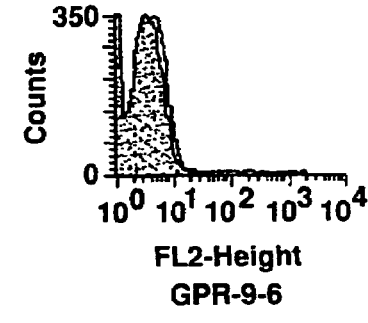

GPR-9-6 is Expressed on all B Lymphocytes, Subsets of CD4 Lymphocytes and a Minor Subset of CD8 Lymphocytes in Peripheral Blood, as well as on Thymocytes In initial two color studies of peripheral blood, GPR-9-6 was found to be expressed on a small subset (2-4%) of CD4 lymphocytes as well as on a very small subset of CD8 lymphocytes, while B lymphocytes expressed low and heterogeneous levels of GPR-9-6 (FIGS. 3A-3C). Monocytes, basophils, eosinophils, neutrophils and NK cells did not express GPR-9-6 under the conditions used (FIGS. 3D-3D). GPR-9-6 was expressed on a large subset of thymocytes expressing all levels of TcR, although a small subset of TcR$^{high}$GPR-9-6$^{-ve}$ thymocytes was evident. In three-color experiments, GPR-9-6 was found on the majority of CD4, CD8 and CD4$^{+ve}$CD8$^{+ve}$ thymocytes and on approximately 50% of immature CD4$^{-ve}$CD8$^{-ve}$ thymocytes (data not shown). No expression of GPR-9-6 was seen on either immature or mature dendritic cells (FIG. 4D). However, as expected, immature dendritic cells expressed CCR5, which was down-regulated on LPS activation, while CD83 and CD86 were up-regulated (FIGS. 4A-4C). In examining a large panel of cell lines GPR-9-6 was found on several T cell lines (Table 1). Umbilical CD4+ lymphocytes did not express GPR-9-6 (FIG. 4E) and chronic activation of these cells in the presence of IL-12 or IL-4 to generate $T_H1$ or $T_H2$ lymphocytes failed to induce the expression of GPR-9-6 (FIG. 4H). However, as expected, CXCR3 were clearly up-regulated on $T_H1$ lymphocytes (FIG. 4F), while α4β7, an integrin utilized in lymphocyte trafficking to mucosal sites, was up-regulated on both $T_H1$ and $T_H2$ lymphocytes (FIG. 4G).

Figure 5A:
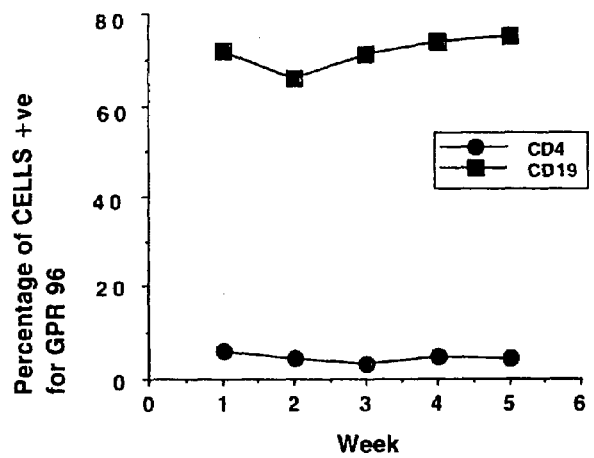
FIGS. 5A-5C are graphs illustrating the modulation of GPR-9-6 on lymphocytes over time and upon T lymphocyte activation. Mononuclear cells were isolated from one individual at set times over 14 days and stained in two color experiments using mAb 3C3 and anti-CD4 FITC or anti-CD19 FITC to examine GPR-9-6 expression on B and CD4 lymphocytes (FIG. 5A).
Figure 5B:
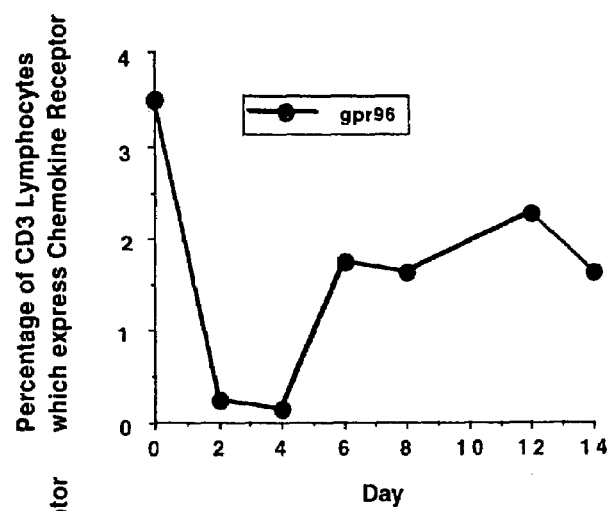
Figure 5C:
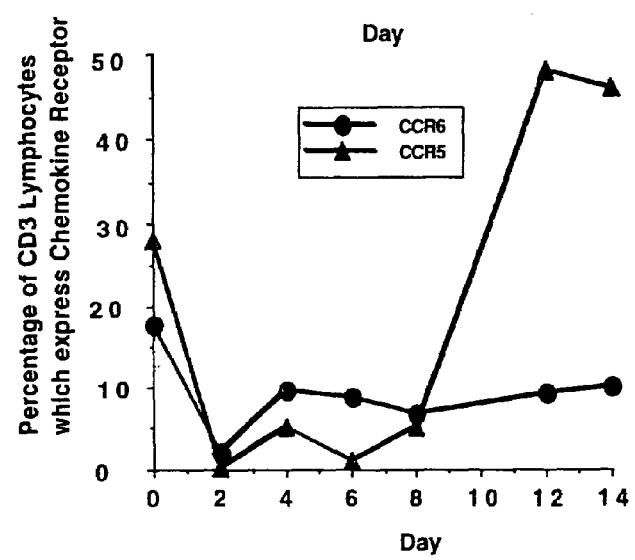

Expression of GPR-9-6 on CD4 lymphocytes and B lymphocytes was measured over time, and was found to be relatively constant (FIG. 5A). However, activation of T lymphocytes with anti-CD3 mAb resulted in transient down-regulation of GPR-9-6 over 2 days, with expression recovering after 10 days of culture in IL-2 (FIG. 5B). Chemokine receptors CCR6 and CCR5 shown similar changes in expression upon T lymphocyte activation (FIG. 5C).

The CD4 Lymphocyte Subset that Express GPR-9-6 are Predominantly of Memory Phenotype and Express High Levels of Mucosal Lymphoid Homing Receptor α4β7 but not Skin Homing Receptor CLA The small subset of CD4 lymphocytes that express GPR-9-6 were examined in more detail by three-color staining (FIGS. 6A-6F). The CD4 lymphocytes that express GPR-9-6 were mainly of memory phenotype, and those cells that expressed the highest levels of GPR-9-6 were all of memory phenotype. Interestingly, memory $CLA^{+ve}$ CD4 lymphocytes, which traffic to skin, did not express GPR-9-6. In contrast, a subset of memory α4β7$^{high}$ CD4 lymphocytes, which traffic to mucosal sites, clearly expressed GPR-9-6. The subset of memory CD4 lymphocytes defined by expression of αEβ7 were also clearly subdivided into GPR-9-6 positive and negative subsets. GPR-9-6$^{high}$ CD4 lymphocytes did not express CD62L, a homing receptor which is involved in trafficking to peripheral lymph nodes, while a small subset of GPR-9-6$^{dull}$CD62L$^{+ve}$ lymphocytes was evident.

GPR-9-6+ve CD4 lymphocytes were also examined for co-expression of other chemokine receptors known to be expressed on CD4 lymphocytes (FIGS. 7A-7F). While GPR-9-6 was clearly found on both positive and negative subsets of CCR5, CCR6, CXCR3 and CXCR5, CD4 lymphocyte expression of CCR2 and GPR-9-6 was mutually exclusive.

GPR-9-6 Chemokine Receptor Specifically Binds to TECK

Figure 9B:
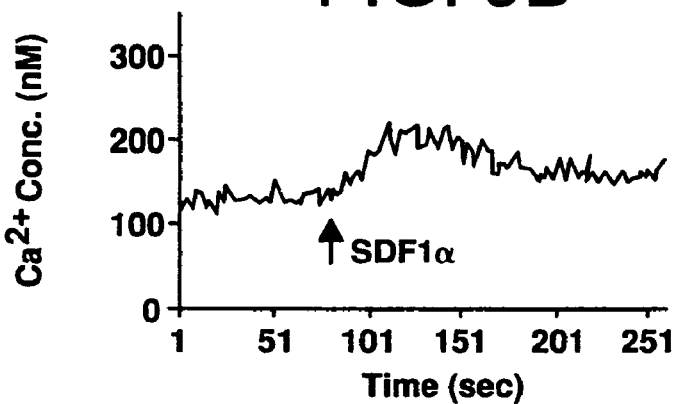
Figure 9C:
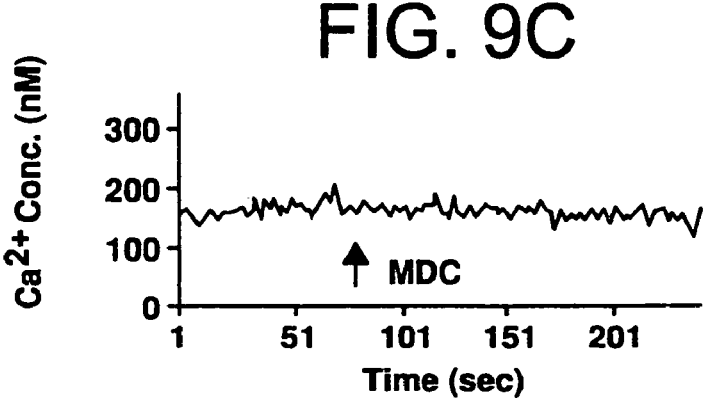
Figure 10B:
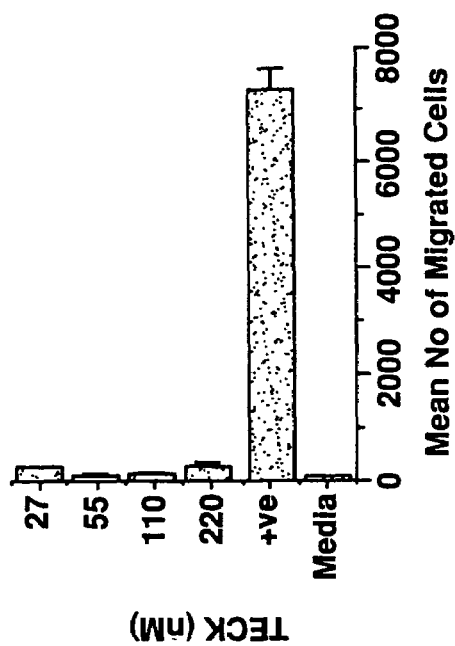
Figure 10A:
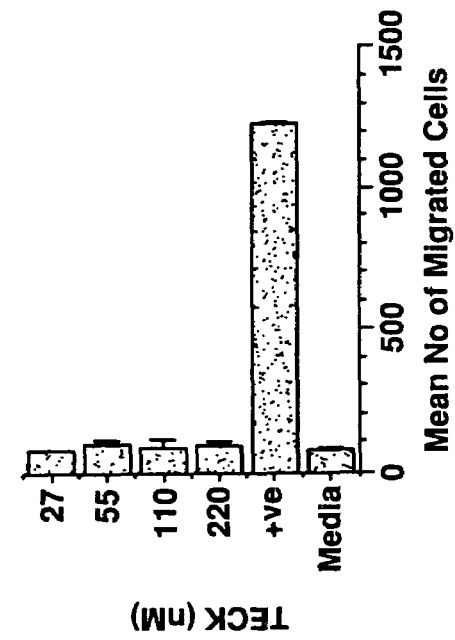

Out of all the published chemokines tested, only TECK proved able to induce chemotaxis of GPR-9-6/L1.2 transfectants (FIG. 8A). MCP-1-4, MIP-1α, MIP-1β, eotaxin-1, eotaxin-2, RANTES, I-309, TARC, MDC, MIP4, SLC, HCC1, fractalkine, lymphotactin, MIG, IP-10, ITAC, ADEC, IL-8, gro-α, gro-β, gro-γ, leukotactin, SDF-1α, SDF-1β, MIP3 and MIP4 all proved unable to induce chemotaxis of the GPR-9-6/L1.2 transfectants. TECK induced chemotaxis of L1.2/GPR-9-6 transfectants was inhibited by the mAb 3C3, but not by an anti-CCR3 mAb 7B11 (FIG. 8B). TECK did not act on any of the other transfectants tested (CCR1, CCR2, CCR 4, CCR5, CCR6, CCR7 and CXCR1, CXCR2, CXCR3, CXCR4, data not shown). Interestingly, TECK was also found to act on the T cell lines MOLT-4 (FIG. 8D) and MOLT-13 (FIG. 8F), which express GPR-9-6 (Table 1). TECK was not chemotactic for other cell lines, such as SKW3 (FIG. 8E), which do not express GPR-9-6. Using the T cell line MOLT-4, TECK induced chemotaxis was shown to be blocked by pertussis toxin (FIG. 8C). Additionally, the anti-GPR-9-6 mAb 3C3 blocked the chemotaxis of the MOLT-13 cells to TECK, but had no effect on SDF1α induced chemotaxis of these cells (FIG. 8F). In calcium mobilization experiments, TECK was also found to induce Ca$^{2+}$ flux in GPR-9-6$^{+ve}$ cell lines such as MOLT-4 (FIGS. 9A-9C), while chemokines such as MDC for which these cells do not express the relevant receptor had no effect.

TABLE 1

GPR-9-6 Expression by Cell Lines

| CELL | GPR-9-6 | CXCR4 |
|---|---|---|
| MOLT-4 | + | + |
| MOLT-13 | + | + |
| CEM | − | + |
| PEER | − | + |
| HUT78 | − | + |
| PMI | − | + |
| SKW.3 | − | + |
| JURKAT | − | + |
| RAMOS | − | + |
| RAJI | − | + |
| JY | − | + |
| THP-1 | − | − |
| U937 | − | + |
| KG1 | − | − |
| HL-60 | − | +/− |
| K562 | − | − |
| EOL-1 | − | + |
| KU812 | − | − |

Leukocyte subsets were also tested (FIGS. 10A-10F) to determine if they chemotaxed to TECK. As observed in the mouse, neutrophils, monocytes, eosinophils, CD8 and NK cells did not chemotax to TECK, but did chemotax to other chemokines. However, TECK was chemotactic for a minor subset of CD4 lymphocytes. As murine TECK induces thymocyte chemotaxis, chemotaxis of human thymocytes to TECK and SDF1α, both of which mediate thymocyte chemotaxis (data not shown) was examined. Anti-GPR-9-6 mAb 3C3 blocked thymocyte and CD4 lymphocyte chemotaxis to TECK. The anti-GPR-9-6 mAb 3C3 had no effect on TARC-induced chemotaxis of CD4 lymphocytes, indicating that the effect is specific (FIGS. 11A-11C). These results indicate that GPR-9-6 is the major physiological receptor for TECK.

Tissue Distribution of TECK and GPR-9-6 Transcripts

Due to the expression of GPR-9-6 on mucosal homing lymphocytes, the distribution of TECK and GPR-9-6 transcripts in lymphoid and mucosal tissue was examined (FIGS. 12A-12B). TECK was selectively expressed in thymus and small intestine (FIG. 12A), while GPR-9-6 was expressed at high levels in thymus and weakly in spleen and peripheral blood leukocytes (FIG. 12B). While GPR-9-6 transcripts were not detected by Northern blot analysis in small intestine, GPR-9-6 message was detected in small intestine, thymus, lymph node and spleen using the more sensitive technique of RT-PCR (FIG. 12C). Messages for both TECK and GPR-9-6 were not detected in brain or colon. In other Northern blots, TECK and GPR-9-6 were not detected in $T_H1$, $T_H2$, Tr1 (Groux, et al., Nature 389:737-742 (1997)) lymphocytes, LAK cells, monocytes, CD34 derived dendritic cells, monocyte derived dendritic cells, astrocytes, human umbilical vein endothelial cells (HUVEC) and pulmonary vein endothelial cells (PUVEC)(data not shown). Finally, GPR-9-6 transcript was shown to be present only in cell lines which had previously been shown to be GPR-9-6$^+$ by staining with mAb 3C3, further validating the specificity of the mAb (FIG. 12B).

Only α4β7$^{high}$ CD4 and CD8 Lymphocytes Migrate to TECK

As GPR-9-6 is expressed mainly on memory α4β7$^{high}$ CD4 lymphocytes, CD45RA$^{-ve}$ memory CD4 and CD8 lymphocytes which expressed none, intermediate or high levels of α4β7 were isolated. Only α4β7$^{high}$ memory CD8 lymphocytes and α4β7$^{+ve}$ CLA$^{-ve}$ memory CD4 lymphocytes chemotaxed to TECK (FIGS. 13A-13B).

Discussion

Several different adhesion molecules are involved in trafficking of lymphocyte subsets to distinct physiologic location, such as peripheral lymph node (Gallatin, W. M., et al., Nature, 304:30-34 (1983)), Peyer's Patches (Hamman, A., et al., J. Immunol., 152:3282-3292 (1994); Andrew, D. P., et al., Eur. J. Immunol., 26:897-905 (1996)) and inflammatory sites (Frenette, P. S., et al., Cell, 84:563-574 (1996); Tietz, W. Y., et al., J. Immunol., 161(2):963-970 (1998); Picker, L. J., et al., J. Immunol., 145:3247-3255 (1990)). It is thought that specific chemokine receptors expressed on these lymphocyte subsets may interact with chemokines expressed in the areas mediating leukocyte activation, arrest, and transendothelial migration. Thus, CD4 subsets defined by the expression of certain adhesion molecules, may also express known, orphan or as yet undiscovered chemokine receptors that are important for trafficking of the lymphocytes into these sites. The work described herein relates to one such chemokine receptor that may be involved in the selective trafficking memory CD4 and CD8 lymphocyte subsets to mucosal sites.

GPR-9-6 was originally chosen as a potentially interesting orphan chemokine receptor due to its strong phylogenetic linkage with other known chemokine receptors including CCR6 and CCR7. In Northern blot analysis, GPR-9-6 was found in thymus, indicative of some role in T cell development. The weak expression in spleen and blood may reflect the expression of GPR-9-6 on memory T lymphocytes and B lymphocytes. As GPR-9-6 is expressed by the majority of thymocytes, and these GPR-9-6$^{+ve}$ thymocytes express all levels of TcR, GPR-9-6 is apparently expressed at all stages of T cell development. On exit from the thymus, GPR-9-6 must be down-regulated, as in the periphery only a small subset of CD4 lymphocytes and an even smaller subset of CD8 lymphocytes express GPR-9-6. In three-color experiments, GPR-9-6 is found predominantly on memory CD4 lymphocytes. Of greater interest, while the CLA$^{+ve}$ memory CD4 lymphocytes (Picker, L. J., et al., J. Immunol., 145: 3247-3255 (1990)) do not express GPR-9-6, a subset of the memory α4β7$^{high}$ CD4 lymphocytes (Andrew, D. P., et al., Eur. J. Immunol., 26:897-905 (1996)) express this chemokine receptor. This may reflect a role for GPR-9-6 in the trafficking of lymphocytes to mucosal sites, or their effector action when there. While GPR-9-6 was clearly expressed on mucosal trafficking CD4 lymphocytes, GPR-9-6 transcripts were not detected in small intestine by Northern blot analysis. This may reflect the low numbers of the GPR-9-6$^{+ve}$ CD4+ and/or CD8+ lymphocytes in small intestine tissue compared to thymus, where the majority of the cells are actively dividing GPR-9-6$^{+ve}$ thymocytes. However, using the more sensitive technique of RT-PCR, GPR-9-6 transcripts were detected in small intestine but not in the brain. Interestingly, while GPR-9-6 and TECK transcripts are expressed in small intestine, GPR-9-6 or TECK transcripts were not detected in the colon by either Northern or RT-PCR analysis.

Factors which are present in the mucosal environment can induce the expression of GPR-9-6 on T lymphocytes as well as TECK expression. Cytokines present in T$_H$1/T$_H$2 environments induce expression of certain chemokine receptors, such as CCR4 on T$_H$2 and CXCR3 on T$_H$1 lymphocytes, as well as the production of the chemokines that bind these receptors (Bonecchi, R. G., et al., J. Exp. Med., 187:129-134 (1998); Sallusto, F. D., et al., J. Exp. Med., 187:875-883 (1998); Sallusto, F., Science, 277:2005-2007 (1997); Andrew, D. P., et al., (1998); Zingoni, A., et al., J. Immunol., 161:547-555 (1998)). However, these conditions did not up-regulate GPR-9-6 expression on T lymphocytes. Also, attempts to induce expression of GPR-9-6 on activated umbilical CD4 lymphocytes with cytokines IL-1-18 or with TGF-β, previously shown to induce αE on T lymphocytes (Kilshaw, P. J. and Murant, S. J., Eur. J. Immunol., 21:2591-2597 (1991)), failed to identify a cytokine that up-regulates GPR-9-6 expression. Therefore, the mechanism by which GPR-9-6 expression is controlled on CD4 lymphocytes is unclear. Upon activation via TcR cross-linking, expression of GPR-9-6 is down-regulated, as is the expression of chemokine receptor CXCR4 (Bermejo, M., et al., J. Immunol. 28:3192-3204 (1998)). As TcR cross-linking mimics antigen presentation, we conclude that on entering a lymph node and encountering APC's expressing antigenic peptide+ MHC-II, that T lymphocytes will down-regulate chemokine receptors such as GPR-9-6. This will hold T lymphocytes in the lymph node, where T lymphocytes may mediate other immune functions such as B cell class switching through T:B cognate interactions.

Out of all the chemokines tested only TECK (Vicari, A. P., et al., Immunity, 7(2):291-301 (1997)) acted as a chemoattractant for GPR-9-6/L1.2 transfectants, with 150 nM resulting in optimal chemotaxis. This falls into the range of 1 μnM-1 μM for which other leukocyte chemokines are active. However, as we are using TECK that was generated by peptide synthesis, we cannot be sure that either post-translational modifications or further cleavage of TECK by factors outside the cell in vivo do not generate more active fragments, as is the case for CKB8 (Macphee, C. H., et al., J. Immunol. 161:6273-6279 (1998)). TECK did not act as a chemoattractant for CCR1, CCR2, CCR4, CCR5, CCR6, CCR7, CCR9 and CXCR1, CXCR2, CXCR3, CXCR4 and CXCR5 L1.2 transfectants. However, some weak activity of TECK on CCR3/L1.2 transfectants which was approximately 20% of the chemotactic activity observed with eotaxin-1 was detected. This activity was blocked by anti-CCR3 mAbs, though TECK did not act as a chemoattractant for eosinophils. Therefore, TECK is probably not a physiological chemokine for the CCR3 receptor. This result is not unprecedented, as in previous studies MIP-1α has been shown to act as a chemoattractant for CCR4/HEK293 transfectants (Power, C. A., et al., J. Biol. Chem., 270:19495-19500 (1995)), but not CCR4/L1.2 transfectants (Imai, T. M., et al., J. Biol. Chem., 272:15036-15042 (1997)). In further experiments, only the T cell lines that express GPR-9-6 were found to chemotax to TECK, while among primary cells TECK was chemotactic for only a small subset of CD4 lymphocytes. Presumably, these cells represent the small subset of CD4 lymphocytes that express GPR-9-6, as the chemotaxis was blocked by anti-GPR-9-6 mAb 3C3. Additionally, only α4β7$^{+ve}$ memory CD4 and CD8 lymphocytes chemotax to TECK, which would be the subset predicted to express GPR-9-6. TECK was originally described as a chemokine produced by thymic dendritic cell, whose expression is restricted to thymus and small intestine (Vicari, A. P., et al., Immunity, 7(2):291-301 (1997)). Our Northern data confirms this observation and shows that the receptor for TECK, GPR-9-6, is also expressed at these sites. The expression of both chemokine receptor GPR-9-6 and its ligand TECK in small intestine and thymus predict a role for GPR-9-6 and TECK in T cell development and mucosal immunology.

In summary, the orphan chemokine receptor GPR-9-6 was shown to be expressed on the majority of thymocytes and on a subset of memory CD4 lymphocytes that traffic to mucosal sites. The selective expression of TECK and GPR-9-6 in thymus and small intestine imply a dual role for GPR-9-6, both in T cell development and the mucosal immune response.

Example 2

Functional GPR-9-6 is Expressed on Acute T Cell Lymphoblastic Leukemia Cell Lines As described herein, GPR-9-6 expression was detected on MOLT-4 and MOLT-13 cells (Table 1) using mAb 3C3. The MOLT cell lines are human T cell lines which were derived from a patient diagnosed with acute T cell lymphoblastic leukemia (ATL).

Other T cell leukemia cell lines including CEM, PEER, HUT78, PM1, SKW3 and JURKAT did not express GPR-9-6. In further studies the ability of the T cell lines to undergo TECK-induced chemotaxis was assessed in in vitro chemotaxis assays. The ATL cells, MOLT-4 and MOLT-13, underwent TECK-induced chemotaxis but other T cell lines (CEM, PEER) did not.

Example 3

Intraepithelial Lymphocytes (IEL) and Lamina Propria Lymphocytes (LPL) Express GPR-9-6 (CCR9) and Undergo TECK-induced Chemotaxis Lymphocyte Isolation Lymphocytes from the epithelium and lamina propria of human intestines were isolated as previously described (Zabal, B. A. et al., *J. Exp. Med.*, 190:1241-1256 (1999). Briefly, pieces of intestine were cut open, laid flat and washed with ice cold HBSS. The serosa was separated from the mucosa with scissors and discarded. The mucosa was cut into strips and incubated with cold 0.15% (w/v) dithiolthreitol in HBSS (DTT/HBSS) for 30 minutes. The mucosa was then washed with cold HBSS to remove mucus. The mucosal strips were then incubated in cold 1 mM EDTA in HBSS with stirring for 90 minutes to remove the epithelium and intraepithelial lymphocytes (IEL). The incubation in 1 mM EDTA in HBSS with stirring was repeated several times, until no more epithelial cells were shed from the strips. The remaining mucosal strips were crushed through a 50 mesh strainer (Sigma, St. Louis, Mo.) to isolate lamina propria lymphocytes (LPL).

FACS Analysis

Isolated lymphocytes were resuspended in FACS buffer at a concentration of $\leq 1\times 10^6$/ml. Non-specific antibody binding was blocked using horse IgG (Sigma, St. Loius, Mo.). Unconjugated anti GPR-9-6 (CCR9) antibody (mAb 3C3) was detected using biotinylated horse anti-mouse IgG secondary antibody (Vector Laboratories, Burlingame, Calif.) and streptavidin PerCP (Phamingen, San Diego, Calif.).

Chemotaxis of Intestinal Lymphocytes

Chemotaxis assays were performed using 24 well Transwell plates (Coming Costar, Cambridge, Mass.) with polycarbonate membranes having 5 µm diameter pores. Briefly, 600 µl of TECK diluted in RPMI 1640 with 0.5% BSA was placed in the bottom chamber of the Transwell plates and 100 µl of cells ($1\times 10^6$ for IEL, $5\times 10^5$ for LPL) were placed in each insert. For antibody inhibition experiments, IEL or LPL were incubated with 40 µg/ml of mAb 3C3, control murine IgG2b (clone 49.2, PharMingen, San Diego, Calif.) or medium alone for 10 minutes at 4° C., prior to adding the insert to the wells. The plates were then incubated at 37° C. in 5% $CO_2$ for 3 hours. The number of cells that migrated to the lower chamber during the assay was determined by FACS analysis, counting the number of events that passed through the detector with a light scatter profile characteristic of small lymphocytes during a 40 second interval. The number of events equivalent to 100% cell migration was equal to one sixth of the number of events registered when the input cell suspension was counted by FACS for 40 seconds.

Results

GPR-9-6 (CCR9) expression was detected on only a small subset of peripheral blood leukocytes by flow cytometry. In contrast, essentially all IEL and LPL expressed high levels of GPR-9-6 (FIGS. 16A-16C). Furthermore, in vitro chemotaxis assays revealed that both IEL and LPL undergo TECK-induced chemotaxis which can be inhibited by anti-GPR-9-6 antibody (mAb 3C3) but not by an isotype control antibody (IgG2b) (FIGS. 17A and 17B). Thus, GPR-9-6 (CCR9) is the main physiological receptor for TECK expressed by IEL and LPL. The data demonstrate that local trafficking of leukocytes within the intestinal epithelium is mediated through the interaction of TECK and GPR-9-6 (CCR9).

Example 4

Additional Anti-GPR-9-6 mAbs

C57/Black mice were immunized with 10 million transfected L1.2 cells which stabely expressed GPR-9-6 (GPR-9-6/L1.2) (see Example 1). Prior to immunization, the transfected L1.2 cells were treated with mitomycin C (50 µg/ml) in PBS (Sigma). Three weeks later, the mice were again immunized with mitomycin C treated GPR-9-6/L1.2 transfectants. Thereafter, the mice were immunized with 10 million GPR-9-6/L1.2 transfectants every three weeks. The mice were immunized with GPR-9-6/L1.2 transfectants a minimum of 4 times. For hybridoma formation, spleens were removed from the immunized mice 3-4 days after the last immunization and splenocytes were fused to SP2/0 myeloma cells. Hybridomas that produced antibodies which specifically bound GPR-9-6 (CCR9)(i.e., stained GPR-9-6/L1.2 transfectants but did not stain L1.2 cells transfectants that expressed other chemokine receptors) were identified by FACS analysis.

Murine hybridoma GPR96-1 which produces mAb GPR96-1 was isolated, and the capacity of mAb GPR96-1 to inhibit TECK-induced chemotaxis of GPR-9-6/L1.2 in an in vitro chemotaxis assay was assessed. For this antibody inhibition assay, the GPR-9-6/L1.2 transfectants where incubated with various concentrations of mAb GPR96-1 or mAb 3C3 for 10 minutes on ice prior to exposure to TECK. The chemotaxis assay was performed essentially as described above except ECV304 cells were not used. The results, which are presented graphically in FIG. 18, revealed that mAb GPR96-1 is more efficient at inhibiting TECK-induced chemotaxis than mAb 3C3 under the conditions of the assay.

Murine hybridoma GPR96-1, also referred to as hybridoma LS272 GPR96 1-5, can be cultivated at 37° C. in an 5% $CO_2$ atmosphere in DMEM supplemented with FCS (10%), IL-6 (100 ng/ml), penicillin (50U/ml), streptomycin (50 µg/ml), L-glutamine (2 mM), HEPES (10 mM), MEM sodium pyruvate (10 mM), MEM nonessential amino acids (0.1 mM) and 2-mercaptoethanol ($5.5 \times 10^{-5}$M).

Example 5

Anti-TECK mAbs

Balb/c mice were immunized intra-peritoneally first with 10 µg of human TECK (Peprotech, Rocky Hill, N.J. 330-45) in Complete Freunds Adjuvant (Sigma F 5881). Three weeks later the mice were immunized intra-peritoneally with 10 µg of human TECK (Peprotech, , Rocky Hill, N.J. 330-45) in Incomplete Freunds Adjuvant (Sigma F 5506). Thereafter, mice were immunized intra-peritoneally every three weeks with 10 µg of TECK in PBS. Each mouse was immunized a minimum of four times. For hybridoma formation, spleens were removed from the immunized mice 3-4 days after the last immunization and splenocytes were fused to SP2/0 myeloma cells. Hybridomas that produced antibodies which specifically bound to TECK were identified by ELISA using plates coated with 2 µg/ml of TECK. Anti-TECK antibodies were then tested for the capacity to inhibit TECK-induced (150 nM) chemotaxis of GPR-9-6/L1.2 transfectants in an in vitro assay.

Murine hybridomas 11.2, 11.3.1, 16.2 and 16.3.1 were isolated (hybridomas 11.3.1 and 16.3.1 are subclones of hybridomas 11.2 and 16.2, respectively) and the capacity of the mAbs they produced to inhibit TECK-induced chemotaxis of GPR-9-6/L1.2 cells was assessed in an in vitro chemotaxis assay. TECK was diluted (final concentration about 150 nM) in culture media containing a control IgG1 mAb (20 mg/ml) or diluted 1:4 in conditioned culture media of hybridomas which produce mAbs that bind TECK. The TECK solutions were placed in the bottom of a Transwell plate and incubated at room temperature for 10 minutes. GPR-9-6/L1.2 transfectants were then suspended in culture media and placed in the inserts, which were placed into the wells of the plate. The transfectants were allowed to migrate for 2-3 hours and then the cells that accumulated in the lower well were counted on a FACSCAN.

The results of the assays, which are presented graphically in FIG. 19, revealed that mAbs 11.2, 11.3.1, 16.2 and 16.3.1 each inhibited TECK-induced chemotaxis, while mAb 20.2, which also binds TECK, and non-specific IgG did not.

Murine hybridomas 11.3.1, also referred to as hybridoma LS250 11.3.1, and 16.3.1, also referred to as hybridoma LS250 16.3.1, can be cultivated at 37° C. in an 5% $CO_2$ atmosphere in DMEM supplemented with FCS (10%), IL-6 (100 ng/ml), penicillin (50 U/ml), streptomycin (50 µg/ml), L-glutamine (2 mM), HEPES (10 mM), MEM sodium pyruvate (10 mM), MEM nonessential amino acids (0.1 mM) and 2-mercaptoethanol ($5.5 \times 10^{-5}$M).

Example 6

Naturally Occurring Variants of TECK

RNA was prepared from human samples of thymus and inflamed or non-inflamed small intestine using Qiagen Mini Kits. The RNA was reverse transcribed and the coding region of TECK was amplified by PCR using BAZ203 (SEQ ID NO:6) and BAZ204 (SEQ ID NO:7) as described (see Example 1). The product of the PCR was cut with enzymes BamH1 and Xba 1 and ligated into pBluescript II KS. The inserts were sequenced using primers which annealed to sequences in pBluescript II (M13 and T3). Sequencing data revealed that different forms of TECK are expressed in these tissues. A polymorphism at amino acid 104 with either a threonine (T) or a methionine (M) was found (SEQ ID NO:9). Splice variants having a frame shift deletion of bases 326-328, which causes amino acid 109 (alanine) to be deleted were also found.

Further to this, examination of the sequence of inserts generated by PCR from separate RNA samples revealed differential expression of the two forms of TECK resulting from the frameshift mutation, with the alanine deleted form been more prevalent in small intestine than thymus.

Example 7

TECK is Highly Expressed by Epithelial Cells of the Small Intestine

In Situ Hybridization

The TECK probe was initially amplified from a pool of murine cDNA prepared by RT-PCR from thymus using a synthetic oligonucleotide 5 prime primer (t aag gat ccg caa ggt gcc ttt gaa gac tgc t; SEQ ID NO:12) and a synthetic oligonucleotide 3 prime primer (caa gaa ttc tta att gtt ctt tct ggg cat; SEQ ID NO:13) and subcloned via BamH1 and EcoR1. A second step of PCR amplification, to introduce RNA polymerase sites, was performed using synthetic oligonucleotide primers m_TECK T3 (aat taa ccc tca cta aag gga act gtg gct ttt tgc ctg c; SEQ ID NO:14) and m_TECK T7 (taa tac gac tca cta tag ggt gtt ggt ctt tct ggg cat c; SEQ ID NO:15). Sense and antisense digoxigenin labeled probes were synthesized using the DIG RNA Labeling Kit/Genius 4 Kit (Roche Molecular Biochemicals).

Five micron frozen sections of mouse small intestine were cut and melted onto Superfrost Plus slides (VWR), air dried at room temperature for 1-2 hours and used the same day for hybridization. The sections were pretreated as described (Breitschopf et al., *Detection of mRNA on paraffin embedded material of the central nervous system with DIG-labeled RNA probes.*, In "Nonradioactive In Situ Hybridization Application Manual" $2^{nd}$ edition Copyright 1996 Boehringer Mannheim GmbH, Biochemica.), ommiting the initial xylene step and including a digestion with Proteinase K (0.1 µg/ml) for 5 minutes at room temperature. The sections were hybridized for 16-18 hours at 60° C. in a hybridization buffer containing 200 ng/ml digoxigenin labeled probe, 50% formamide (Gibco BRL) 5×SSC, 5× Denhardt's solution (Sigma), 0.5 mg/ml salmon sperm DNA (Gibco BRL) and 25 µg/ml yeast RNA (Sigma). After hybridization, the sections were washed in 0.2×SSC for 1 hour at 60° C. and then in 0.2×SSC for 5 minutes at room temperature. The digoxigenin labeled probe was detected using the DIG Nucleic Acid Detection Kit/Genius 3 (Roche Molecular Biochemicals) as described, except that the incubation with antibody (1:100) was carried out at 4° C. overnight and 10% 70-100 kD polyvinyl alcohol (Sigma) was added to the alkaline phosphatase reaction buffer.

Results

In situ hybridization was used to directly assess the cellular sites of TECK expression in murine intestine. TECK expression was localized to the epithelium on the villi and crypts of Lieberkuhn of the small intestine. The expression on the villi was greatest at the base, with lower levels of TECK hybridization detected toward the top of the villi. No expression of TECK was detected in the Peyer's patches (PP) attached to the small intestine (FIGS. 24A-24C).

The data demonstrate TECK is selectively expressed at high levels by epithelial cells of the small intestine. This expression pattern further supports a highly selective role for TECK in regulating the recruitment of circulating "small intestine homing" lymphocytes as well as the local recruitment of IEL and LPL.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated antibody or antigen-binding fragment thereof wherein said antibody or antigen-binding fragment the antibody produced by murine hybridoma 11.3.1 (ATCC PTA-1469).

2. An isolated antibody or antigen-binding fragment thereof wherein said antibody or antigen-binding fragment the antibody produced by murine hybridoma 16.3.1 (ATCC PTA-1468).

3. An isolated cell wherein said isolated cell is murine hybridoma 11.3.1 (ATCC PTA-1469).

4. An isolated cell wherein said isolated cell is murine hybridoma 16.3.1 (ATCC PTA-1468).

* * * * *

SEQUENCE LISTING

```
<160> NUMBER OF SEQ ID NOS: 15

<210> SEQ ID NO 1
<211> LENGTH: 2577
<212> TYPE: DNA
<213> ORGANISM: Homo sapiens
<220> FEATURE:
<221> NAME/KEY: CDS
<222> LOCATION: (58)...(1131)

<400> SEQUENCE: 1
aatattttcc ttgacctaat gccatcttgt gtcccttgc agagccctat tcctaac atg      60
                                                                 Met
                                                                  1 gct gat gac tat ggc tct gaa tcc aca tct tcc atg gaa gac tac gtt     108
Ala Asp Asp Tyr Gly Ser Glu Ser Thr Ser Ser Met Glu Asp Tyr Val
              5                  10                  15 aac ttc aac ttc act gac ttc tac tgt gag aaa aac aat gtc agg cag     156
Asn Phe Asn Phe Thr Asp Phe Tyr Cys Glu Lys Asn Asn Val Arg Gln
         20                  25                  30 ttt gcg agc cat ttc ctc cca ccc ttg tac tgg ctc gtg ttc atc gtg     204
Phe Ala Ser His Phe Leu Pro Pro Leu Tyr Trp Leu Val Phe Ile Val
     35                  40                  45 ggt gcc ttg ggc aac agt ctt gtt atc ctt gtc tac tgg tac tgc aca     252
Gly Ala Leu Gly Asn Ser Leu Val Ile Leu Val Tyr Trp Tyr Cys Thr
 50                  55                  60                  65 aga gtg aag acc atg acc gac atg ttc ctt ttg aat ttg gca att gct     300
Arg Val Lys Thr Met Thr Asp Met Phe Leu Leu Asn Leu Ala Ile Ala
                  70                  75                  80 gac ctc ctc ttt ctt gtc act ctt ccc ttc tgg gcc att gct gct gct     348
Asp Leu Leu Phe Leu Val Thr Leu Pro Phe Trp Ala Ile Ala Ala Ala
             85                  90                  95 gac cag tgg aag ttc cag acc ttc atg tgc aag gtg gtc aac agc atg     396
Asp Gln Trp Lys Phe Gln Thr Phe Met Cys Lys Val Val Asn Ser Met
        100                 105                 110 tac aag atg aac ttc tac agc tgt gtg ttg ctc atc atg tgc atc agc     444
Tyr Lys Met Asn Phe Tyr Ser Cys Val Leu Leu Ile Met Cys Ile Ser
    115                 120                 125 gtg gac agg tac att gcc att gcc cag gcc atg aga gca cat act tgg     492
Val Asp Arg Tyr Ile Ala Ile Ala Gln Ala Met Arg Ala His Thr Trp
130                 135                 140                 145 agg gag aaa agg ctt ttg tac agc aaa atg gtt tgc ttt acc atc tgg     540
Arg Glu Lys Arg Leu Leu Tyr Ser Lys Met Val Cys Phe Thr Ile Trp
                150                 155                 160 gta ttg gca gct gct ctc tgc atc cca gaa atc tta tac agc caa atc     588
Val Leu Ala Ala Ala Leu Cys Ile Pro Glu Ile Leu Tyr Ser Gln Ile
            165                 170                 175 aag gag gaa tcc ggc att gct atc tgc acc atg gtt tac cct agc gat     636
Lys Glu Glu Ser Gly Ile Ala Ile Cys Thr Met Val Tyr Pro Ser Asp
        180                 185                 190
```

```
gag agc acc aaa ctg aag tca gct gtc ttg acc ctg aag gtc att ctg       684
Glu Ser Thr Lys Leu Lys Ser Ala Val Leu Thr Leu Lys Val Ile Leu
    195                 200                 205 ggg ttc ttc ctt ccc ttc gtg gtc atg gct tgc tgc tat acc atc atc       732
Gly Phe Phe Leu Pro Phe Val Val Met Ala Cys Cys Tyr Thr Ile Ile
210                 215                 220                 225 att cac acc ctg ata caa gcc aag aag tct tcc aag cac aaa gcc cta       780
Ile His Thr Leu Ile Gln Ala Lys Lys Ser Ser Lys His Lys Ala Leu
                    230                 235                 240 aaa gtg acc atc act gtc ctg acc gtc ttt gtc ttg tct cag ttt ccc       828
Lys Val Thr Ile Thr Val Leu Thr Val Phe Val Leu Ser Gln Phe Pro
                245                 250                 255 tac aac tgc att ttg ttg gtg cag acc att gac gcc tat gcc atg ttc       876
Tyr Asn Cys Ile Leu Leu Val Gln Thr Ile Asp Ala Tyr Ala Met Phe
            260                 265                 270 atc tcc aac tgt gcc gtt tcc acc aac att gac atc tgc ttc cag gtc       924
Ile Ser Asn Cys Ala Val Ser Thr Asn Ile Asp Ile Cys Phe Gln Val
        275                 280                 285 acc cag acc atc gcc ttc ttc cac agt tgc ctg aac cct gtt ctc tat       972
Thr Gln Thr Ile Ala Phe Phe His Ser Cys Leu Asn Pro Val Leu Tyr
290                 295                 300                 305 gtt ttt gtg ggt gag aga ttc cgc cgg gat ctc gtg aaa acc ctg aag      1020
Val Phe Val Gly Glu Arg Phe Arg Arg Asp Leu Val Lys Thr Leu Lys
                    310                 315                 320 aac ttg ggt tgc atc agc cag gcc cag tgg gtt tca ttt aca agg aga      1068
Asn Leu Gly Cys Ile Ser Gln Ala Gln Trp Val Ser Phe Thr Arg Arg
                325                 330                 335 gag gga agc ttg aag ctg tcg tct atg ttg ctg gag aca acc tca gga      1116
Glu Gly Ser Leu Lys Leu Ser Ser Met Leu Leu Glu Thr Thr Ser Gly
            340                 345                 350 gca ctc tcc ctc tga ggggtcttct ctgaggtgca tggttctttt ggaagaaatg      1171
Ala Leu Ser Leu  *
355 agaaatacat gaaacagttt ccccactgat gggaccagag agagtgaaag agaaaagaaa    1231 actcagaaag ggatgaatct gaactatatg attacttgta gtcagaattt gccaaagcaa    1291 atatttcaaa atcaactgac tagtgcagga ggctgttgat tggctcttga ctgtgatgcc    1351 cgcaattctc aaaggaggac taaggaccgg cactgtggag caccctggct ttgccactcg    1411 ccggagcatc aatgccgctg cctctggagg agcccttgga ttttctccat gcactgtgaa    1471 cttctgtggc ttcagttctc atgctgcctc ttccaaaagg ggacacagaa gcactggctg    1531 ctgctacaga ccgcaaaagc agaaagtttc gtgaaaatgt ccatctttgg gaaattttct    1591 accctgctct tgagcctgat aacccatgcc aggtcttata gattcctgat ctagaacctt    1651 tccaggcaat ctcagaccta atttccttct gttctccttg ttctgttctg ggccagtgaa    1711 ggtccttgtt ctgattttga aacgatctgc aggtcttgcc agtgaacccc tggacaactg    1771 accacaccca caaggcatcc aaagtctgtt ggcttccaat ccatttctgt gtcctgctgg    1831 aggttttaac ctagacaagg attccgctta ttccttggta tggtgacagt gtctctccat    1891 ggcctgagca gggagattat aacagctggg ttcgcaggag ccagccttgg ccctgttgta    1951 ggcttgttct gttgagtggc acttgctttg ggtccaccgt ctgtctgctc cctagaaaat    2011 gggctggttc ttttggccct cttctttctg aggcccactt tattctgagg aatacagtga    2071 gcagatatgg gcagcagcca ggtagggcaa aggggtgaag cgcaggcctt gctggaaggc    2131 tatttacttc catgcttctc cttttcttac tctatagtgg caacatttta aaagctttta    2191 acttagagat taggctgaaa aaaataagta atggaattca cctttgcatc ttttgtgtct    2251
```

-continued

```
ttcttatcat gatttggcaa aatgcatcac ctttgaaaat atttcacata ttggaaaagt    2311
gctttttaat gtgtatatga agcattaatt acttgtcact ttctttaccc tgtctcaata    2371
ttttaagtgt gtgcaattaa agatcaaata gatacattaa gagtgtgaag gctggtctga    2431
aggtagtgag ctatctcaat cggattgttc acactcagtt acagattgaa ctccttgttc    2491
tacttccctg cttctctcta ctgcaattga ctagtcttta aaaaaaagtg tgaagagtaa    2551
gcaataggga taaggaaata agatct                                        2577
```

<210> SEQ ID NO 2
<211> LENGTH: 357
<212> TYPE: PRT
<213> ORGANISM: Homo sapiens

<400> SEQUENCE: 2

| Met | Ala | Asp | Asp | Tyr | Gly | Ser | Glu | Ser | Thr | Ser | Ser | Met | Glu | Asp | Tyr |
|---|---|---|---|---|---|---|---|---|---|---|---|---|---|---|---|
| 1 | | | | 5 | | | | | 10 | | | | | 15 | |

| Val | Asn | Phe | Asn | Phe | Thr | Asp | Phe | Tyr | Cys | Glu | Lys | Asn | Asn | Val | Arg |
| | | | 20 | | | | | 25 | | | | | 30 | | |

| Gln | Phe | Ala | Ser | His | Phe | Leu | Pro | Pro | Leu | Tyr | Trp | Leu | Val | Phe | Ile |
| | | | 35 | | | | | 40 | | | | | 45 | | |

| Val | Gly | Ala | Leu | Gly | Asn | Ser | Leu | Val | Ile | Leu | Val | Tyr | Trp | Tyr | Cys |
| | 50 | | | | | 55 | | | | | 60 | | | | |

| Thr | Arg | Val | Lys | Thr | Met | Thr | Asp | Met | Phe | Leu | Leu | Asn | Leu | Ala | Ile |
| 65 | | | | | 70 | | | | | 75 | | | | | 80 |

| Ala | Asp | Leu | Leu | Phe | Leu | Val | Thr | Leu | Pro | Phe | Trp | Ala | Ile | Ala | Ala |
| | | | | 85 | | | | | 90 | | | | | 95 | |

| Ala | Asp | Gln | Trp | Lys | Phe | Gln | Thr | Phe | Met | Cys | Lys | Val | Val | Asn | Ser |
| | | | 100 | | | | | 105 | | | | | 110 | | |

| Met | Tyr | Lys | Met | Asn | Phe | Tyr | Ser | Cys | Val | Leu | Leu | Ile | Met | Cys | Ile |
| | | | | 115 | | | | | 120 | | | | | 125 | |

| Ser | Val | Asp | Arg | Tyr | Ile | Ala | Ile | Ala | Gln | Ala | Met | Arg | Ala | His | Thr |
| | 130 | | | | | 135 | | | | | 140 | | | | |

| Trp | Arg | Glu | Lys | Arg | Leu | Leu | Tyr | Ser | Lys | Met | Val | Cys | Phe | Thr | Ile |
| 145 | | | | | 150 | | | | | 155 | | | | | 160 |

| Trp | Val | Leu | Ala | Ala | Ala | Leu | Cys | Ile | Pro | Glu | Ile | Leu | Tyr | Ser | Gln |
| | | | | 165 | | | | | 170 | | | | | 175 | |

| Ile | Lys | Glu | Glu | Ser | Gly | Ile | Ala | Ile | Cys | Thr | Met | Val | Tyr | Pro | Ser |
| | | | 180 | | | | | 185 | | | | | 190 | | |

| Asp | Glu | Ser | Thr | Lys | Leu | Lys | Ser | Ala | Val | Leu | Thr | Leu | Lys | Val | Ile |
| | | | | 195 | | | | | 200 | | | | | 205 | |

| Leu | Gly | Phe | Phe | Leu | Pro | Phe | Val | Val | Met | Ala | Cys | Cys | Tyr | Thr | Ile |
| | 210 | | | | | 215 | | | | | 220 | | | | |

| Ile | Ile | His | Thr | Leu | Ile | Gln | Ala | Lys | Lys | Ser | Ser | Lys | His | Lys | Ala |
| 225 | | | | | 230 | | | | | 235 | | | | | 240 |

| Leu | Lys | Val | Thr | Ile | Thr | Val | Leu | Thr | Val | Phe | Val | Leu | Ser | Gln | Phe |
| | | | | 245 | | | | | 250 | | | | | 255 | |

| Pro | Tyr | Asn | Cys | Ile | Leu | Leu | Val | Gln | Thr | Ile | Asp | Ala | Tyr | Ala | Met |
| | | | 260 | | | | | 265 | | | | | 270 | | |

| Phe | Ile | Ser | Asn | Cys | Ala | Val | Ser | Thr | Asn | Ile | Asp | Ile | Cys | Phe | Gln |
| | | | | 275 | | | | | 280 | | | | | 285 | |

| Val | Thr | Gln | Thr | Ile | Ala | Phe | Phe | His | Ser | Cys | Leu | Asn | Pro | Val | Leu |
| | 290 | | | | | 295 | | | | | 300 | | | | |

| Tyr | Val | Phe | Val | Gly | Glu | Arg | Phe | Arg | Arg | Asp | Leu | Val | Lys | Thr | Leu |

```
                        305                 310                 315                 320
Lys Asn Leu Gly Cys Ile Ser Gln Ala Gln Trp Val Ser Phe Thr Arg
                325                 330                 335
Arg Glu Gly Ser Leu Lys Leu Ser Ser Met Leu Leu Glu Thr Thr Ser
            340                 345                 350
Gly Ala Leu Ser Leu
        355

<210> SEQ ID NO 3
<211> LENGTH: 26
<212> TYPE: PRT
<213> ORGANISM: Artificial Sequence
<220> FEATURE:
<223> OTHER INFORMATION: NH2-Terminal Peptide of Human GPR-9-6

<400> SEQUENCE: 3

Met Ala Asp Asp Tyr Gly Ser Glu Ser Thr Ser Ser Met Glu Asp Tyr
1               5                   10                  15
Val Asn Phe Asn Phe Thr Asp Phe Tyr Cys
            20                  25

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 4
tcgaagggat ccctaacatg gctgatgact atggc                              35

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 5
aagaagtcta gaacccctca gagggagagt gctcc                              35

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 6
tcgaagaagc ttatgaacct gtggctcctg                                    30

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 7
aagaagtcta gatcacagtc ctgaattagc                                    30

<210> SEQ ID NO 8
<211> LENGTH: 879
<212> TYPE: DNA
```

<210> SEQ ID NO 8
<400> SEQUENCE: 8

```
atgaacctgt ggctcctggc ctgcctggtg gccggcttcc tgggagcctg ggcccccgct      60
gtccacaccc aagtgtgtctt tgaggactgc tgcctggcct accactaccc cattgggtgg    120
gctgtgctcc ggcgcgcctg gacttaccgg atccaggagg tgagcgggag ctgcaatctg    180
cctgctgcga tattctacct ccccaagaga cacaggaagg tgtgtgggaa ccccaaaagc    240
agggaggtgc agagagccat gaagctcctg gatgctcgaa ataaggtttt tgcaaagctc    300
caccacaaca ygcagacctt ccaagcaggc cctcatgctg taaagaagtt gagttctgga    360
aactccaagt tatcatcatc caagtttagc aatcccatca gcagcagcaa gaggaatgtc    420
tccctcctga tatcagctaa ttcaggactg tgagccggct catttctggg ctccatcggc    480
acaggagggg ccggatcttt ctccgataaa accgtcgccc tacagaccca gctgtcccca    540
cgcctctgtc ttttgggtca agtcttaatc cctgcacctg agttggtcct ccctctgcac    600
ccccaccacc tcctgcccgt ctggcaactg aaagaagga gttggcctga ttttaaccct    660
ttgccgctcc ggggaacagc acaatcctgg cagccagtg gctcttgtag agaaaactta    720
ggatacctct ctcactttct gtttcttgcc gtccaccccg gccatgcca gtgtgtcctc    780
tgggtcccct ccaaaaatct ggtcattcaa ggatcccctc caaggctat gcttttctat    840
aacttttaaa taaaccttgg ggggtgaatg gaataaaaa                            879
```

<210> SEQ ID NO 9
<211> LENGTH: 150
<212> TYPE: PRT
<213> ORGANISM: Homo Sapiens
<220> FEATURE:
<221> NAME/KEY: VARIANT
<222> LOCATION: (104)...(104)
<223> OTHER INFORMATION: Xaa= Met or Thr

<400> SEQUENCE: 9

```
Met Asn Leu Trp Leu Leu Ala Cys Leu Val Ala Gly Phe Leu Gly Ala
  1               5                  10                  15

Trp Ala Pro Ala Val His Thr Gln Gly Val Phe Glu Asp Cys Cys Leu
             20                  25                  30

Ala Tyr His Tyr Pro Ile Gly Trp Ala Val Leu Arg Arg Ala Trp Thr
         35                  40                  45

Tyr Arg Ile Gln Glu Val Ser Gly Ser Cys Asn Leu Pro Ala Ala Ile
     50                  55                  60

Phe Tyr Leu Pro Lys Arg His Arg Lys Val Cys Gly Asn Pro Lys Ser
 65                  70                  75                  80

Arg Glu Val Gln Arg Ala Met Lys Leu Leu Asp Ala Arg Asn Lys Val
                 85                  90                  95

Phe Ala Lys Leu His His Asn Xaa Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Lys Arg Asn Val Ser Leu Leu Ile
    130                 135                 140

Ser Ala Asn Ser Gly Leu
145                 150
```

<210> SEQ ID NO 10
<211> LENGTH: 876

<210> SEQ ID NO 11
<211> LENGTH: 149
<212> TYPE: PRT
<213> ORGANISM: Homo sapiens
<220> FEATURE:
<221> NAME/KEY: VARIANT
<222> LOCATION: (104)...(104)
<223> OTHER INFORMATION: Xaa= Met or Thr

<400> SEQUENCE: 11

```
Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Xaa Gln Thr Phe Gln Gly Pro His Ala
            100                 105                 110

Val Lys Lys Leu Ser Ser Gly Asn Ser Lys Leu Ser Ser Lys Phe
        115                 120                 125

Ser Asn Pro Ile Ser Ser Lys Arg Asn Val Ser Leu Leu Ile Ser
    130                 135                 140

Ala Asn Ser Gly Leu
145
```

<210> SEQ ID NO 12

<400> SEQUENCE: 10

```
atgaacctgt ggctcctggc ctgcctggtg gccggcttcc tgggagcctg ggcccccgct      60
gtccacaccc aaggtgtctt tgaggactgc tgcctggcct accactaccc cattgggtgg     120
gctgtgctcc ggcgcgcctg gacttaccgg atccaggagg tgagcgggag ctgcaatctg     180
cctgctgcga tattctacct ccccaagaga cacaggaagg tgtgtgggaa ccccaaaagc     240
agggaggtgc agagagccat gaagctcctg gatgctcgaa ataaggtttt tgcaaagctc     300
caccacaaca ygcagacctt ccaaggccct catgctgtaa agaagttgag ttctggaaac     360
tccaagttat catcatccaa gtttagcaat cccatcagca gcagcaagag gaatgtctcc     420
ctcctgatat cagctaattc aggactgtga gccggctcat ttctgggctc catcggcaca     480
ggaggggccg gatctttctc cgataaaacc gtcgccctac agaccagct gtccccacgc      540
ctctgtcttt tgggtcaagt cttaatccct gcacctgagt tggtcctccc tctgcacccc     600
caccacctcc tgcccgtctg gcaactggaa agaaggagtt ggcctgattt taaccttttg     660
ccgctccggg gaacagcaca atcctgggca gccagtggct cttgtagaga aaacttagga     720
tacctctctc actttctgtt tcttgccgtc caccccgggc catgccagtg tgtcctctgg     780
gtcccctcca aaaatctggt cattcaagga tcccctccca aggctatgct tttctataac     840
ttttaaataa accttggggg gtgaatggaa taaaaa                              876
```

-continued

```
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 12
taaggatccg caaggtgcct ttgaagactg ct                          32

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 13
caagaattct taattgttct ttctgggcat                             30

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 14
aattaaccct cactaaaggg aactgtggct ttttgcctgc                  40

<210> SEQ ID NO 15
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 15
taatacgact cactataggg tgttggtctt tctgggcatc                  40
```